United States Patent
Kwon et al.

(10) Patent No.: US 11,013,765 B2
(45) Date of Patent: *May 25, 2021

(54) CHIMERIC ANTIGEN RECEPTOR THAT BINDS HLA-DR AND CAR-T CELL

(71) Applicant: Eutilex Co., Ltd., Seoul (KR)

(72) Inventors: Byoung S. Kwon, Seoul (KR); Young Ho Kim, Seoul (KR); Kwang Hee Kim, Seoul (KR); Ji Won Chung, Seoul (KR); Young Gyoon Chang, Seoul (KR); Bo Rim Yi, Seoul (KR); Jung Yun Lee, Seoul (KR); Seung Hyun Lee, Seoul (KR); Sun Woo Im, Seoul (KR); Jin Kyung Choi, Seoul (KR); Hyun Tae Son, Seoul (KR); Eun Hye Yoo, Seoul (KR)

(73) Assignee: Eutilex Co., Ltd.

(*) Notice: Subject to any disclaimer, the term of this patent is extended or adjusted under 35 U.S.C. 154(b) by 0 days.

This patent is subject to a terminal disclaimer.

(21) Appl. No.: 16/715,462

(22) Filed: Dec. 16, 2019

(65) Prior Publication Data

US 2020/0237821 A1 Jul. 30, 2020

Related U.S. Application Data

(63) Continuation of application No. PCT/KR2019/010244, filed on Aug. 12, 2019.

(60) Provisional application No. 62/717,267, filed on Aug. 10, 2018, provisional application No. 62/867,503, filed on Jun. 27, 2019.

(51) Int. Cl.
*A61K 35/17* (2015.01)
*A61P 35/00* (2006.01)
*C12N 15/63* (2006.01)
*C07K 16/28* (2006.01)

(52) U.S. Cl.
CPC .............. *A61K 35/17* (2013.01); *A61P 35/00* (2018.01); *C07K 16/2833* (2013.01); *C12N 15/63* (2013.01)

(58) Field of Classification Search
CPC . A61K 35/17; A61K 2039/5156; A61P 35/00; C12N 2510/00; C07K 16/2833; C07K 2317/622; C07K 16/28
See application file for complete search history.

(56) References Cited

U.S. PATENT DOCUMENTS

| | | | |
|---|---|---|---|
| 5,459,127 | A | 10/1995 | Felgner |
| 5,580,859 | A | 12/1996 | Felgner |
| 5,589,466 | A | 12/1996 | Felgner |
| 5,693,622 | A | 12/1997 | Wolff |
| 9,862,775 | B2 | 1/2018 | Kwon |
| 1,023,325 | A1 | 3/2019 | Kwon |

| | | | | |
|---|---|---|---|---|
| 2016/0257762 | A1* | 9/2016 | Kwon | ............... G01N 33/57426 |
| 2019/0375851 | A1 | 12/2019 | Kwon | |
| 2020/0165342 | A1 | 5/2020 | Kwon | |

FOREIGN PATENT DOCUMENTS

| | | | |
|---|---|---|---|
| CA | 2012311 | 9/1990 | |
| KR | 10-0701923 | 3/2007 | |
| WO | WO 1988/07085 | 9/1988 | |
| WO | WO 1988/07086 | 9/1988 | |
| WO | WO 1988/09344 | 12/1988 | |
| WO | WO 1995/21931 | 8/1995 | |
| WO | WO 1996/17823 | 6/1996 | |
| WO | WO 1995/18863 | 7/1996 | |
| WO | WO 1996/25508 | 8/1996 | |
| WO | WO 2012/007900 | 1/2012 | |
| WO | WO-2012079000 A1 * | 6/2012 | ....... A61K 39/39558 |
| WO | WO 2015/133817 | 9/2015 | |
| WO | WO 2016/090190 | 6/2016 | |
| WO | WO 2016/094304 | 6/2016 | |
| WO | WO 2016/197064 | 12/2016 | |
| WO | WO 2017/011804 | 1/2017 | |
| WO | WO 2017/096329 | 6/2017 | |
| WO | WO 2018/005559 | 1/2018 | |
| WO | WO 2018/057904 | 3/2018 | |

OTHER PUBLICATIONS

Turtle et al. Durable Molecular Remissions in Chronic Lymphocytic Leukemia Treated With CD19-Specific Chimeric Antigen Receptor-Modified T Cells After Failure of Ibrutinib.Journal of Clinical Oncology. vol. 35 • No. 26 • Sep. 10, 2017 (Year: 2017).*
Ahn, "New monoclonal antibody that can inhibit the growth of L3055 Burkitt's lymphoma cells and HK follicular dendritic cells," Master's Thesis of Science, Graduate School of University of Ulsan, 35 pages, English abstract, 2008.
Anderton & Wraith, "Selection and fine-tuning of the autoimmune T-cell repertoire," Nat. Rev. Immunol., 2: 487-498, 2002.
Baniyash, "TCR zeta-chain downregulation: curtailing an excessive inflammatory immune response," Nat. Rev. Immunol., 4: 675-687, 2004.
Beal et al., "Kinetics of early T cell receptor signaling regulate the pathway of lytic granule delivery to the secretory domain," Immunity, 632-642, 2009.

(Continued)

*Primary Examiner* — Daniel E Kolker
*Assistant Examiner* — Brian Hartnett
(74) *Attorney, Agent, or Firm* — Fish & Richardson P.C.

(57) ABSTRACT

The present invention relates to an antigen-binding molecule comprising a heavy chain variable region comprising a heavy-chain complementarity-determining region 1 (HCDR1) comprising an amino acid sequence represented by Sequence No. 1, an HCDR2 comprising an amino acid sequence represented by Sequence No. 2, and an HCDR3 comprising an amino acid sequence represented by Sequence No. 3; a light-chain variable region comprising a light-chain complementarity-determining region 1 (LCDR1) comprising an amino acid sequence represented by Sequence No. 4, an LCDR2 comprising an amino acid sequence represented by Sequence No. 5, and an LCDR3 comprising an amino acid sequence represented by Sequence No. 6; wherein the antigen-binding molecule is a T cell receptor (TCR); and to a cell line expressing the same.

15 Claims, 26 Drawing Sheets

Specification includes a Sequence Listing.

(56) References Cited

OTHER PUBLICATIONS

Blackburn et al., "Coregulation of CD8+ T cell exhaustion by multiple inhibitory receptors during chronic viral infection," Nat. Immunol., 10: 29-37, 2009.
Brown et al., "Regression of glioblastoma after chimeric antigen receptor T-cell therapy," N. Engl. J. Med., 375: 2561-2569, 2016.
Caruso et al., "Tuning sensitivity of CAR to EGFR density limits recognition of normal tissue while maintaining potent antitumor activity," Cancer Res., 75: 3505-3518, 2015.
Chang et al., "Identification and selective expansion of functionally superior T cells expressing chimeric antigen receptors," J. Transl. Med., 13: 161, 2015.
Chen and Okayama, "High-Efficiency Transformation of Mammalian Cells by Plasmid DNA", Mol. Cell. Biol. 7: 2745-2752, 1987.
Chiu et al., "Sprouty-2 regulates HIV-specific T cell polyfunctionality," J. Clin. Invest., 124(1): 198-208, 2014.
Curiel et al., "High-Efficiency Gene Transfer Mediated by Adenovirus Coupled to DNA-Polylysine Complexes", Hum. Gene Ther. 3: 147-154, 1992.
Danjoh et al., "Development of a robust method for establishing B cell lines using Epstein-Barr virus," In Vitro Cell. Dev. Biol Anim, 48: 393-402, 2012.
Davila et al., "Efficacy and toxicity management of 19-28z CAR T cell therapy in B cell acute lymphoblastic leukemia," Sci. Transl. Med., 2014, 6: 224ra225, 2014.
DeNardo et al., "Direct antilymphoma effects on human lymphoma cells of monotherapy and combination therapy with CD20 and HLA-DR antibodies and 90Y-labeled HLA-DR antibodies," Clin. Cancer Res., 11(19 Suppl): 7075s-7079s, 2005.
Ding et al., "Polyfunctional CD4(+) T cells are essential for eradicating advanced B-cell lymphoma after chemotherapy," Blood, 120: 2229-2239, 2012.
Eyquem et al., "Targeting a CAR to the TRAC locus with CRISPR/Cas9 enhances tumour rejection," Nature, 543: 113-117, 2017.
Fedorov et al., "PD-1- and CTLA-4-based inhibitory chimeric antigen receptors (iCARs) divert off-target immunotheragy responses," Sci. Transl. Med., 5: 215ra172, 2013.
Feigner et al., "Lipofection: a highly efficient, lipid-mediated DNA-transfection procedure," Proc. Natl. Acad. Sci. USA. 84: 7413-7417, 1987.
Franzese et al., "Polyfunctional Melan-A-specific tumor-reactive CD8(+) T cells elicited by dacarbazine treatment before peptide-vaccination depends on AKT activation sustained by ICOS," Oncoimmunology, 5: e1114203, 2016.
Frigault et al., "Identification of chimeric antigen receptors that mediate constitutive or inducible proliferation of T cells," Cancer Immunol. Res., 3: 356-367, 2015.
Gallegos et al., "Control of T cell antigen reactivity via programmed TCR downregulation," Nat. Immunol., 17: 379-386, 2016.
Gatzka et al., "Altered thymic selection and increased autoimmunity caused by ectopic expression of DRAK2 during T cell development," J. Immunol., 183: 285-297, 2009.
Gomes-Silva et al., "CD7-edited T cells expressing a CD7-specific CAR for the therapy of T-cell malignancies," Blood, 130: 285-296, 2017.
Gopal, "Gene Transfer Method for Transient Gene Expression, Stable Transformation, and Cotransformation of Suspension Cell Cultures", Mol. Cell Biol., 5: 1188-1190, 1985.
Grupp et al., "Chimeric antigen receptor-modified T cells for acute lymphoid leukemia," N. Engl. J. Med., 368: 1509-1518, 2013.
Gusso et al., "Humanization of Monoclonal Antibodies," Methods in Enzymology, 203: 99-121, 1991.
Han et al., "Adnectin-based design of chimeric antigen receptor for T cell engineering," Mol., Ther., 25: 2466-2476, 2017.
Han et al., "Desensitized chimeric antigen receptor cells selectively recognize target cells with enhanced antigen expression," Nature Communications, 9: article 468, 2018.
Han et al., "Selective killing of malignant B cells using T cells redirected against malignancy variant receptor," Journal for Immunotherapy of Cancer, 2(Suppl 3): 16, 2014.
Herne et al., "Surface expression of the invariant chain (CD74) is independent of concomitant expression of major histocompatibility complex class II antigens,", Immunology, 84: 177-182, 1995.
Huijbers et al., "Minimal tolerance to a tumor antigen encoded by a cancer-germline gene," J. Immunol., 188: 111-121, 2012.
Ichim & Wells, "Generation of high-titer viral preparations by concentration using successive rounds of ultracentrifugation," J. Transl. Med., 9: 137, 2011.
International Search Report and Written Opinion in International Appln. No. PCT/IB2018/000227, dated Jun. 28, 2018, 5 pages.
International Search Report and Written Opinion in International Appln. No. PCT/KR2015/002089, dated Jul. 6, 2015, 125 pages.
Ivanov et al., "Monoclonal antibodies directed to CD20 and HLA-DR can elicit homotypic adhesion followed by lysosome-mediated cell death in human lymphoma and leukemia cells," J. Clin. Invest., 119: 2143-2159, 2009.
Jedema et al., "New CFSE-based assay to determine susceptibility to lysis by cytotoxic T cells of leukemic precursor cells within a heterogeneous target cell population," Blood, 103: 2677-2682, 2004.
Jenkins et al., "The strength of T cell receptor signal controls the polarization of cytotoxic machinery to the immunological synapse," Immunity, 31: 621-631, 2009.
Johnson & Jun., "Driving gene-engineered T cell immunotherapy of cancer," Cell Research, 27: 38-58, 2017.
Kalos et al., "T cells with chimeric antigen receptors have potent antitumor effects and can establish memory in patients with advanced leukemia," Sci. Transl. Med., 3: 95ra73, 2011.
Kochenderfer et al., "B-cell depletion and remissions of malignancy along with cytokine-associated toxicity in a clinical trial of anti-CD19 chimeric-antigen-receptor-transduced T cells," Blood, 119: 2709-2720, 2012.
Kochenderfer et al., "Chemotherapy-refractory diffuse large B-cell lymphoma and indolent B-cell malignancies can be effectively treated with autologous T cells expressing an anti-CD19 chimeric antigen receptor," J. Clin. Oncol., 33: 540-549, 2015.
Kochenderfer et al., "Eradication of B-lineage cells and regression of lymphoma in a patient treated with autologous T cells genetically engineered to recognize CD19," Blood, 116: 4099-4102, 2010.
Kumar et al., "Increased sensitivity of antigen-experienced T cells through the enrichment of oligomeric T cell receptor complexes," Immunity, 35: 375-387, 2011.
Lamers et al., "Treatment of metastatic renal cell carcinoma with autologous T-lymphocytes genetically retargeted against carbonic anhydrase IX: first clinical experience," J. Clin. Oncol., 24: e20-22, 2006.
Lieberman, "The ABCs of granule-mediated cytotoxicity: new weapons in the arsenal," Nat. Rev. Immunol., 3: 361-370, 2003.
Lin et al., "A phase I/II dose escalation study of apolizumab (Hu1D10) using a stepped-up dosing schedule in patients with chronic lymphocytic leukemia and acute leukemia," Leuk. Lymphoma, 50: 1958-1963, 2009.
Liu et al., "Affinity-tuned ErbB2 or EGFR chimeric antigen receptor T cells exhibit an increased therapeutic index against tumors in mice," Cancer Res., 75: 3596-3607, 2015.
Liu et al., "Up-regulation of vascular endothelial growth factor-D expression in clear cell renal cell carcinoma by CD74: a critical role in cancer cell tumorigenesis," J. Immunol., 181: 6584-6594, 2008.
Long et al., "4-1BB costimulation ameliorates T cell exhaustion induced by tonic signaling of chimeric antigen receptors," Nat. Med., 21: 581-590, 2015.
Machey et al., "Gene transfer from targeted liposomes to specific lymphoid cells by electroporation", Proc. Natl. Acad. Sci. USA 85: 8027-8031, 1988.
Mamonkin et al., "T-cell-directed chimeric antigen receptor for the selective treatment of T-cell malignancies," Blood, 126: 983-992, 2015.
Mandl et al., "T cell-positive selection uses self-ligand binding strength to optimize repertoire recognition of foreign antigens," Immunity, 38: 263-274, 2013.

(56) References Cited

OTHER PUBLICATIONS

Mariuzza et al., "The structural basis of antigen-antibody recognition," Annu. Rev. Biophys. Biophys. Chem., 16: 139-159, 1987.
Martinez-Lostao et al., "How do cytotoxic lymphocytes kill cancer cells?" Clin. Cancer. Res., 21: 5047-5056, 2015.
Maus et al., "Antibody-modified T cells: CARs take the front seat for hematologic malignancies," Blood, 123: 2625-2635, 2014.
Milone et al., "Chimeric receptors containing CD137 signal transduction domains mediate enhanced survival of T cells and increased antileukemic efficacy in vivo," Mol. Ther., 17: 1453-1464, 2009.
Morgan et al., "Case report of a serious adverse event following the administration of T cells transduced with a chimeric antigen receptor recognizing ERBB2," Mol. Ther., 18: 843-851, 2010.
Nagy et al., "Fully human, HLA-DR-specific monoclonal antibodies efficiently induce programmed death of malignant lymphoid cells," Nat. Med., 8: 801-807, 2002.
Pageon et al., "Functional role of T-cell receptor nanoclusters in signal initiation and antigen discrimination," Proc. Natl. Acad. Sci. USA, 113: E5454-5463, 2016.
Porter et al., "Chimeric antigen receptor-modified T cells in chronic lymphoid leukemia," N. Engl. J. Med., 365: 725-733, 2011.
Rufener, et al., "Preserved activity of CD20-specific chimeric antigen receptor-expressing T cells in the presence of Rituximab," Cancer Immunol. Res., 2016, 4:509-519.
Savoldo et al., "CD28 costimulation improves expansion and persistence of chimeric antigen receptor-modified T cells in lymphoma patients," J. Clin. Invest., 121(5): 1822-1826, 2011.
Sebzda et al., "Selection of the T cell repertoire," Annu. Rev. Immunol., 17: 829-874, 1999.
Shackelford et al., "HLA-DR antigens: structure, separation of subpopulations, gene cloning and function," Immunol. Rev., 66: 133-187, 1982.
Speiser et al., "Regulatory circuits of T cell function in cancer," Nat. Rev. Immunol., 16: 599-611, 2016.
Taylor et al., "A DNA-based T cell receptor reveals a role for receptor clustering in ligand discrimination," Cell, 2017, 159:108-119.
Van den Berg et al., "Cellular-level versus receptor-level response threshold hierarchies in T-cell activation," Front. Immunol., 2013, 4:250.
Van der Stegen et al., "The pharmacology of second-generation chimeric antigen receptors," Nat. Rev. Drug Discov., 14: 499-509, 2015.
Van Meerten et al., "Novel antibodies against follicular non-Hodgkin's lymphoma," Best Pract. Res. Clin. Haematol., 24(2): 231-526, 2011.
Vigano et al., "Functional avidity: a measure to predict the efficacy of effector T cells?" Clin. Dev. Immunol., 2012: 153863, 2012.
Viola & Lanzavecchia, "T cell activation determined by T cell receptor number and tunable thresholds," Science, 273: 104-106, 1996.
Wherry & Kurachi, "Molecular and cellular insights into T cell exhaustion," Nat. Rev. Immunol., 15: 486-499, 2015.
Winkler et al., "Changing the antigen binding specificity by single point mutations of an anti-p24 (HIV-1) antibody," J. Imm., 265: 4505-4514, 2000.
Wu et al., "Hepatocyte-directed Gene Transfer in Vivo Leads to Transient Improvement of Hypercholesterolemia in Low Density Lipoprotein Receptor-deficient Rabbits", J. Biol. Chem. 267: 963, 1992.
Wu et al., "Receptor-mediated Gene Delivery and Expression in Vivo", J. Biol. Chem. 263: 14621, 1988.
Wu et al., "Receptor-mediated in Vitro Gene Transformation by a Soluble DNA Carrier System", J. Biol. Chem. 262: 4429-4432, 1987.
Xiang et al., "Targeted activation of human Vgamma9Vdelta2-T cells controls epstein-barr virus-induced B cell lymphoproliferative disease," Cancer Cell, 26: 565-576, 2014.
Yang et al., "In vivo and in vitro gene transfer to mammalian somatic cells by particle bombardment", Proc. Natl. Acad. Sci., 87: 9568-9572, 1990.
Young et al., "Epstein-Barr virus: more than 50 years old and still providing surprises," Nat. Rev. Cancer, 16: 789-802, 2016.
Yuan et al., "CTLA-4 blockade enhances polyfunctional NY-ESO-1 specific T cell responses in metastatic melanoma patients with clinical benefit," Proc. Natl. Acad. Sci. USA, 105: 20410-20415, 2008.
Zhang et al., "Epstein-Barr virus (EBV) latent membrane protein 1 increases HLA class II expression in an EBV-negative B cell line," Eur. J. Immunol., 24: 1467-1470, 1994.
EP Extended Search Report in European Appln No. 18757730.9, dated Oct. 9, 2020, 7 pages.

* cited by examiner

[FIG. 1]

```
muMVR_VH  QVQLKESGPGLVAPSQSLSITCTVSGFSLS[RTSVH]WVRQPPGKGLEWLG[MIWGGGSTDYNSALKS]
AAV40168  QVQLQESGPGLVKPSETLSLTCTVSGGSIS[SYYWS]WIRQPPGKGLEWIG[YIYYNGSTNYNPSLKS]
huMVR.H1  QVQLQESGPGLVKPSETLSLTCTVSGGSIS[RTSVH]WIRQPPGKGLEWIG[MIWGGGSTDYNSALKS]
huMVR.H2  QVQLQESGPGLVKPSETLSLTCTVSGFSLS[RTSVH]WIRQPPGKGLEWLG[MIWGGGSTDYNSALKS]

muMVR_VH  RLSISKDNSKSQVFLKMNSLQTDDTAMYYCAR[NEGDTTAGTWFAY]WGQGTLVTVSS
AAV40168  RVTISVDTSKNQFSLKLSSVTAADTAVYYCAR[VMGIAAAGYYFDY]WGQGTLVTVSS
huMVR.H1  RVTISVDTSKNQFSLKLSSVTAADTAVYYCAR[NEGDTTAGTWFAY]WGQGTLVTVSS
huMVR.H2  RLTISVDSKNQFSLKLSSVTAADTAVYYCAR[NEGDTTAGTWFAY]WGQGTLVTVSS
```

[FIG. 2]

```
muMVR_VL  DIQMTQSSSYLSVSLGGRVTITC[KASDHINNWLA]WYQQKPGNAPRLLIS[GATSLET]
hu4D5     DIQMTQSPSSLSASVGDRVTITC[RASQDVNTAVA]WYQQKPGKAPKLLIY[SASFLYS]
huMVR.L1  DIQMTQSPSSLSASVGDRVTITC[KASDHINNWLA]WYQQKPGKAPKLLIY[GATSLES]
huMVR.L2  DIQMTQSPSSLSASVGDRVTITC[KASDHINNWLA]WYQQKPGKAPKLLIS[GATSLET]

muMVR_VL  GVPSRFSGSGSGRDYTLSITSLQTEDVATYYC[QQYWSTPFT]FGSGTKLEIK
hu4D5     GVPSRFSGSRSGTDFTLTISSLQPEDFATYYC[QQHYTTPPT]FGQGTKVEIK
huMVR.L1  GVPSRFSGSGSGTDYTLTISSLQPEDFATYYC[QQYWSTPFT]FGQGTKVEIK
huMVR.L2  GVPSRFSGSGSGDYTLTISSLQPEDFATYYC[QQYWSTPFT]FGQGTKVEIK
```

[FIG. 3]

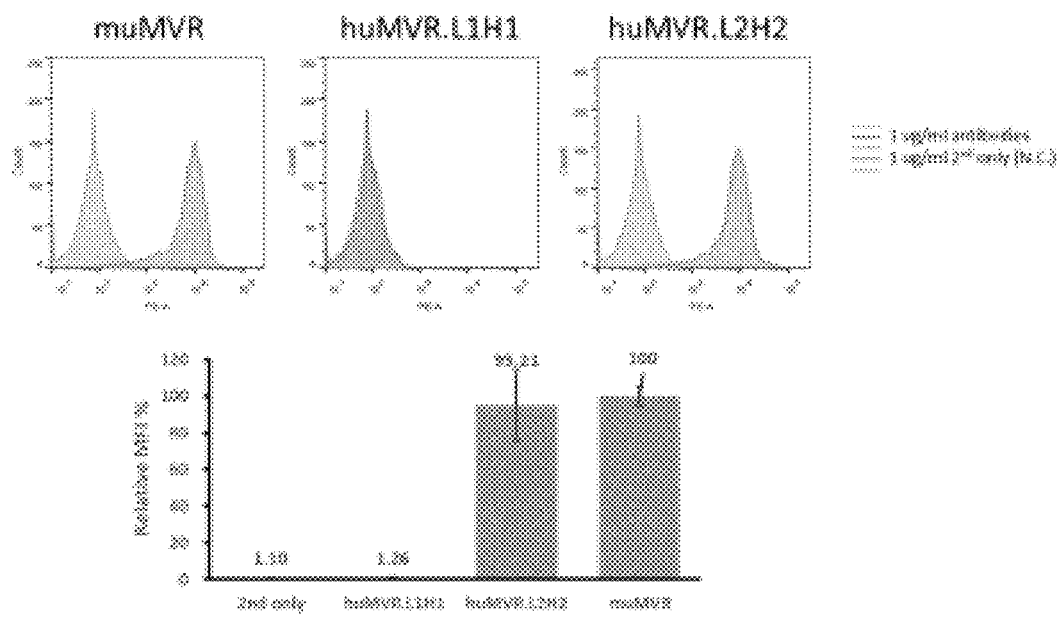

[FIG. 4]
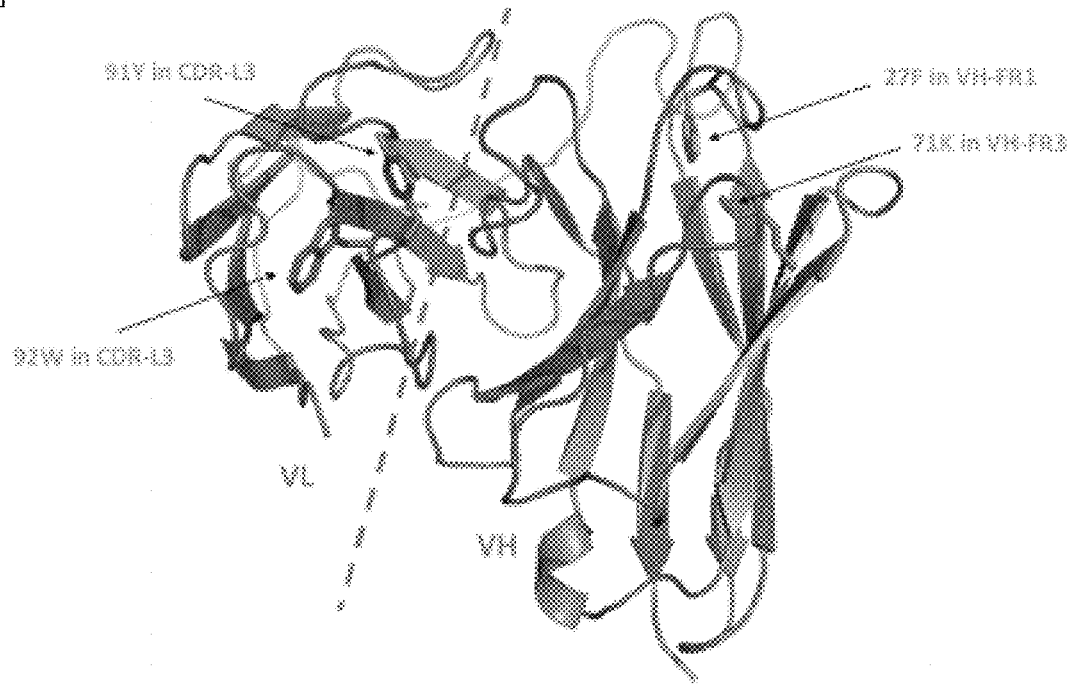
[FIG. 5a]
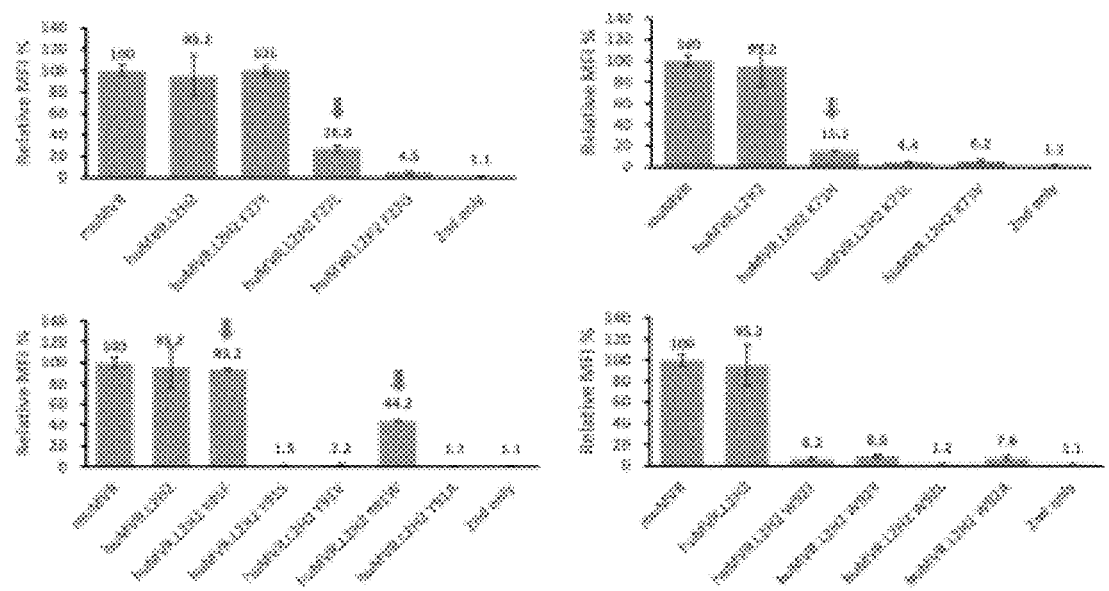

[FIG. 5b]
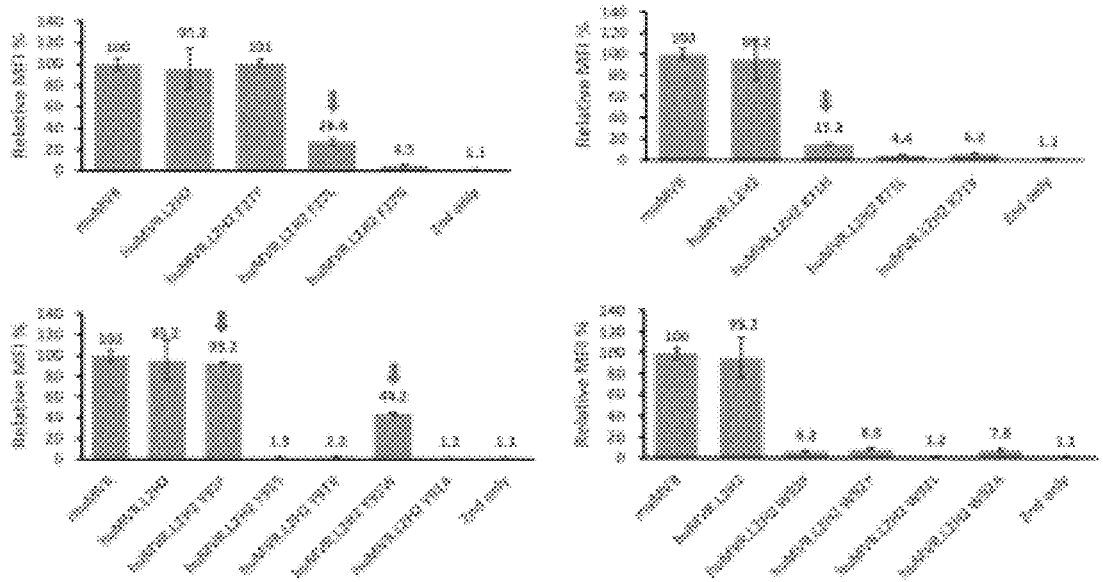
[FIG. 6a]
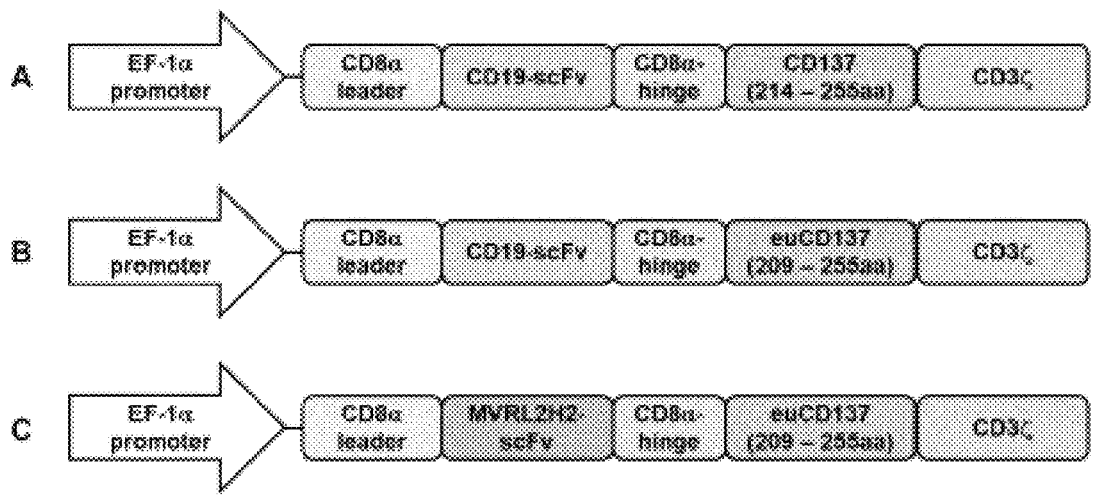

[FIG. 6b]
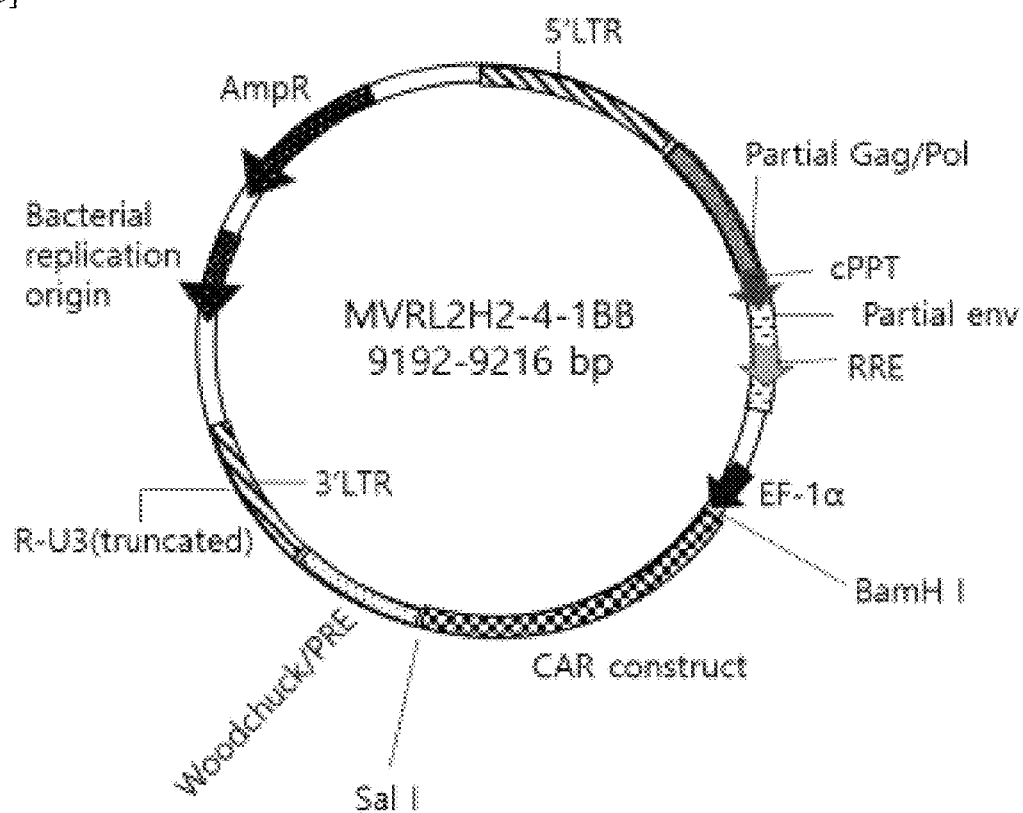

[FIG. 7a]

7. Variable region of huMVR.H2 heavy chain

QVQLQESGPGLVKPSETLSLTCTVSGFSLSRYSVHWIRQPPGKGLEWLGMIWGGGSTDYNSALKSRLTISKDNSK
NQVSLKLSSVTAADTAVYYCARNEGOTTAGTWFAYWGQGTLVTVSS

8. Variable region of huMVR.L2 Light chain

DIQMTQSPSSLSASVGDRVTITCKASDHINNWLAWYQQKPGKAPKLLISGATSLETGVPSRFSGSGSGKDYTLTIS
SLQPEDFATYYCQQYWSTPFTFGQGTKVEIK 9. scFv of huMVRL2H2

DIQMTQSPSSLSASVGDRVTITCKASDHINNWLAWYQQKPGKAPKLLISGATSLETGVPSRFSGSGSGKDYTLTIS
SLQPEDFATYYCQQYWSTPFTFGQGTKVEIKGGGGSGGGGSGGGGSQVQLQESGPGLVKPSETLSLTCTVSGFSL
SRYSVHWIRQPPGKGLEWLGMIWGGGSTDYNSALKSRLTISKDNSKNQVSLKLSSVTAADTAVYYCARNEGOTT
AGTWFAYWGQGTLVTVSS

10. Variable region of huMVR.H1 heavy chain

QVQLQESGPGLVKPSETLSLTCTVSGGSISRYSVHWIRQPPGKGLEWIGMIWGGGSTDYNSALKSRVTISVDTSK
NQFSLKLSSVTAADTAVYYCARNEGOTTAGTWFAYWGQGTLVTVSS

11. Variable region of huMVR.L1 light chain

DIQMTQSPSSLSASVGDRVTITCRASDHINNWLAWYQQKPGKAPKLLLYGATRLESGVPSRFSGSGSGTDYTLTI
SSLQPEDFATYYCQQYWSTPFTFGGGTKVEIK

[FIG. 7b]

12. scFv of huMVR.1H1

DIQMTQSPSSLSASVGDRVTITCRASDHINNWLAWYQQKPGKAPKLLIYGATRLESGVPSRFSGSGSGTDYTLTI

SSLQPEDFATYYCQQYWSTPFTFGGGTKVEIKGGGGSGGGGSGGGGSQVQLQESGPGLVKPSETLSLTCTVSGG

SISRYSVHWIRQPPGKGLEWIGMIWGGGSTDYNSALKSRVTISVDTSKNQFSLKLSSVTAADTAVYYCARNEGDT

TAGTWFAYWGQGTLVTVSS 13. 4-1BB signaling domain

KRGRKKLLYIFKQPFMRPVQTTQEEDGCSCRFPEEEEGGCEL 14. euCD137

RFSVVKRGRKKLLYIFKQPFMRPVQTTQEEDGCSCRFPEEEEGGCEL

[FIG. 7c]

nt sequence of MVR L2H2 CAR

GATATTCAGATGACCCAGTCCCCGAGCTCCCTGTCCGCCTCTGTGGGCGATAGGGTCACCATCACCTGCAAGG

CCAGTGACCACATCAACAACTGGCTGGCCTGGTATCAACAGAAACCAGGAAAAGCTCCGAAACTACTGATCA

GCGGCGCCACCTCTCTGGAAACCGGAGTCCCTTCTCGCTTCTCTGGTTCCGGATCTGGGAAGGATTACACTCT

GACCATCAGCAGTCTGCAGCCGGAAGACTTCGCAACTTATTACTGTCAGCAGTACTGGTCCACCCCCTTCACC

TTCGGACAGGGTACCAAGGTGGAGATCAAAGGCGGAGGCGGATCTGGCGGCGGAGGAAGTGGCGGAGGG

GGATCTCAGGTGCAGCTGCAGGAGTCGGGCCCAGGACTGGTGAAGCCTTCGGAGACCCTGTCCCTCACCTGC

ACTGTCTCTGGTTTCTCCCTGAGTCGGTACTCTGTGCATTGGATCCGGCAGCCCCCAGGGAAGGGACTGGAGT

GGCTGGGGATGATCTGGGGAGGCGGCAGCACCGACTACAACAGCGCCCTGAAGTCCCGACTGACCATATCA

AAGGACAACTCCAAGAACCAGGTGTCCTTGAAGCTGAGCTCTGTGACCGCTGCGGACACGGCCGTGTATTAC

TGTGCGAGAAATGAGGGCGATACCACCGCCGGCACTTGGTTTGCCTATTGGGGCCAGGGAACCCTGGTCACC

GTCTCCTCAACCACGACGCCAGCGCCGCGACCACCAACACCGGCGCCCACCATCGCTAGCCAGCCCCTGTCC

CTGCGCCCAGAGGCGTGCCGGCCAGCGGCGGGGGCGCAGTGCACACGAGGGGGCTGGACTTCGCCTGTG

ATATCTACATCTGGGCGCCCTTGGCCGGGACTTGTGGGGTCCTTCTCCTGTCACTGGTTATCACCCTTTACTGCA

AACGGGGCAGAAAGAAACTCCTGTATATATTCAAACAACCATTTATGAGACCAGTACAAACTACTCAAGAGGA

AGATGGCTGTAGCTGCCGATTTCCAGAAGAAGAAGAAGGAGGATGTGAACTG

AGAGTGAAGTTCAGCAGGAGCGCAGACGCCCCCGCGTACAAGCAGGGCCAGAACCAGCTCTATAACGAGCT

CAATCTAGGACGAAGAGAGGAGTACGATGTTTTGGACAAGAGACGTGGCCGGGACCCTGAGATGGGGGGA

AAGCCGAGAAGGAAGAACCCTCAGGAAGGCCTGTACAATGAACTGCAGAAAGATAAGATGGCGGAGGCCT

ACAGTGAGATTGGGATGAAAGGCGAGCGCCGGAGGGGCAAGGGGCACGATGGCCTTTACCAGGGTCTCAG

TACAGCCACCAAGGACACCTACGACGCCCTTCACATGCAGGCCCTGCCCCCTCGCTAA

[FIG. 7d]

16. sequence of MVR.L2H2 CAR_euCD137

GATATTCAGATGACCCAGTCCCCGAGCTCCCTGTCCGCCTCTGTGGGCGATAGGGTCACCATCACCTGCAAGG
CCAGTGACCACATCAACAACTGGCTGGCCTGGTATCAACAGAAACCAGGAAAAGCTCCGAAACTACTGATCA
GCGGCGCCACCTCTCTGGAAACCGGAGTCCCTTCTCGCTTCTCTGGTTCCGGATCTGGGAAGGATTACACTCT
GACCATCAGCAGTCTGCAGCCGGAAGACTTCGCAACTTATTACTGTCAGCAGTACTGGTCCACCCCCTTCACC
TTCGGACAGGGTACCAAGGTGGAGATCAAAGGCGGAGGCGGATCTGGCGGCGGAGGAAGTGGCGGAGGG
GGATCTCAGGTGCAGCTGCAGGAGTCGGGCCCAGGACTGGTGAAGCCTTCGGAGACCCTGTCCTCACCTGC
ACTGTCTCTGGTTTCTCCCTGAGTCGGTACTCTGTGCATTGGATCCGGCAGCCCCCAGGGAAGGGACTGGAGT
GGCTGGGGATGATCTGGGGAGGCGGCAGCACCGACTACAACAGCGCCCTGAAGTCCCGACTGACCATATCA
AAGGACAACTCCAAGAACCAGGTGTCCTTGAAGCTGAGCTCTGTGACCGCTGCGGACACGGCCGTGTATTAC
TGTGCCGAGAAATGAGGGCGATACCACCGCCGGCACTTGGTTTGCCTATTGGGGCCAGGGAACCCTGGTCACC
GTCTCCTCAACCACGACGCCAGCGCCGCGACCACCAACACCGGCGCCCACCATCGCTAGCCAGCCCCTGTCC
CTGCGCCCAGAGGCGTGCCGGCCAGCGGCGGGGGGCGCAGTGCACACGAGGGGGCTGGACTTCGCCTGTG
ATATCTACATCTGGGCGCCCTTGGCCGGGACTTGTGGGGTCCTTCTCCTGTCACTGGTTATCACCCTTTACTGC
CGTTTCTCTGTTGTTAAACGGGGCAGAAAGAAACTCCTGTATATATTCAAACAACCATTTATGAGACCAGTACA
AACTACTCAAGAGGAAGATGGCTGTAGCTGCCGATTTCCAGAAGAAGAAGAAGGAGGATGTGAACTG
AGAGTGAAGTTCAGCAGGAGCGCAGACGCCCCCGCGTACAAGCAGGGCCAGAACCAGCTCTATAACGAGCT
CAATCTAGGACGAAGAGAGGAGTACGATGTTTTGGACAAGAGACGTGGCCGGGACCCTGAGATGGGGGGA
AAGCCGAGAAGGAAGAACCCTCAGGAAGGCCTGTACAATGAACTGCAGAAAGATAAGATGGCGGAGGCCT
ACAGTGAGATTGGGATGAAAGGCGAGCGCCGGAGGGGCAAGGGGCACGATGGCCTTTACCAGGGTCTCAG
TACAGCCACCAAGGACACCTACGACGCCCTTCACATGCAGGCCCTGCCCCCTCGCTAA

[FIG 7e]

17. sequence of CD19 CAR

GACATCCAGATGACACAGACTACATCCTCCCTGTCTGCCTCTCTGGGAGACAGAGTCACCATCAGTTGCAGGG
CAAGTCAGGACATTAGTAAATATTTAAATTGGTATCAGCAGAAACCAGATGGAACTGTTAAACTCCTGATCTAC
CATACATCAAGATTACACTCAGGAGTCCCATCAAGGTTCAGTGGCAGTGGGTCTGGAACAGATTATTCTCTCAC
CATTAGCAACCTGGAGCAAGAAGATATTGCCACTTACTTTTGCCAACAGGGTAATACGCTTCCGTACACGTTC
GGAGGGGGGACCAAGCTGGAGATCACAGGTGGCGGTGGCTCGGGCGGTGGTGGGTCGGGTGGCGGCGGA
TCTGAGGTGAAACTGCAGGAGTCAGGACCTGGCCTGGTGGCGCCCTCACAGAGCCTGTCCGTCACATGCACT
GTCTCAGGGGTCTCATTACCCGACTATGGTGTAAGCTGGATTCGCCAGCCTCCACGAAAGGGTCTGGAGTGGC
TGGGAGTAATATGGGGTAGTGAAACCACATACTATAATTCAGCTCTCAAATCCAGACTGACCATCATCAAGGAC
AACTCCAAGAGCCAAGTTTTCTTAAAAATGAACAGTCTGCAAACTGATGACACAGCCATTTACTACTGTGCCA
AACATTATTACTACGGTGGTAGCTATGCTATGGACTACTGGGGCCAAGGAACCTCAGTCACCGTCTCCTCA
ACCACGACGCCAGCGCCGCGACCACCAACACGGCGCCCACCATCGCTAGCCAGCCCCTGTCCCTGCGCCC
AGAGGCGTGCCGGCCAGCGGCGGGGGGCGCAGTGCACACGAGGGGGCTGGACTTCGCCTGTGATATCTAC
ATCTGGGCGCCCTTGGCCGGGACTTGTGGGGTCCTTCTCCTGTCACTGGTTATCACCCTTTACTGC
AAACGGGGCAGAAAGAAACTCCTGTATATATTCAAACAACCATTTATGAGACCAGTACAAACTACTCAAGAGG
AAGATGGCTGTAGCTGCCGATTTCCAGAAGAAGAAGAAGGAGGATGTGAACTG
AGAGTGAAGTTCAGCAGGAGCGCAGACGCCCCCGCGTACAAGCAGGGCCAGAACCAGCTCTATAACGAGCT
CAATCTAGGACGAAGAGAGGAGTACGATGTTTTGGACAAGAGACGTGGCCGGGACCCTGAGATGGGGGGA
AAGCCGAGAAGGAAGAACCCTCAGGAAGGCCTGTACAATGAACTGCAGAAAGATAAGATGGCGGAGGCCT
ACAGTGAGATTGGGATGAAAGGCGAGCGCCGGAGGGGCAAGGGGCACGATGGCCTTTACCAGGGTCTCAG
TACAGCCACCAAGGACACCTACGACGCCCTTCACATGCAGGCCCTGCCCCCTCGCTAA

[FIG. 7f]

18. sequence of CD19 CAR_euCD137

GACATCCAGATGACACAGACTACATCCTCCCTGTCTGCCTCTCTGGGAGACAGAGTCACCATCAGTTGCAGGG

CAAGTCAGGACATTAGTAAATATTTAAATTGGTATCAGCAGAAACCAGATGGAACTGTTAAACTCCTGATCTAC

CATACATCAAGATTACACTCAGGAGTCCCATCAAGGTTCAGTGGCAGTGGGTCTGGAACAGATTATTCTCTCAC

CATTAGCAACCTGGAGCAAGAAGATATTGCCACTTACTTTTGCCAACAGGGTAATACGCTTCCGTACACGTTC

GGAGGGGGGACCAAGCTGGAGATCACAGGTGGCGGTGGCTCGGGCGGTGGTGGGTCGGGTGGCGGCGGA

TCTGAGGTGAAACTGCAGGAGTCAGGACCTGGCCTGGTGGCGCCCTCACAGAGCCTGTCCGTCACATGCACT

GTCTCAGGGGTCTCATTACCCGACTATGGTGTAAGCTGGATTCGCCAGCCTCCACGAAAGGGTCTGGAGTGGC

TGGGAGTAATATGGGGTAGTGAAACCACATACTATAATTCAGCTCTCAAATCCAGACTGACCATCATCAAGGAC

AACTCCAAGAGCCAAGTTTTCTTAAAAATGAACAGTCTGCAAACTGATGACACAGCCATTTACTACTGTGCCA

AACATTATTACTACGGTGGTAGCTATGCTATGGACTACTGGGGCCAAGGAACCTCAGTCACCGTCTCCTCA

ACCACGACGCCAGCGCCGCGACCACCAACACCGGCGCCCACCATCGCTAGCCAGCCCCTGTCCCTGCGCCC

AGAGGCGTGCCGGCCAGCGGCGGGGGGCGCAGTGCACACGAGGGGGCTGGACTTCGCCTGTGATATCTAC

ATCTGGGCGCCCTTGGCCGGGACTTGTGGGGTCCTTCTCCTGTCACTGGTTATCACCCTTTACTGC

CGTTTCTCTGTTGTT

AAACGGGGCAGAAAGAAACTCCTGTATATATTCAAACAACCATTTATGAGACCAGTACAAACTACTCAAGAGG

AAGATGGCTGTAGCTGCCGATTTCCAGAAGAAGAAGAAGGAGGATGTGAACTG

AGAGTGAAGTTCAGCAGGAGCGCAGACGCCCCCGCGTACAAGCAGGGCCAGAACCAGCTCTATAACGAGCT

CAATCTAGGACGAAGAGAGGAGTACGATGTTTTGGACAAGAGACGTGGCCGGGACCCTGAGATGGGGGA

AAGCCGAGAAGGAAGAACCCTCAGGAAGGCCTGTACAATGAACTGCAGAAAGATAAGATGGCGGAGGCCT

ACAGTGAGATTGGGATGAAAGGCGAGCGCCGGAGGGGCAAGGGGCACGATGGCCTTTACCAGGGTCTCAG

TACAGCCACCAAGGACACCTACGACGCCCTTCACATGCAGGCCCTGCCCCCTCGCTAA GTCGACA

[FIG. 7g]

19. EF1a-promoter

Cgtgaggctccggtgcccgtcagtgggcagagcgcacatcgcccacagtccccgagaagttggggggaggggtcggcaattgaaccg gtgcctagagaaggtggcgcggggtaaactgggaaagtgatgtcgtgtactggctccgcctttttcccgagggtgggggagaaccgtat ataagtgcagtagtcgccgtgaacgttctttttcgcaacgggtttgccgccagaacacaggtaagtgccgtgtgtggttcccgcgggcctgg cctctttacgggttatggcccttgcgtgccttgaattacttccacctggctgcagtacgtgattcttgatcccgagcttcgggttggaagtgggt gggagagttcgaggccttgcgcttaaggagccccttcgcctcgtgcttgagttgaggcctggcctgggcgctgggccgccgcgtgcga atctggtggcaccttcgcgcctgtctcgctgctttcgataagtctctagccatttaaaatttttgatgacctgctgcgacgctttttttctggcaag atagtcttgtaaatgcgggccaagatctgcacactggtatttcggtttttggggccgcgggcggcgacggggcccgtgcgtcccagcgca catgttcggcgaggcggggcctgcgagcgcggccaccgagaatcggacgggggtagtctcaagctggccggcctgctctggtgcctgg cctcgcgccgccgtgtatcgccccgccctgggcggcaaggctggcccggtcggcaccagttgcgtgagcggaaagatggccgcttcccg gccctgctgcagggagctcaaaatggaggacgcggcgctcgggagagcgggcgggtgagtcacccacacaaaggaaaagggcctttc cgtcctcagccgtcgcttcatgtgactccactgagtaccgggcgccgtccaggcacctcgattagttctcgagctttttggagtacgtcgtctttta ggttgggggaggggttttatgcgatggagtttccccacactgagtgggtggagactgaagttaggccagcttggcacttgatgtaattct cctggaattggccctttttgagtttggatcttggttcattctcaagcctcagacagtggtcaaagttttttcttccattcaggtgtcgtga

[FIG. 7h]

20. CD8-α leader sequence

GGATCCATGGCCTTACCAGTGACCGCCTTGCTCCTGCCGCTGGCCTTGCTGCTCCACGCCGCCAGGCCG

21. Flag gactacaaggacgacgatgacaag

22. CD19scFv

GACATCCAGATGACACAGACTACATCCTCCCTGTCTGCCTCTCTGGGAGACAGAGTCACCATCAGTTGCAGGG
CAAGTCAGGACATTAGTAAATATTTAAATTGGTATCAGCAGAAACCAGATGGAACTGTTAAACTCCTGATCTAC
CATACATCAAGATTACACTCAGGAGTCCCATCAAGGTTCAGTGGCAGTGGGTCTGGAACAGATTATTCTCTCAC
CATTAGCAACCTGGAGCAAGAAGATATTGCCACTTACTTTTGCCAACAGGGTAATACGCTTCCGTACACGTTC
GGAGGGGGGACCAAGCTGGAGATCACAGGTGGCGGTGGCTCGGGCGGTGGTGGGTCGGGTGGCGGCGGA
TCTGAGGTGAAACTGCAGGAGTCAGGACCTGGCCTGGTGGCGCCCTCACAGAGCCTGTCCGTCACATGCACT
GTCTCAGGGGTCTCATTACCCGACTATGGTGTAAGCTGGATTCGCCAGCCTCCACGAAAGGGTCTGGAGTGGC
TGGGAGTAATATGGGGTAGTGAAACCACATACTATAATTCAGCTCTCAAATCCAGACTGACCATCATCAAGGAC
AACTCCAAGAGCCAAGTTTTCTTAAAAATGAACAGTCTGCAAACTGATGACACAGCCATTTACTACTGTGCCA
AACATTATTACTACGGTGGTAGCTATGCTATGGACTACTGGGGCCAAGGAACCTCAGTCACCGTCTCCTCA

23. CD8/Hinge/Transmembrane Sequence

ACCACGACGCCAGCGCCGCGACCACCAACACCGGCGCCCACCATGGCTAGCCAGCCCCTGTCCCTGCGCCC
AGAGGCGTGCCGGCCAGCGGCGGGGGGCGCAGTGCACACGAGGGGGCTGGACTTCGCCTGTGATATCTAC
ATCTGGGCGCCCTTGGCCGGGACTTGTGGGGTCCTTCTCCTGTCACTGGTTATCACCCTTTACTGC

AGAGTGAAGTTCAGCAGGAGCGCAGACGCCCCCGCGTACAAGCAGGGCCAGAACCAGCTCTATAACGAGCT
CAATCTAGGACGAAGAGAGGAGTACGATGTTTTGGACAAGAGACGTGGCCGGGACCCTGAGATGGGGGGA
AAGCCGAGAAGGAAGAACCCTCAGGAAGGCCTGTACAATGAACTGCAGAAAGATAAGATGGCGGAGGCCT
ACAGTGAGATTGGGATGAAAGGCGAGCGCCGGAGGGGCAAGGGGCACGATGGCCTTTACCAGGGTCTCAG
TACAGCCACCAAGGACACCTACGACGCCCTTCACATGCAGGCCCTGCCCCCTCGCTAA

25. Woodchuck/PRE

Atcaacctctggattacaaaatttgtgaaagattgactggtattcttaactatgttgctccttttacgctatgtggatacgctgcttaatgccttg
tatcatgctattgcttcccgtatggcttcatttctcctccttgtataaatcctggttgctgtctcttatgaggagttgtggcccgttgtcaggcaa
cgtggcgtggtgtgcactgtgtttgctgacgcaaccccactggttgggggcattgccaccacctgtcagctccttccgggacttcgctttccc
cctccctattgccacggcggaactcatcgccgcctgccttgcccgctgctggacaggggctcggctgttgggcactgacaattccgtggtgt
tgtcggggaagctgacgtcctttccatggctgctcgcctgtgttgccacctggattctgcgcgggacgtccttctgctacgtcccttcggccctc
aatccagcggaccttccttcccgcggcctgctgccggctctgcggcctcttccgcgtcttcgccttcgcctcagacgagtcggatctccctttg
ggccgcctccccgcctg 26. R/region GGGTCTCTCTGGTTAGACCAGATCTGAGCCTGGGAGCTCTCTGGCTAACTAGGGAACCCACTGCTTAAGCCTC
AATAAAGCTTGCCTTGAGTGCTTCA

[FIG. 8]
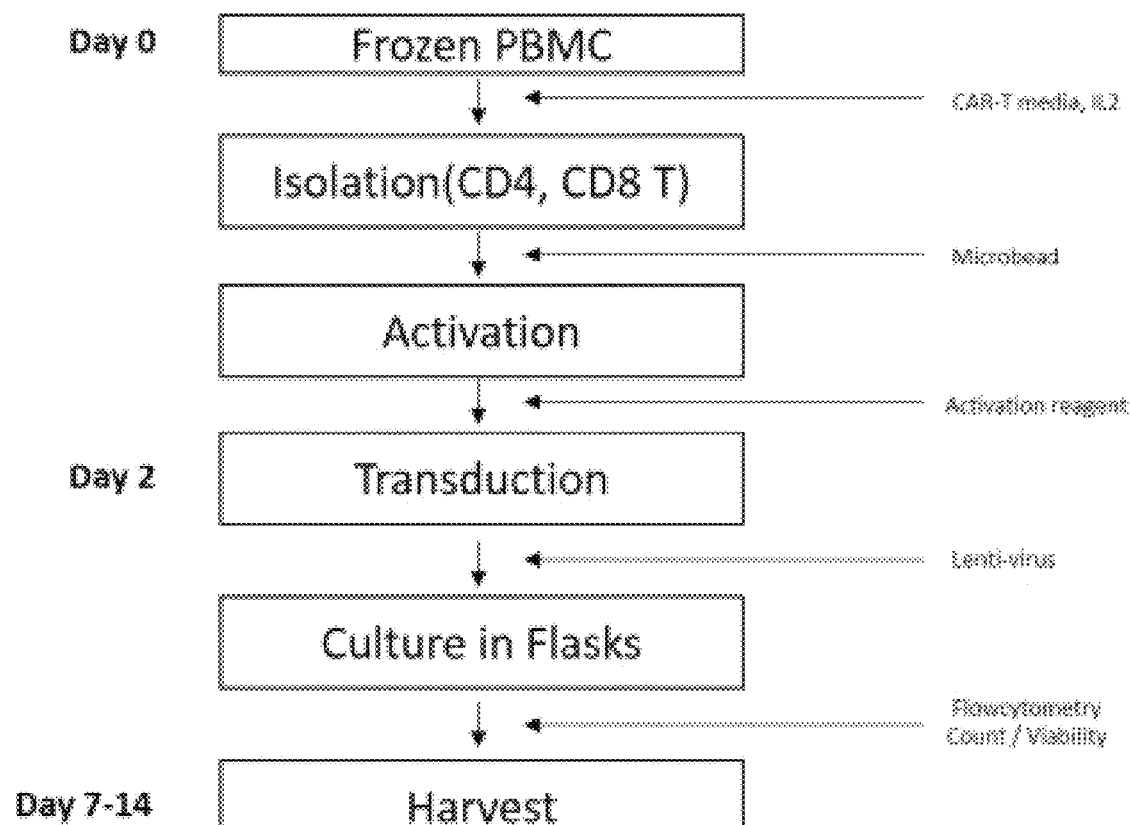
MVR CAR-T Cell Production Process

[FIG. 9]
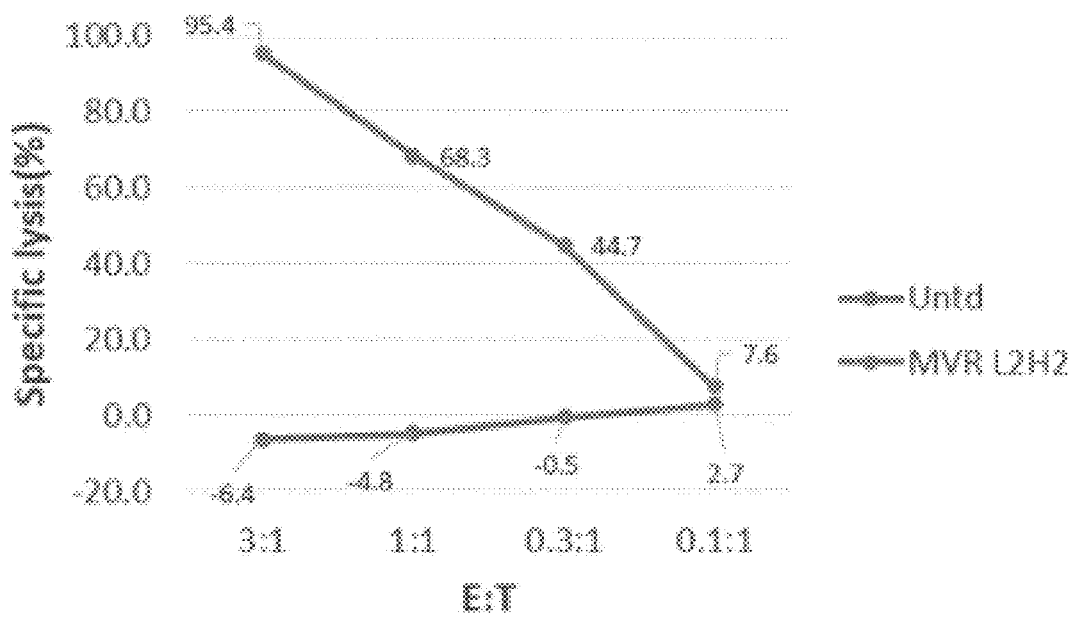

[FIG. 10]
A. CAR expression (Day 14)
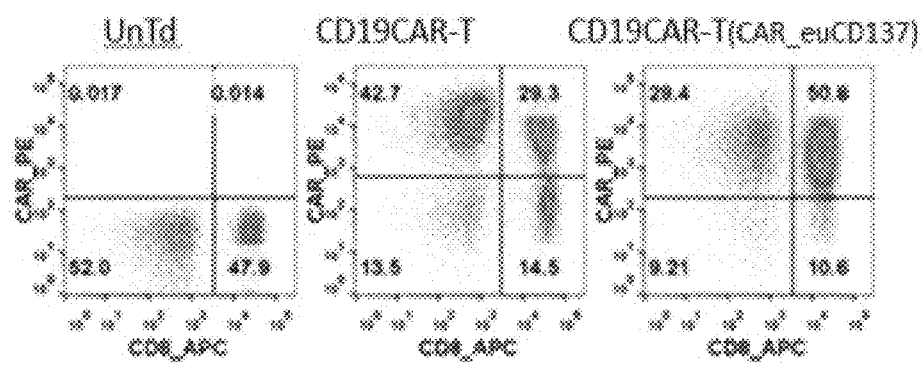
B. Killing activity (4 hr)
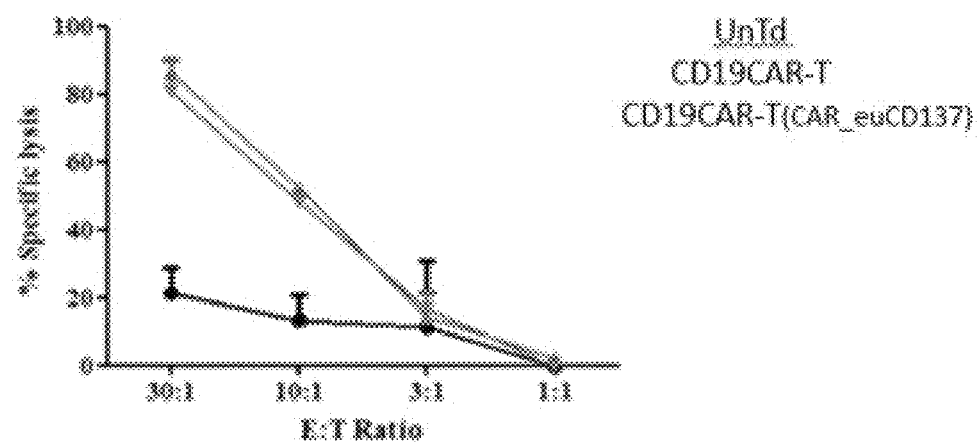

[FIG. 11]
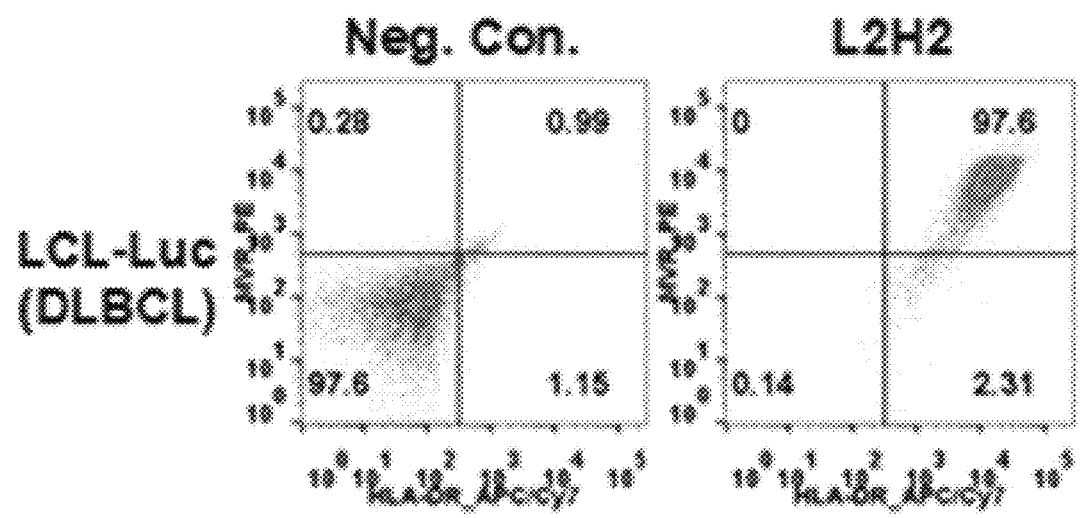

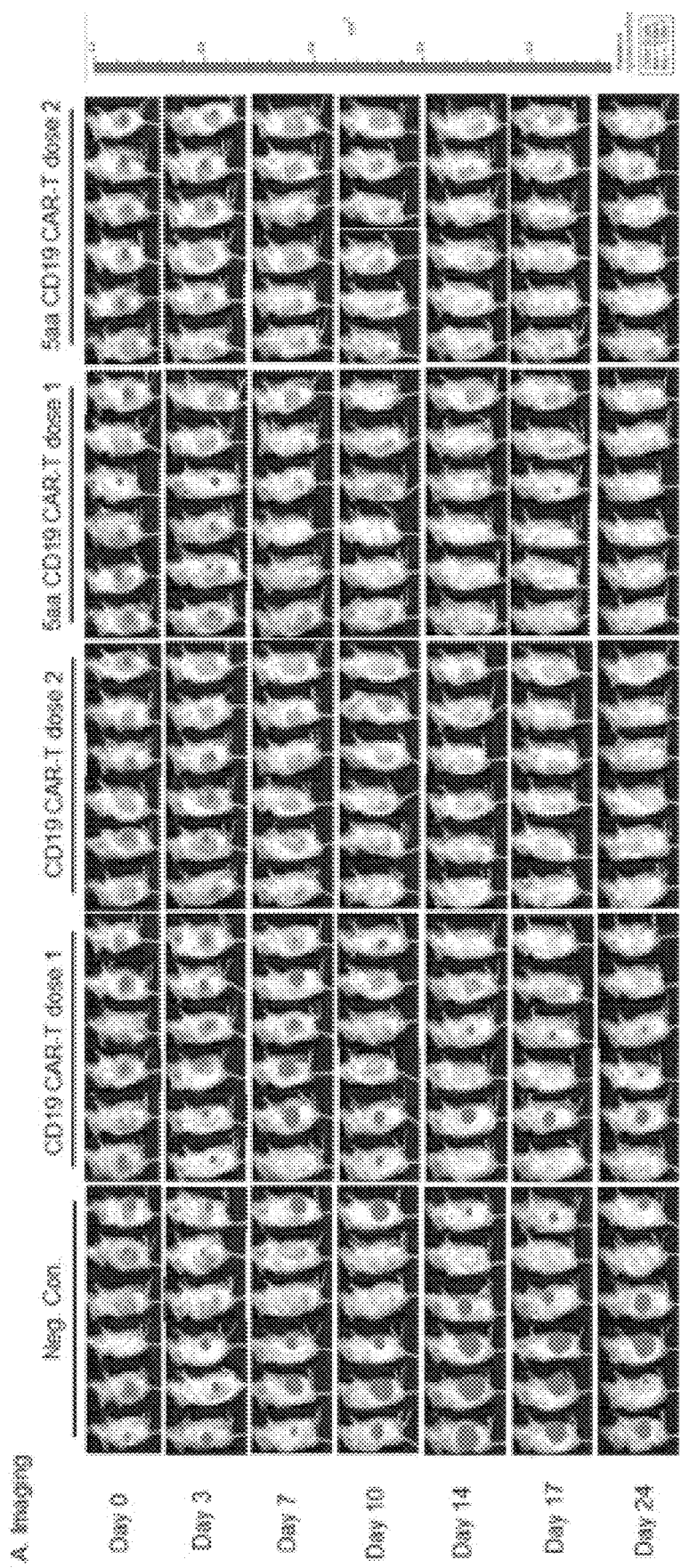
[FIG. 12a]

[FIG. 12b]
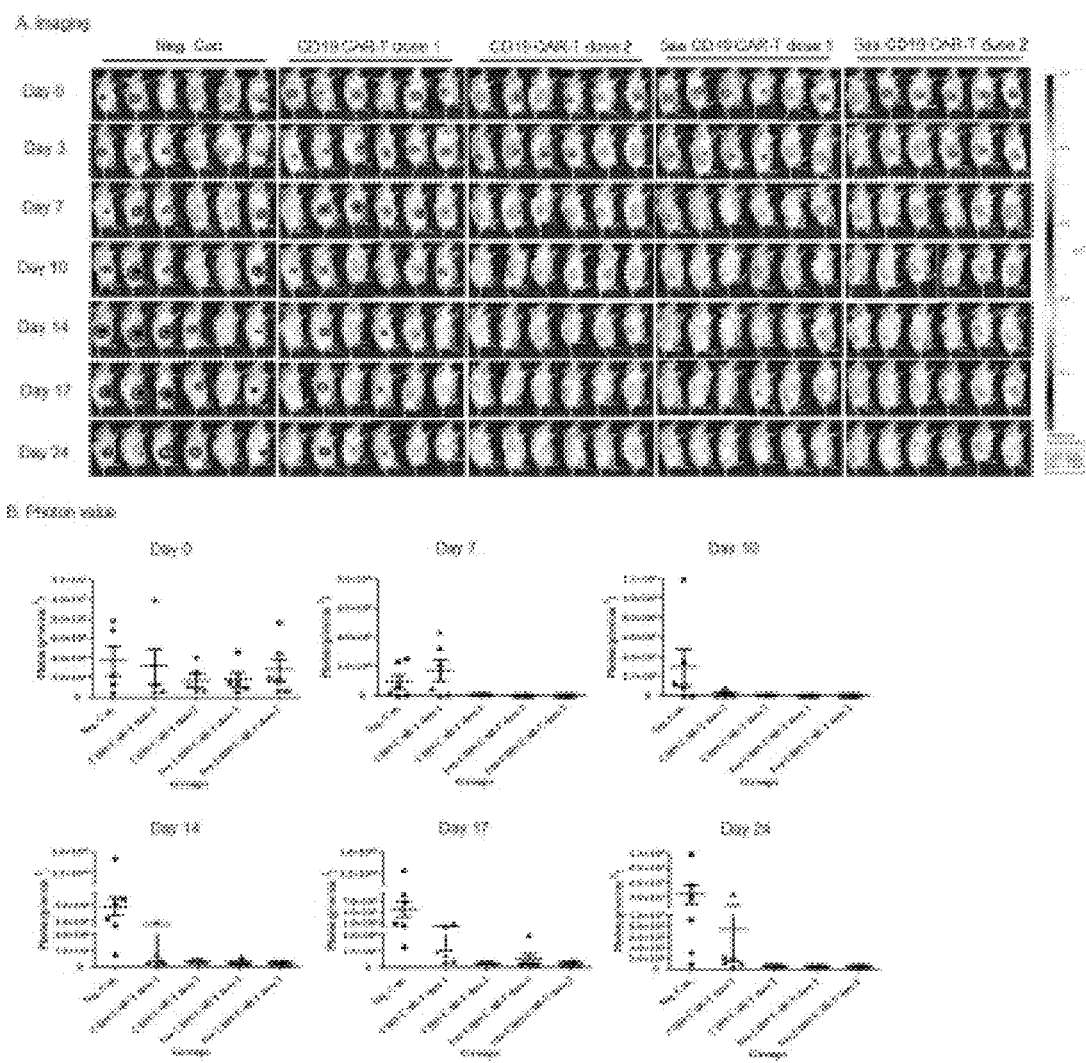

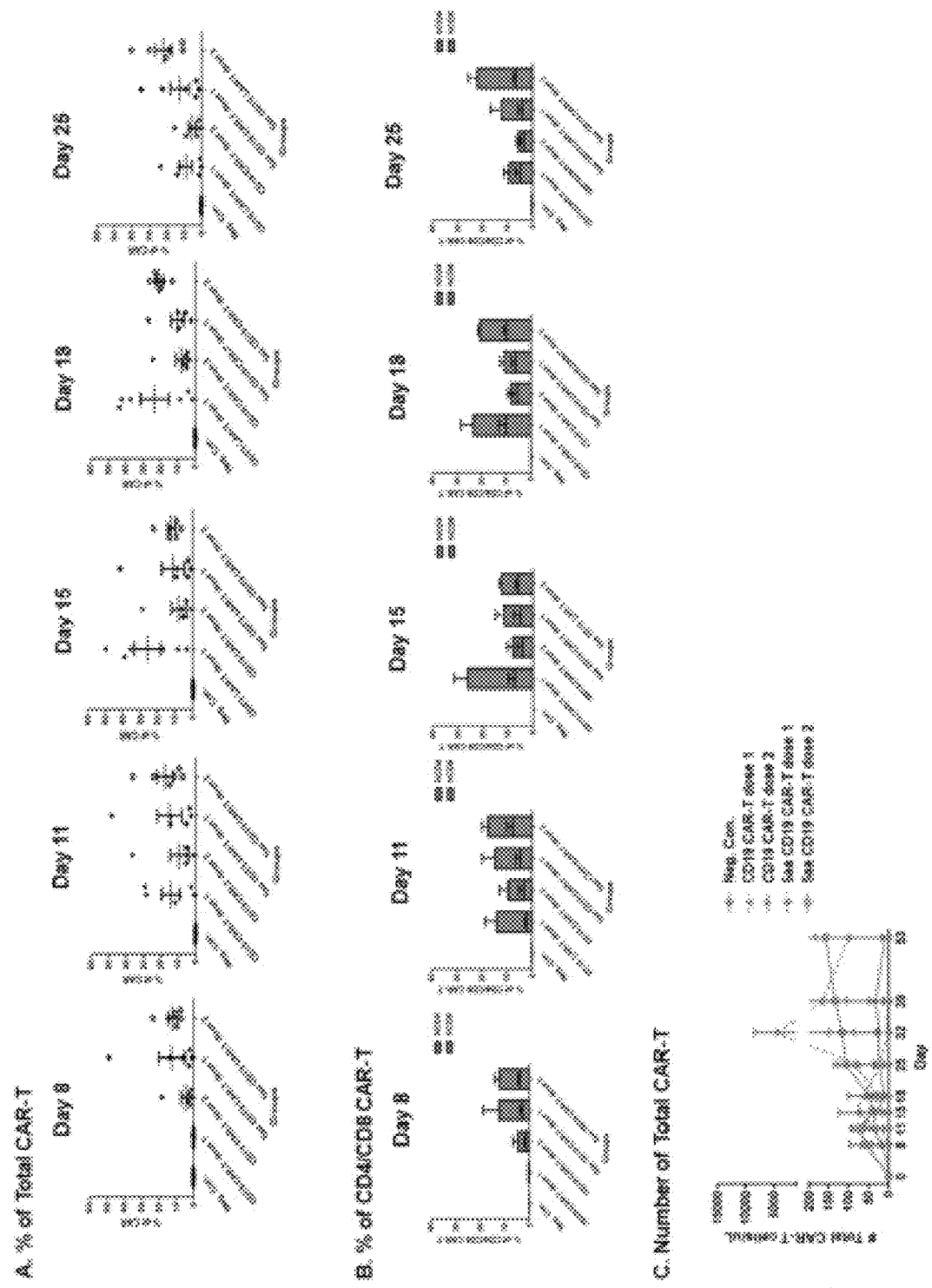
[FIG. 13]

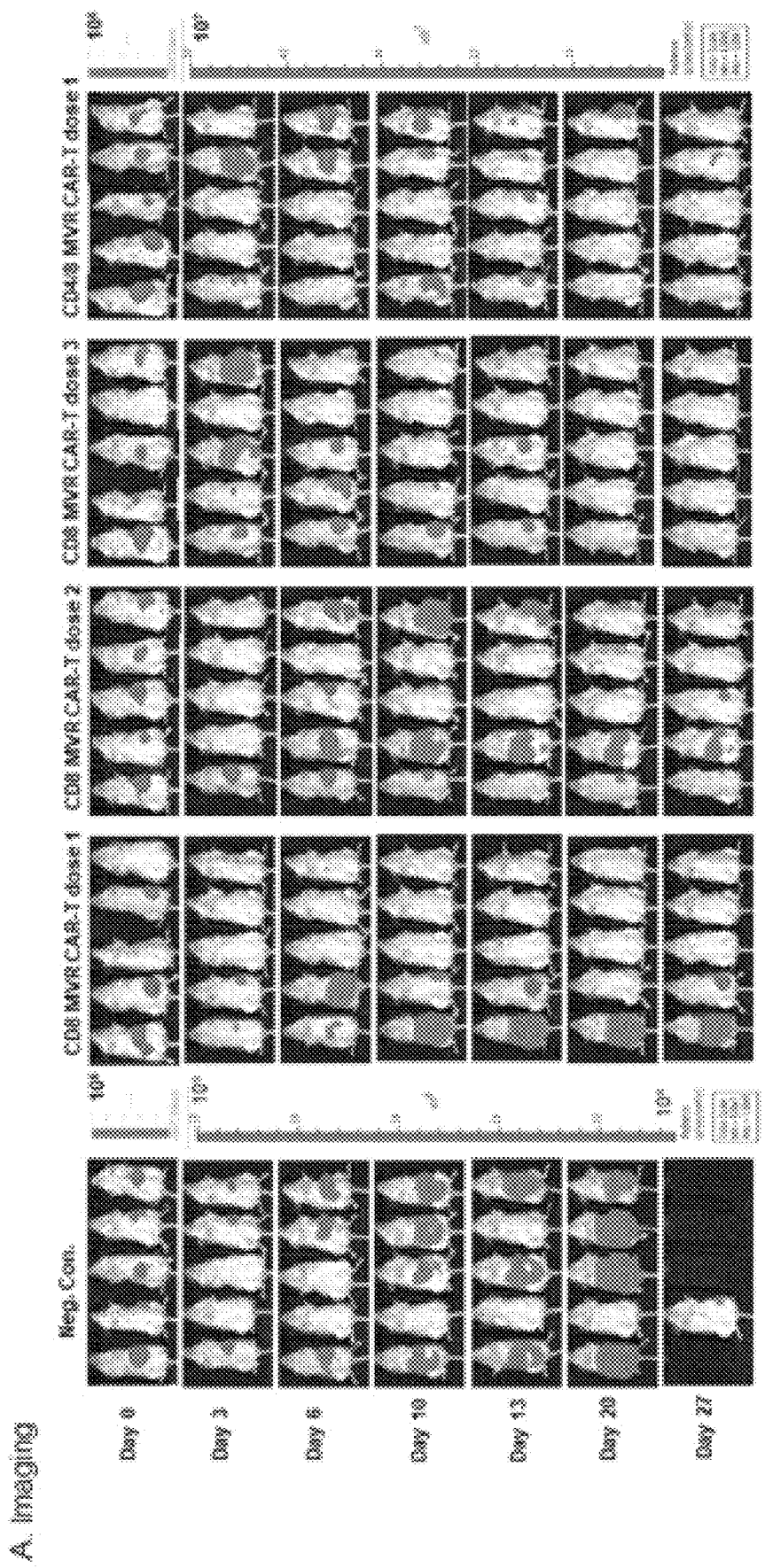

[FIG. 14b]
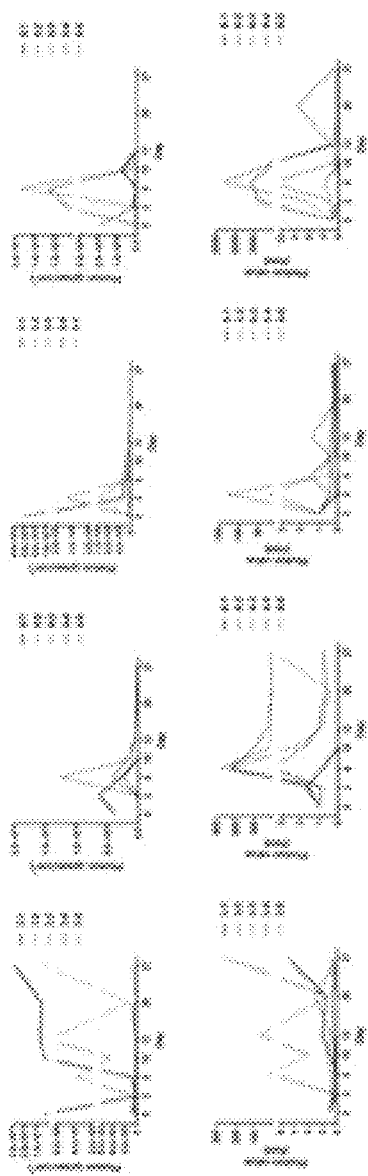
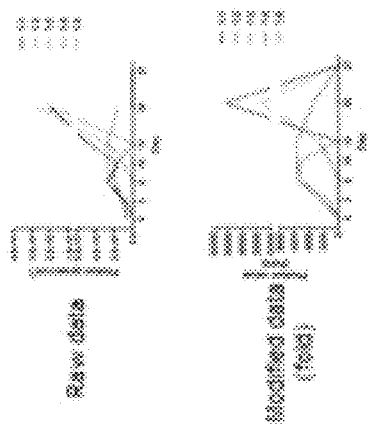

[FIG. 15a]
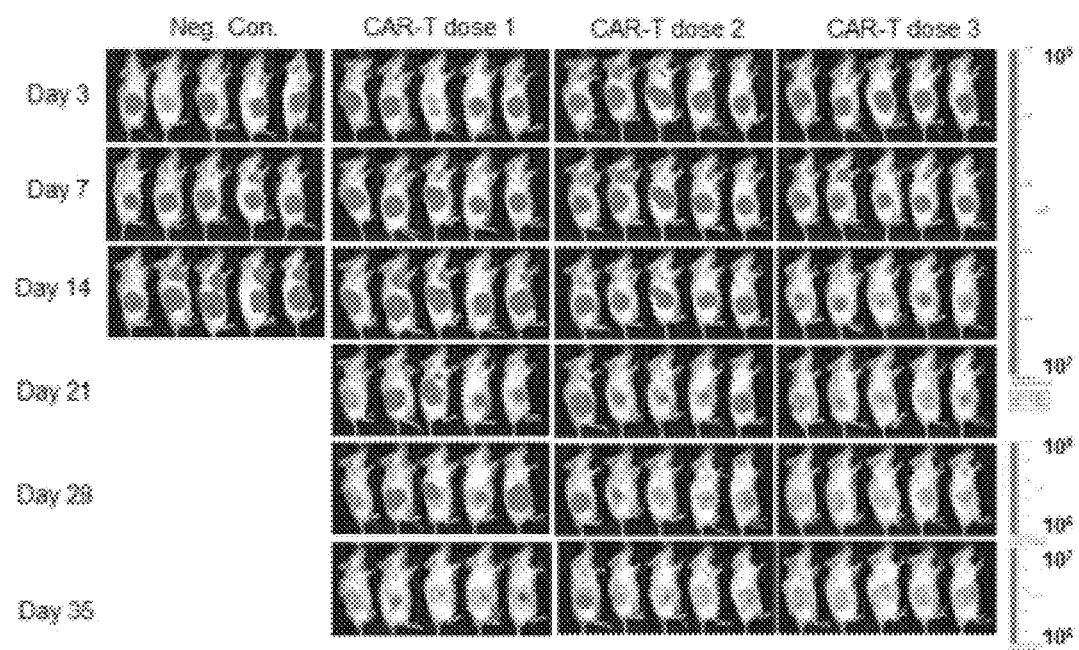

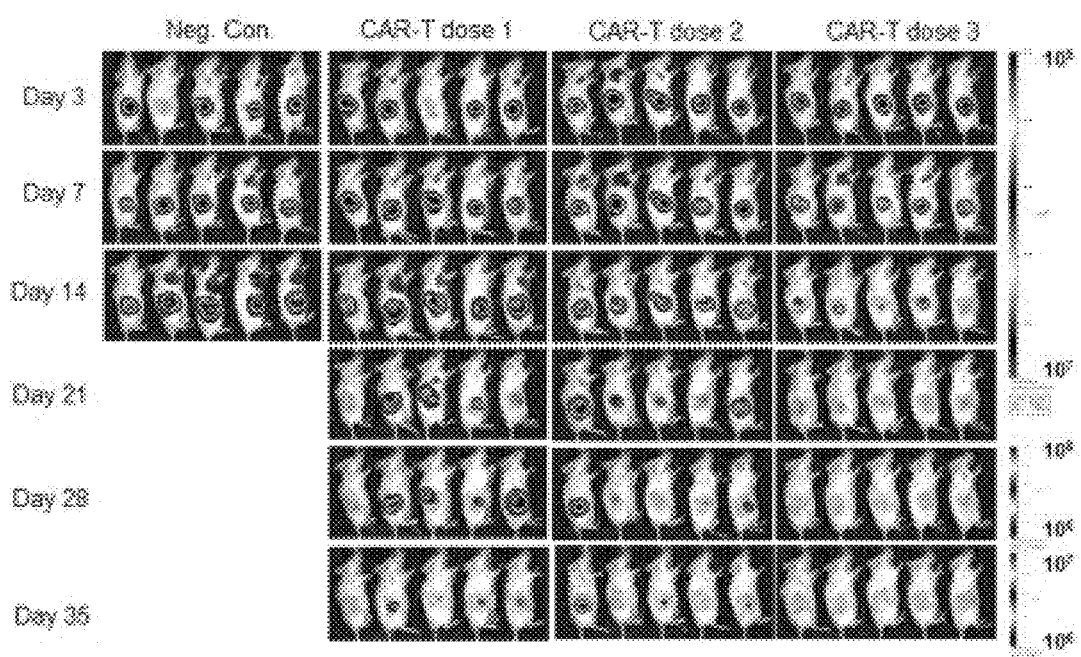
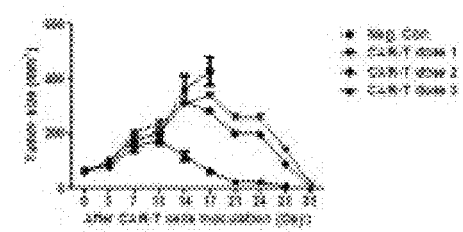
[FIG. 15b]

[FIG. 16]
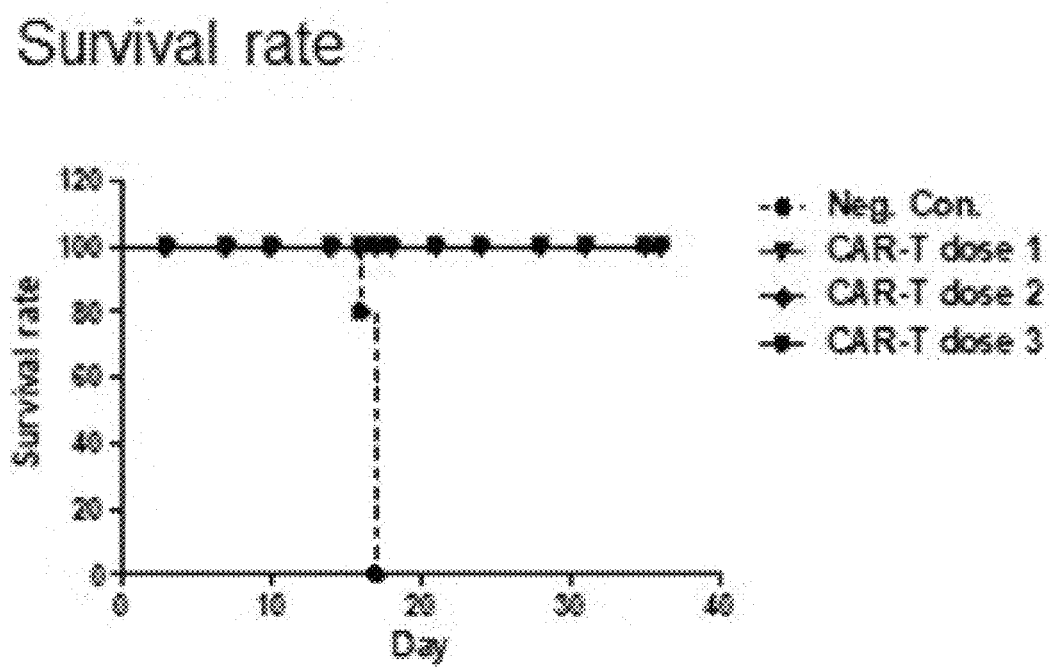

[FIG. 17]
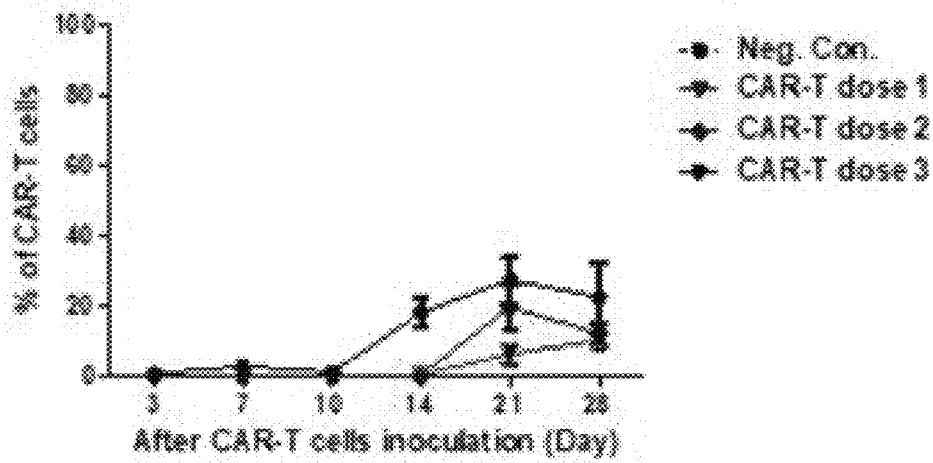
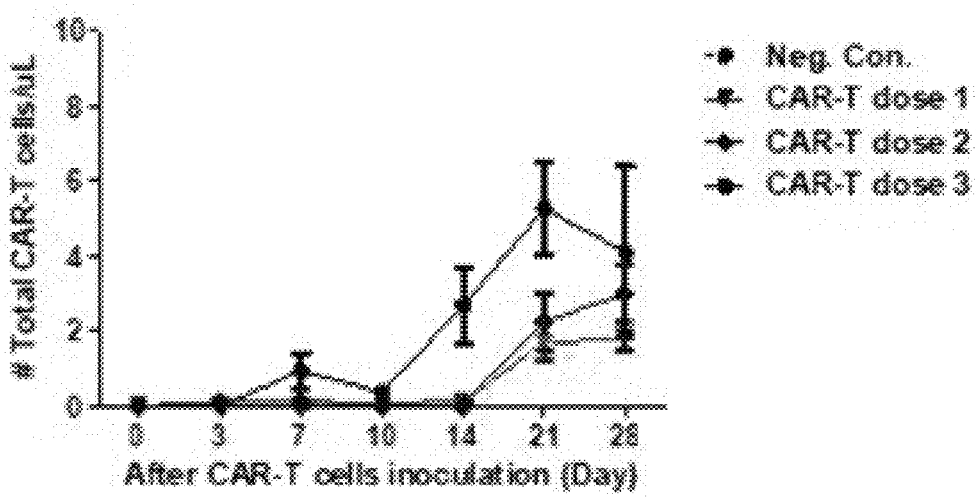

SEQUENCE LISTING

<160> NUMBER OF SEQ ID NOS: 30

<210> SEQ ID NO 1
<211> LENGTH: 5
<212> TYPE: PRT
<213> ORGANISM: Artificial
<220> FEATURE:
<223> OTHER INFORMATION: synthetic polypeptide

<400> SEQUENCE: 1

Arg Tyr Ser Val His
1               5

<210> SEQ ID NO 2
<211> LENGTH: 16
<212> TYPE: PRT
<213> ORGANISM: Artificial
<220> FEATURE:
<223> OTHER INFORMATION: synthetic polypeptide

<400> SEQUENCE: 2

Met Ile Trp Gly Gly Gly Ser Thr Asp Tyr Asn Ser Ala Leu Lys Ser
1               5                   10                  15

<210> SEQ ID NO 3
<211> LENGTH: 13
<212> TYPE: PRT
<213> ORGANISM: Artificial
<220> FEATURE:
<223> OTHER INFORMATION: synthetic polypeptide

<400> SEQUENCE: 3

Asn Glu Gly Asp Thr Thr Ala Gly Thr Trp Phe Ala Tyr
1               5                   10

<210> SEQ ID NO 4
<211> LENGTH: 11
<212> TYPE: PRT
<213> ORGANISM: Artificial
<220> FEATURE:
<223> OTHER INFORMATION: synthetic polypeptide

<400> SEQUENCE: 4

Lys Ala Ser Asp His Ile Asn Asn Trp Leu Ala
1               5                   10

```
<210> SEQ ID NO 5
<211> LENGTH: 7
<212> TYPE: PRT
<213> ORGANISM: Artificial
<220> FEATURE:
<223> OTHER INFORMATION: synthetic polypeptide

<400> SEQUENCE: 5

Gly Ala Thr Ser Leu Glu Thr
1               5

<210> SEQ ID NO 6
<211> LENGTH: 9
<212> TYPE: PRT
<213> ORGANISM: Artificial
<220> FEATURE:
<223> OTHER INFORMATION: synthetic polypeptide

<400> SEQUENCE: 6

Gln Gln Tyr Trp Ser Thr Pro Phe Thr
1               5

<210> SEQ ID NO 7
<211> LENGTH: 121
<212> TYPE: PRT
<213> ORGANISM: Artificial
<220> FEATURE:
<223> OTHER INFORMATION: synthetic polypeptide

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Arg Tyr
            20                  25                  30

Ser Val His Trp Ile Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Glu Gly Asp Thr Thr Ala Gly Thr Trp Phe Ala Tyr Trp Gly
            100                 105                 110

Gln Gly Thr Leu Val Thr Val Ser Ser
        115                 120

<210> SEQ ID NO 8
<211> LENGTH: 107
<212> TYPE: PRT
<213> ORGANISM: Artificial
<220> FEATURE:
<223> OTHER INFORMATION: synthetic polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45
```

```
Ser Gly Ala Thr Ser Leu Glu Thr Gly Val Pro Ser Arg Phe Ser Gly
     50                  55                  60

Ser Gly Ser Gly Lys Asp Tyr Thr Leu Thr Ile Ser Ser Leu Gln Pro
 65              70                  75                      80

Glu Asp Phe Ala Thr Tyr Tyr Cys Gln Gln Tyr Trp Ser Thr Pro Phe
                 85                  90                  95

Thr Phe Gly Gln Gly Thr Lys Val Glu Ile Lys
                100                 105
```

<210> SEQ ID NO 9
<211> LENGTH: 243
<212> TYPE: PRT
<213> ORGANISM: Artificial
<220> FEATURE:
<223> OTHER INFORMATION: synthetic polypeptide

<400> SEQUENCE: 9

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Asp His Ile Asn Asn Trp
             20                  25                  30

Leu Ala Trp Tyr Gln Gln Lys Pro Gly Lys Ala Pro Lys Leu Leu Ile
         35                  40                  45

Ser Gly Ala Thr Ser Leu Glu Thr Gly Val Pro Ser Arg Phe Ser Gly
     50                  55                  60

Ser Gly Ser Gly Lys Asp Tyr Thr Leu Thr Ile Ser Ser Leu Gln Pro
 65              70                  75                      80

Glu Asp Phe Ala Thr Tyr Tyr Cys Gln Gln Tyr Trp Ser Thr Pro Phe
                 85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Gly Ser Gln Val Gln Leu Gln Glu
            115                 120                 125

Ser Gly Pro Gly Leu Val Lys Pro Ser Glu Thr Leu Ser Leu Thr Cys
130                 135                 140

Thr Val Ser Gly Phe Ser Leu Ser Arg Tyr Ser Val His Trp Ile Arg
145                 150                 155                 160

Gln Pro Pro Gly Lys Gly Leu Glu Trp Leu Gly Met Ile Trp Gly Gly
                165                 170                 175

Gly Ser Thr Asp Tyr Asn Ser Ala Leu Lys Ser Arg Leu Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Arg Asn Glu Gly Asp Thr
    210                 215                 220

Thr Ala Gly Thr Trp Phe Ala Tyr Trp Gly Gln Gly Thr Leu Val Thr
225                 230                 235                 240

Val Ser Ser
```

<210> SEQ ID NO 10
<211> LENGTH: 121
<212> TYPE: PRT
<213> ORGANISM: Artificial
<220> FEATURE:
<223> OTHER INFORMATION: synthetic polypeptide

```
<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Tyr
            20                  25                  30

Ser Val His Trp Ile Arg Gln Pro Pro Gly Lys Gly Leu Glu Trp Ile
        35                  40                  45

Gly Met Ile Trp Gly Gly Gly Ser Thr Asp Tyr Asn Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asn Glu Gly Asp Thr Thr Ala Gly Thr Trp Phe Ala Tyr Trp Gly
            100                 105                 110

Gln Gly Thr Leu Val Thr Val Ser Ser
        115                 120

<210> SEQ ID NO 11
<211> LENGTH: 107
<212> TYPE: PRT
<213> ORGANISM: Artificial
<220> FEATURE:
<223> OTHER INFORMATION: synthetic polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Asp His Ile Asn Asn Trp
            20                  25                  30

Leu Ala Trp Tyr Gln Gln Lys Pro Gly Lys Ala Pro Lys Leu Leu Leu
        35                  40                  45

Tyr Gly Ala Thr Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Trp Ser Thr Pro Phe
                85                  90                  95

Thr Phe Gly Gly Gly Thr Lys Val Glu Ile Lys
            100                 105

<210> SEQ ID NO 12
<211> LENGTH: 243
<212> TYPE: PRT
<213> ORGANISM: Artificial
<220> FEATURE:
<223> OTHER INFORMATION: synthetic polypeptide

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Asp His Ile Asn Asn Trp
            20                  25                  30

Leu Ala Trp Tyr Gln Gln Lys Pro Gly Lys Ala Pro Lys Leu Leu Leu
        35                  40                  45

Tyr Gly Ala Thr Arg Leu Glu Ser Gly Val Pro Ser Arg Phe Ser Gly
    50                  55                  60
```

```
Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Trp Ser Thr Pro Phe
                 85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
        130                 135                 140

Thr Val Ser Gly Gly Ser Ile Ser Arg Tyr Ser Val His Trp Ile Arg
145                 150                 155                 160

Gln Pro Pro Gly Lys Gly Leu Glu Trp Ile Gly Met Ile Trp Gly Gly
                165                 170                 175

Gly Ser Thr Asp Tyr Asn Ser Ala Leu Lys Ser Arg Val Thr Ile Ser
            180                 185                 190

Val Asp Thr Ser Lys Asn Gln Phe Ser Leu Lys Leu Ser Ser Val Thr
        195                 200                 205

Ala Ala Asp Thr Ala Val Tyr Tyr Cys Ala Arg Asn Glu Gly Asp Thr
    210                 215                 220

Thr Ala Gly Thr Trp Phe Ala Tyr Trp Gly Gln Gly Thr Leu Val Thr
225                 230                 235                 240

Val Ser Ser

<210> SEQ ID NO 13
<211> LENGTH: 42
<212> TYPE: PRT
<213> ORGANISM: Artificial
<220> FEATURE:
<223> OTHER INFORMATION: synthetic polypeptide

<400> SEQUENCE: 13

Lys Arg Gly Arg Lys Lys Leu Leu Tyr Ile Phe Lys Gln Pro Phe Met
 1               5                  10                  15

Arg Pro Val Gln Thr Thr Gln Glu Glu Asp Gly Cys Ser Cys Arg Phe
             20                  25                  30

Pro Glu Glu Glu Glu Gly Gly Cys Glu Leu
         35                  40

<210> SEQ ID NO 14
<211> LENGTH: 47
<212> TYPE: PRT
<213> ORGANISM: Artificial
<220> FEATURE:
<223> OTHER INFORMATION: synthetic polypeptide

<400> SEQUENCE: 14

Arg Phe Ser Val Val Lys Arg Gly Arg Lys Lys Leu Leu Tyr Ile Phe
 1               5                  10                  15

Lys Gln Pro Phe Met Arg Pro Val Gln Thr Thr Gln Glu Glu Asp Gly
             20                  25                  30

Cys Ser Cys Arg Phe Pro Glu Glu Glu Glu Gly Gly Cys Glu Leu
         35                  40                  45

<210> SEQ ID NO 15
<211> LENGTH: 380
<212> TYPE: DNA
<213> ORGANISM: Artificial
```

```
<220> FEATURE:
<223> OTHER INFORMATION: synthetic oligonucleotide

<400> SEQUENCE: 15
gctgccgatt tccagaagaa gaagaaggag gatgtgaact gagagtgaag ttcagcagga      60
gcgcagacgc ccccgcgtac aagcagggcc agaaccagct ctataacgag ctcaatctag     120
gacgaagaga ggagtacgat gttttggaca agagacgtgg ccgggaccct gagatggggg     180
gaaagccgag aaggaagaac cctcaggaag gcctgtacaa tgaactgcag aaagataaga     240
tggcggaggc ctacagtgag attgggatga aggcgagcg ccggaggggc aaggggcacg      300
atggccttta ccagggtctc agtacagcca ccaaggacac ctacgacgcc cttcacatgc     360
aggccctgcc ccctcgctaa                                                 380

<210> SEQ ID NO 16
<211> LENGTH: 1412
<212> TYPE: DNA
<213> ORGANISM: Artificial
<220> FEATURE:
<223> OTHER INFORMATION: synthetic oligonucleotide

<400> SEQUENCE: 16
gatattcaga tgacccagtc cccgagctcc ctgtccgcct ctgtgggcga tagggtcacc      60
atcacctgca aggccagtga ccacatcaac aactggcctg gtatcaacag aaaccaggaa     120
aagctccgaa actactgatc agcggcgcca cctctctgga aaccggagtc ccttctcgct     180
tctctggttc cggatctggg aaggattaca ctctgaccat cagcagtctg cagccggaag     240
acttcgcaac ttattactgt cagcagtact ggtccacccc cttcaccttc ggacagggta     300
ccaaggtgga gatcaaaggc ggaggcggat ctggcggcgg aggaagtggc ggaggggat      360
ctcaggtgca gctgcaggag tcgggcccag gactggtgaa gccttcggag accctgtccc     420
tcacctgcac tgtctctggt ttctccctga gtcggtactc tgtgcattgg atccggcagc     480
ccccagggaa gggactggag tggctgggga tgatctgggg aggcggcagc accgactaca     540
acagcgccct gaagtcccga ctgaccatat caaaggacaa ctccaagaac caggtgtcct     600
tgaagctgag ctctgtgacc gctgcggaca cggccgtgta ttactgtgcg agaaatgagg     660
gcgataccac cgccggcact tggtttgcct attggggcca gggaaccctg gtcaccgtct     720
cctcaaccac gacgccagcg ccgcgaccac caacaccggc gcccaccatc gctagccagc     780
ccctgtccct gcgcccagag gcgtgccggc cagcggcggg gggcgcagtg cacacgaggg     840
ggctggactt cgcctgtgat atctacatct gggcgccctt ggccgggact tgtggggtcc     900
ttctcctgtc actggttatc acccttact gccgtttctc tgttgttaaa cggggcagaa     960
agaaactcct gtatatattc aaacaaccat ttatgagacc agtacaaact actcaagagg    1020
aagatggctg tagctgccga tttccagaag aagaagaagg aggatgtgaa ctgagagtga    1080
agttcagcag gagcgcagac gcccccgcgt acaagcaggg ccagaaccag ctctataacg    1140
agctcaatct aggacgaaga gaggagtacg atgttttgga caagagacgt ggccgggacc    1200
ctgagatggg gggaaagccg agaaggaaga accctcagga aggcctgtac aatgaactgc    1260
agaaagataa gatggcggag gcctacagtg agattgggat gaaaggcgag cgccggaggg    1320
gcaaggggca cgatgccctt taccagggtc tcagtacagc caccaaggac acctacgacg    1380
cccttcacat gcaggccctg cccctcgct aa                                   1412
```

```
<210> SEQ ID NO 17
<211> LENGTH: 1398
<212> TYPE: DNA
<213> ORGANISM: Artificial
<220> FEATURE:
<223> OTHER INFORMATION: synthetic oligonucleotide

<400> SEQUENCE: 17
gacatccaga tgacacagac tacatcctcc ctgtctgcct ctctgggaga cagagtcacc      60
atcagttgca gggcaagtca ggacattagt aaatatttaa attggtatca gcagaaacca     120
gatggaactg ttaaactcct gatctaccat acatcaagat tacactcagg agtcccatca     180
aggttcagtg gcagtgggtc tggaacagat tattctctca ccattagcaa cctggagcaa     240
gaagatattg ccacttactt ttgccaacag ggtaatacgc ttccgtacac gttcggaggg     300
gggaccaagc tggagatcac aggtggcggt ggctcgggcg gtggtgggtc gggtggcggc     360
ggatctgagg tgaaactgca ggagtcagga cctggcctgg tggcgccctc acagagcctg     420
tccgtcacat gcactgtctc aggggtctca ttacccgact atggtgtaag ctggattcgc     480
cagcctccac gaaagggtct ggagtggctg ggagtaatat ggggtagtga aaccacatac     540
tataattcag ctctcaaatc cagactgacc atcatcaagg acaactccaa gagccaagtt     600
ttcttaaaaa tgaacagtct gcaaactgat gacacagcca tttactactg tgccaaacat     660
tattactacg gtggtagcta tgctatggac tactggggcc aaggaacctc agtcaccgtc     720
tcctcaacca cgacgccagc gccgcgacca ccaacaccgg cgcccaccat cgctagccag     780
cccctgtccc tgcgcccaga ggcgtgccgg ccagcggcgg ggggcgcagt gcacacgagg     840
gggctggact cgcctgtga tatctacatc tgggcgccct tggccgggac ttgtggggtc     900
cttctcctgt cactggttat caccctttac tgcaaacggg gcagaaagaa actcctgtat     960
atattcaaac aaccatttat gagaccagta caaactactc aagaggaaga tggctgtagc    1020
tgccgatttc cagaagaaga agaaggagga tgtgaactga gagtgaagtt cagcaggagc    1080
gcagacgccc ccgcgtacaa gcagggccag aaccagctct ataacgagct caatctagga    1140
cgaagagagg agtacgatgt tttggacaag agacgtggcc gggaccctga tgggggga    1200 aagccgagaa ggaagaaccc tcaggaaggc ctgtacaatg aactgcagaa agataagatg    1260
gcggaggcct acagtgagat tgggatgaaa ggcgagcgcc ggaggggcaa ggggcacgat    1320
ggcctttacc agggtctcag tacagccacc aaggacacct cgacgcccct tcacatgcag    1380
gccctgcccc ctcgctaa                                                  1398

<210> SEQ ID NO 18
<211> LENGTH: 1420
<212> TYPE: DNA
<213> ORGANISM: Artificial
<220> FEATURE:
<223> OTHER INFORMATION: synthetic oligonucleotide

<400> SEQUENCE: 18
gacatccaga tgacacagac tacatcctcc ctgtctgcct ctctgggaga cagagtcacc      60
atcagttgca gggcaagtca ggacattagt aaatatttaa attggtatca gcagaaacca     120
gatggaactg ttaaactcct gatctaccat acatcaagat tacactcagg agtcccatca     180
aggttcagtg gcagtgggtc tggaacagat tattctctca ccattagcaa cctggagcaa     240
gaagatattg ccacttactt ttgccaacag ggtaatacgc ttccgtacac gttcggaggg     300
gggaccaagc tggagatcac aggtggcggt ggctcgggcg gtggtgggtc gggtggcggc     360
```

-continued

| | |
|---|---|
| ggatctgagg tgaaactgca ggagtcagga cctggcctgg tggcgccctc acagagcctg | 420 |
| tccgtcacat gcactgtctc aggggtctca ttacccgact atggtgtaag ctggattcgc | 480 |
| cagcctccac gaaagggtct ggagtggctg ggagtaatat ggggtagtga aaccacatac | 540 |
| tataattcag ctctcaaatc cagactgacc atcatcaagg acaactccaa gagccaagtt | 600 |
| ttcttaaaaa tgaacagtct gcaaactgat gacacagcca tttactactg tgccaaacat | 660 |
| tattactacg gtggtagcta tgctatggac tactgggggcc aaggaacctc agtcaccgtc | 720 |
| tcctcaacca cgacgccagc gccgcgacca ccaacaccgg cgcccaccat cgctagccag | 780 |
| cccctgtccc tgcgcccaga ggcgtgccgg ccagcggcgg ggggcgcagt gcacacgagg | 840 |
| gggctggact tcgcctgtga tatctacatc tgggcgccct tggccgggac ttgtggggtc | 900 |
| cttctcctgt cactggttat cacccttttac tgccgtttct ctgttgttaa cggggcagaa | 960 |
| aagaaactcc tgtatatatt caaacaacca tttatgagac cagtacaaac tactcaagag | 1020 |
| gaagatggct gtagctgccg atttccagaa gaagaagaag gaggatgtga actgagagtg | 1080 |
| aagttcagca ggagcgcaga cgcccccgcg tacaagcagg ccagaaccca gctctataac | 1140 |
| gagctcaatc taggacgaag agaggagtac gatgtttttgg acaagagacg tggccgggac | 1200 |
| cctgagatgg ggggaaagcc gagaaggaag aaccctcagg aaggcctgta caatgaactg | 1260 |
| cagaaagata gatggcggag ggcctacagt gagattggga tgaaaggcga gcgccggagg | 1320 |
| ggcaagggggc acgatggcct ttaccagggt ctcagtacag ccaccaagga cacctacgac | 1380 |
| gcccttcaca tgcaggccct gcccccctcgc taagtcgaca | 1420 |

<210> SEQ ID NO 19
<211> LENGTH: 163
<212> TYPE: DNA
<213> ORGANISM: Artificial
<220> FEATURE:
<223> OTHER INFORMATION: synthetic oligonucleotide

<400> SEQUENCE: 19

| | |
|---|---|
| gatggagttt ccccacactg agtgggtgga gactgaagtt aggccagctt ggcacttgat | 60 |
| gtaattctcc ttggaatttg ccctttttga gtttggatct tggttcattc tcaagcctca | 120 |
| gacagtggtt caaagttttt ttcttccatt tcaggtgtcg tga | 163 |

<210> SEQ ID NO 20
<211> LENGTH: 69
<212> TYPE: DNA
<213> ORGANISM: Artificial
<220> FEATURE:
<223> OTHER INFORMATION: synthetic oligonucleotide

<400> SEQUENCE: 20

| | |
|---|---|
| ggatccatgg ccttaccagt gaccgccttg ctcctgccgc tggccttgct gctccacgcc | 60 |
| gccaggccg | 69 |

<210> SEQ ID NO 21
<211> LENGTH: 24
<212> TYPE: DNA
<213> ORGANISM: Artificial
<220> FEATURE:
<223> OTHER INFORMATION: synthetic oligonucleotide

<400> SEQUENCE: 21

| | |
|---|---|
| gactacaagg acgacgatga caag | 24 |

<210> SEQ ID NO 22
<211> LENGTH: 726
<212> TYPE: DNA
<213> ORGANISM: Artificial
<220> FEATURE:
<223> OTHER INFORMATION: synthetic oligonucleotide

<400> SEQUENCE: 22

```
gacatccaga tgacacagac tacatcctcc ctgtctgcct ctctgggaga cagagtcacc     60
atcagttgca gggcaagtca ggacattagt aaatatttaa attggtatca gcagaaacca    120
gatggaactg ttaaactcct gatctaccat acatcaagat tacactcagg agtcccatca    180
aggttcagtg gcagtgggtc tggaacagat tattctctca ccattagcaa cctggagcaa    240
gaagatattg ccacttactt ttgccaacag ggtaatacgc ttccgtacac gttcggaggg    300
gggaccaagc tggagatcac aggtggcggt ggctcgggcg gtggtgggtc gggtggcggc    360
ggatctgagg tgaaactgca ggagtcagga cctggcctgg tggcgccctc acagagcctg    420
tccgtcacat gcactgtctc agggtctca ttacccgact atggtgtaag ctggattcgc    480
cagcctccac gaaagggtct ggagtggctg ggagtaatat ggggtagtga aaccacatac    540
tataattcag ctctcaaatc cagactgacc atcatcaagg acaactccaa gagccaagtt    600
ttcttaaaaa tgaacagtct gcaaactgat gacacagcca tttactactg tgccaaacat    660
tattactacg gtggtagcta tgctatggac tactggggcc aaggaacctc agtcaccgtc    720
tcctca                                                              726
```

<210> SEQ ID NO 23
<211> LENGTH: 207
<212> TYPE: DNA
<213> ORGANISM: Artificial
<220> FEATURE:
<223> OTHER INFORMATION: synthetic oligonucleotide

<400> SEQUENCE: 23

```
accacgacgc cagcgccgcg accaccaaca ccggcgccca ccatcgctag ccagcccctg     60
tccctgcgcc cagaggcgtg ccggccagcg gcggggggcg cagtgcacac gaggggggctg   120 gacttcgcct gtgatatcta catctgggcg cccttggccg ggacttgtgg ggtccttctc    180
ctgtcactgg ttatcaccct ttactgc                                       207
```

<210> SEQ ID NO 24
<211> LENGTH: 339
<212> TYPE: DNA
<213> ORGANISM: Artificial
<220> FEATURE:
<223> OTHER INFORMATION: synthetic oligonucleotide

<400> SEQUENCE: 24

```
agagtgaagt tcagcaggag cgcagacgcc cccgcgtaca agcagggcca gaaccagctc     60
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga agataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgctaa                          339
```

<210> SEQ ID NO 25
<211> LENGTH: 591
<212> TYPE: DNA
<213> ORGANISM: Artificial
<220> FEATURE:
<223> OTHER INFORMATION: synthetic oligonucleotide

<400> SEQUENCE: 25

```
atcaacctct ggattacaaa atttgtgaaa gattgactgg tattcttaac tatgttgctc      60
cttttacgct atgtggatac gctgctttaa tgcctttgta tcatgctatt gcttcccgta     120
tggctttcat tttctcctcc ttgtataaat cctggttgct gtctctttat gaggagttgt     180
ggcccgttgt caggcaacgt ggcgtggtgt gcactgtgtt tgctgacgca acccccactg     240
gttgggcat tgccaccacc tgtcagctcc tttccgggac tttcgctttc ccctcccta      300
ttgccacggc ggaactcatc gccgcctgcc ttgcccgctg ctggacaggg gctcggctgt     360
tgggcactga caattccgtg gtgttgtcgg ggaagctgac gtccttcca tggctgctcg      420
cctgtgttgc cacctggatt ctgcgcggga cgtccttctg ctacgtccct tcggccctca     480
atccagcgga ccttccttcc cgcggcctgc tgccggctct gcggcctctt ccgcgtcttc     540
gccttcgccc tcagacgagt cggatctccc tttgggccgc ctccccgcct g              591
```

<210> SEQ ID NO 26
<211> LENGTH: 98
<212> TYPE: DNA
<213> ORGANISM: Artificial
<220> FEATURE:
<223> OTHER INFORMATION: synthetic oligonucleotide

<400> SEQUENCE: 26

```
gggtctctct ggttagacca gatctgagcc tgggagctct ctggctaact agggaaccca      60
ctgcttaagc ctcaataaag cttgccttga gtgcttca                              98
```

<210> SEQ ID NO 27
<211> LENGTH: 121
<212> TYPE: PRT
<213> ORGANISM: Artificial
<220> FEATURE:
<223> OTHER INFORMATION: synthetic polypeptide

<400> SEQUENCE: 27

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Glu Met Asn Ser Leu Gln Thr Asp Asp Thr Ala Met Tyr Tyr Cys Ala
                85                  90                  95

Arg Asn Glu Gly Asp Thr Thr Ala Gly Thr Trp Phe Ala Tyr Trp Gly
            100                 105                 110

Gln Gly Thr Leu Val Thr Val Ser Ser
        115                 120
```

```
<210> SEQ ID NO 28
<211> LENGTH: 121
<212> TYPE: PRT
<213> ORGANISM: Artificial
<220> FEATURE:
<223> OTHER INFORMATION: synthetic polypeptide

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Asn Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Met Gly Ile Ala Ala Ala Gly Tyr Tyr Phe Asp Tyr Trp Gly
            100                 105                 110

Gln Gly Thr Leu Val Thr Val Ser Ser
        115                 120

<210> SEQ ID NO 29
<211> LENGTH: 107
<212> TYPE: PRT
<213> ORGANISM: Artificial
<220> FEATURE:
<223> OTHER INFORMATION: synthetic polypeptide

<400> SEQUENCE: 29

Asp Ile Gln Met Thr Gln Ser Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Phe
                85                  90                  95

Thr Phe Gly Ser Gly Thr Lys Leu Glu Ile Lys
            100                 105

<210> SEQ ID NO 30
<211> LENGTH: 107
<212> TYPE: PRT
<213> ORGANISM: Artificial
<220> FEATURE:
<223> OTHER INFORMATION: synthetic polypeptide

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30
```

```
Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65              70                  75                      80

Glu Asp Phe Ala Thr Tyr Tyr Cys Gln Gln His Tyr Thr Thr Pro Pro
                 85              90                  95

Thr Phe Gly Gln Gly Thr Lys Val Glu Ile Lys
             100             105
```

CHIMERIC ANTIGEN RECEPTOR THAT BINDS HLA-DR AND CAR-T CELL

CROSS-REFERENCE TO RELATED APPLICATIONS

This application is a continuation application claiming priority to PCT Application No. PCT/KR2019/010244, filed on Aug. 12, 2019, which claims priority to and the benefit of U.S. Patent Application No. 62/717,267, filed on Aug. 10, 2018 and U.S. Patent Application No. 62/867,503, filed on Jun. 27, 2019. The entire contents of the foregoing are incorporated by reference in their entirety.

STATEMENT REGARDING SEQUENCE LISTING

The Sequence Listing associated with this application is provided in text form in lieu of a paper copy, and is hereby incorporated by reference into the specification. The name of the text file containing the Sequence Listing is sequencelisting.txt. The text file is 29.6 KB, and was created and submitted electronically via EFS-Web on Apr. 21, 2020.

TECHNICAL FIELD

The present invention relates to chimeric antigen receptors and CAR-T cells that bind HLA-DR.

BACKGROUND ART

T cells made to express chimeric antigen receptor (CAR) have high therapeutic potential in the treatment of cancer (Grupp et al., 2013; Kochenderfer et al., 2010, 2015; Porter et al., 2011).

The clinical success of these cells is the result of the fusion structure of CARs in which various signaling domains and antigen-binding domains with various avidities are artificially bound (Maus et al., 2014; van der Stegen et al., 2015).

CAR refers to synthetic molecules based on an extracellularly-expressed antigen-binding domain that recognizes a targeted antigen, comprising a recognition site, a transmembrane domain (module), one or more co-stimulatory signaling domains, and a chimeric intracellular signal that carries an activation signal (Jensen and Riddell, 2015).

The binding of T cells having CAR with epitopes of tumor cells is not dependent on the Major Histocompatibility Complex (MHC) and may induce apoptosis and cell death of tumor cells through the mechanism of cytotoxic T cells (Ramos and Dotti, 2011).

In recent years, CAR-Ts targeting CD 19 (Cluster of Differentiation 19) have shown remarkable results in the treatment of recurrent/refractory acute lymphocytic leukemia (ALL) patients (Kochenderfer, J N et al. (2010) Blood 116: 4099-4102; Porter, D. L' et al. (2011) N. Engl. J. Med. 365: 725-733; Grupp, S A et al. (2013) N. Engl. J Med. 368: 1509-1518; Kochenderfer, J N et al. (2015) J. Clin. Oncol. 33: 540-549; Brown, C E et al. (2016) N. Engl. J. Med. 375:2561-2569).

Although CD19 CAR-T cell therapy was successful in the treatment of relapsed/refractory B cell non-Hodgkin's lymphoma, the objective response rate improved from 20-30% to 79%, with a 30-50% complete remission rate. This number is 7 times higher than previous results (Crump et al., 2016; Locke et al., 2017).

For the Malignancy Variant Receptor (MVR) used in this specification, splenocytes were isolated from Balb/c mice repeatedly immunized with human-derived B-cell lymphoma cells and hybridized with SP2/0 myeloma cells to prepare hybridoma pools, and anti-MVR hybridomas were selected from the hybridoma pool that responded specifically only to B cell lymphoma and showed high reactivity. (WO2016-094304)

CD19 is expressed in both normal and cancer cells, so the CD19 antibody cannot accurately distinguish between normal cells and cancer cells, but the MVR antibody may accurately distinguish between normal and cancer cells, thereby ensuring high therapeutic effect and safety. (Han et al., 2018).

There has been a problem that CAR-T cells are not produced from particular HLA-DR type T cells having high affinity. In order to improve this, in this patent, antibodies having various binding affinities have been prepared, and finally, an antibody suitable as a CAR-T cell therapeutic was selected.

The present invention is a patent designed to have a variety of binding affinities to the antigen through the sequence variation of the murine MVR antibody; it is expected that the antibody itself may be used as a therapeutic agent, or that it may be used in therapeutic agents using the antibody (CAR-T cell therapeutics) and the like. In addition, the antibody of the present invention, by producing a humanized antibody with a murine MVR antibody to minimize immunogenicity. In addition, by discovering antibodies having various binding affinities, CAR-T production may be expected to be superior to the parent antibody when CAR-T is applied, and may be applied to CAR-T cell therapeutics for blood cancer treatment.

DETAILED DESCRIPTION OF THE INVENTION

Problem to be Solved

An object of the present invention is to provide an MVR that may be clinically applied, and to provide CAR-T cells having an excellent therapeutic effect. Specifically, the present invention provides a co-stimulatory domain that may be introduced into various CAR-T cells as an co-stimulatory domain that plays a major role in its function in second-generation CAR-T cells. Moreover, it is an object of the present invention to provide various antigen-binding domains that are able to bind to antigens expressed on the surface of particular cancer cells and are capable of forming CAR-T cells.

Means of Solving the Problem

1. An antigen-binding molecule comprising a heavy chain variable region comprising a heavy-chain complementarity-determining region 1 (HCDR1) comprising an amino acid sequence represented by SEQ ID NO: 1, an HCDR2 comprising an amino acid sequence represented by SEQ ID NO: 2, and an HCDR3 comprising an amino acid sequence represented by SEQ ID NO: 3; a light-chain variable region comprising a light-chain complementarity-determining region 1 (LCDR1) comprising an amino acid sequence represented by SEQ ID NO: 4; an LCDR2 comprising an amino acid sequence represented by SEQ ID NO: 5; and an LCDR3 comprising an amino acid sequence represented by SEQ ID NO: 6; with the antigen-binding molecule being a chimeric antigen receptor (CAR).

2. An antigen-binding molecule according to Item 1, comprising a heavy-chain variable region represented by SEQ ID NO: 7 and a light-chain variable region represented by SEQ ID NO: 8.

3. An antigen-binding molecule according to Item 1, comprising an amino acid sequence represented by SEQ ID NO: 9.

4. An antigen-binding molecule according to Item 1, further comprising the amino acid sequence represented by SEQ ID NO: 13.

5. An antigen-binding molecule according to Item 1, further comprising the amino acid sequence represented by SEQ ID NO: 14.

6. An antigen-binding molecule according to Item 1, further comprising a transmembrane domain and an intracellular signaling domain for activating T cells.

7. An antigen-binding molecule according to Item 6, in which the said transmembrane domain is selected from the group made up of an alpha chain of a T cell receptor, a beta chain of a T cell receptor, a zeta chain of a T cell receptor, CD28, CD45, CD4, CD5, CD8, CD9, CD 16, CD22, CD33, CD37, CD64, CD80, CD86, CD 134, CD 137 and CD154, wherein the said intracellular signaling domain is a CD3zeta signaling domain and a co-stimulatory signaling domain.

8. An antigen-binding molecule according to Item 7, wherein the co-stimulatory signaling domain is selected from the group made up of CD28, OX040, CD27, ICAM-1, CD278, and CD137.

9. A nucleic acid molecule that encodes the antigen-binding molecule of any one of Items 1 to 8.

10. An expression vector comprising the nucleic acid molecule of Item 9.

11. A cell comprising the nucleic acid molecule of Item 9.

12. A cell according to Item 11 that is a T cell.

13. A cell according to Item 12, wherein the T cells are CD8+ T cells and/or CD4+ T cells.

14. A cell according to Item 11 that is a chimeric antigen receptor-modified T cell (CAR-T).

15. A pharmaceutical composition for treating cancer, comprising the cell of Item 11 as a pharmaceutically effective ingredient.

16. A pharmaceutical composition according to Item 15, wherein the cancer is esophageal adenocarcinoma, colorectal cancer, melanoma, ocular melanoma, small cell lung cancer, neuroblastoma, teratoma, fetal cancer, squamous cell carcinoma, head and neck squamous cell carcinoma, thymoma, lymphocytic leukemia, B-cell lymphoma, diffuse large B-cell lymphoma, leukemia, acute myeloid leukemia, or the like.

17. A method of treating cancer, comprising a step of administering, to a patient having cancer, a pharmaceutical composition comprising a T cell comprising a therapeutically effective quantity of the antigen-binding molecule of any of Items 1 to 8.

18. A cancer treatment method according to Item 17, in which the pharmaceutical composition either comprises CD8+ T cells, or comprises CD4+ T cells and CD8+ T cells.

19. A cancer treatment method according to Item 18, wherein the proportion of the cell counts of CD4+ T cells to CD8+ T cells is substantially 1:1.

20. An method of manufacturing a T cell with a modified chimeric antigen receptor (CAR-T) for the treatment of cancer, comprising a step of transfecting a T cell with nucleic acids that encode an antigen-binding molecule comprising a heavy chain variable region comprising a heavy-chain complementarity-determining region 1 (HCDR1) comprising an amino acid sequence represented by SEQ ID NO: 1, an HCDR2 comprising an amino acid sequence represented by SEQ ID NO: 2, and an HCDR3 comprising an amino acid sequence represented by SEQ ID NO: 3; a light-chain variable region comprising a light-chain complementarity-determining region 1 (LCDR1) comprising an amino acid sequence represented by SEQ ID NO: 4, an LCDR2 comprising an amino acid sequence represented by SEQ ID NO: 5, and an LCDR3 comprising an amino acid sequence represented by SEQ ID NO: 6; with the antigen-binding molecule being a chimeric antigen receptor (CAR).

21. A pharmaceutical composition for treating cancer, comprising as a pharmaceutically effective ingredient, T cells comprising the antigen-binding molecule according to any of Items 1 to 8.

22. A pharmaceutical composition according to Item 21, in which the pharmaceutical composition either comprises CD8+ T cells or comprises CD4+ T cells and CD8+ T cells.

23. A therapeutic pharmaceutical composition according to Item 18, in which the proportion of the cell counts of CD4+ T cells to CD8+ T cells is substantially 1:1.

Effect of the Invention

In the case of the MVR developed in the present invention, increased HLA-DR may be selectively recognized in tumor cells, and when CAR-T cells have been produced using the same, the MVR exhibits a strong in vitro efficacy and high efficacy in animals.

It also has the effect of increasing efficacy by adding five amino acids to a conventional 4-1BB co-stimulatory domain.

BRIEF DESCRIPTION OF THE DRAWINGS

FIG. 1 shows the respective VH amino acid sequence of the mouse MVR antibody (SEQ ID NO: 27) and 2 fabricated humanized antibodies (huMVR.L1H1 (SEQ ID NO: 10), huMVR.L2H2 (SEQ ID NO: 7)), as compared to reference antibody AAV40168 (SEQ ID NO: 28).

FIG. 2 shows the respective VL amino acid sequence of the mouse MVR antibody (SEQ ID NO: 29) and 2 fabricated humanized antibodies (huMVR.L1H1 (SEQ ID NO: 11), huMVR.L2H2 (SEQ ID NO: 8)), as compared to reference antibody hu4D5 (SEQ ID NO: 30).

FIG. 3 shows the result of avidity analysis of muMVR and 2 humanized antibodies (huMVR.L1H1, huMVR.L2H2).

FIG. 4 shows molecular modeling and affinity hot-spot prediction of the humanized antibody huMVR.M2H2, which is an MVR.

FIGS. 5a and 5b show the result of avidity analysis of 15 mutant types to which an affinity hot spot has been applied.

FIG. 6a is a schematic of the CD19 CAR, CD19CAR_euCD137, and huMVR.L2H2CAR_euCD137 constructs. CD19CAR utilized 214-255aa of the 4-1 (CD137) domain in the co-stimulatory domain, and CD euCD137 and huMVR.L2H2CAR_euCD137 utilized 209-255aa in the 4-1 (CD137) domain.

FIG. 6b shows the lentiviral vectors and corresponding genes showing the principal functions of CAR-T cells and the gene sequence of the CD19 CAR construct. Specifically, it shows the CD8 leader sequence including the EF1 alpha promoter, the scFv huMVR.L2H2, the CDa hinge and the human CD8 transmembrane domain, and the 4-1BB and CD3 zeta signaling domains for increasing CAR expression rate. Also shown are corresponding genes required for safe-grade lentiviral production.

FIGS. 7*a*-7*i* show the lentiviral vectors and corresponding genes showing the major functions of CAR-T cells and the gene sequence of the CD19 CAR construct. Specifically, it shows the CD8 leader sequence including the EF1 alpha promoter, the scFv MVR.L2H2, the CDa hinge and the human CD8 transmembrane domain, and the 4-1BB and CD3 zeta signaling domains for increasing CAR expression rate. Also shown are corresponding genes required for safe-grade lentiviral production.

FIG. 8 shows the MVR CAR-T cell production process.

FIG. 9 shows an experimental result confirming in vitro apoptotic function of MVR CAR-Ts.

FIG. 10 shows the production rate and efficacy evaluation for the two types of CD19 CAR-T cells into which CD19CAR and CD19CAR_euCD137 have been introduced. A: 14 days after production of the 2 CD19 CAR-Ts, the CD8 and CAR-T cells were stained, and the CAR-T production ratio obtained using FACS is shown. B: The comparison is shown of the cytotoxicity of the respective CAR-Ts, after performing a luciferase assay 4 hours after reacting 2 species of produced CAR-T with a target.

FIG. 11 shows the expression of HLA-DR in the cell line and the avidity of huMVR L2H2 scFv, using FACS, prior to evaluating the effect of huMVR CAR-T in an animal model.

FIG. 12*a* illustrates the efficacy evaluation performed in an animal model using the CAR-T cell line, after confirming the CAR-T cell production, proportion and cytotoxicity at the cell line level in FIG. 9 with results of using IVIS imaging equipment to evaluate CAR-T effectiveness after subcutaneously inducing an animal model by subcutaneously injecting a mouse with a cancer cell line expressing luciferase.

FIG. 12*b* illustrates the efficacy evaluation performed in an animal model using the CAR-T cell line, after confirming the CAR-T cell production, proportion and cytotoxicity at the cell line level in FIG. 9 with results of confirming and graphing photon values in each mouse after imaging.

FIG. 13 shows the proportion and the number of CAR-T present in the blood using FACS after performing orbital blood collection in the mouse at 3 to 4-day intervals. A: Graph confirming the total CD19 CAR-T proportion present in the blood via FACS staining of CD8+/CAR+ cells. B: Graph re-confirming the proportion of CD8 and CD4CAR-T after confirming the overall CAR-T proportion. C. Graph showing the number of CAR-T cells present in the blood by using FACS counting beads during FACS staining.

FIG. 14*a* illustrates the efficacy testing of CD8 huMVR CAR-T and CD4/CD8 huMVR CAR-T using an intraperitoneal animal model with results of IVIS imaging showing the effects of CD8 huMVR CAR-T and CD4/CD8 huMVR CAR-T after inducing animal models by injecting luciferase-expressing cancer cell lines into the mouse abdominal cavity.

FIG. 14*b* illustrates the efficacy testing of CD8 huMVR CAR-T and CD4/CD8 huMVR CAR-T using an intraperitoneal animal model with graphs showing photon values of cancer cells in the abdominal cavity-induced animal model.

FIG. 15*a* illustrates the efficacy testing of MVR CAR-T using an animal model with results of IVIS imaging showing the effect of MVR CAR-T after inducing animal models by injecting luciferase-expressing cancer cell lines into mice subcutaneously.

FIG. 15*b* illustrates the efficacy testing of MVR CAR-T using an animal model with graphs showing the size of the subcutaneously induced cancer mass after measurement with automatic calipers.

FIG. 16 is a graph showing viabilities of mice in each group based on FIG. 15.

FIG. 17 illustrates the proportion and the number of CAR-Ts present in the blood using FACS after performing orbital blood collection in the mouse at 3 to 4-day intervals after MVR CAR-T administration. A: Graph showing proportion of hCD45+/CAR+ cells in mouse blood. B: Graph showing the number of MVR CAR-T cells present in mouse blood by using FACS counting beads during FACS staining.

BEST MODE OF CARRYING OUT THE INVENTION

The present invention relates to a cell expressing a chimeric antigen receptor, a pharmaceutical composition comprising the same, and a cancer treatment method using the same.

As used in the present invention, the term "Chimeric Antigen Receptor (CAR)" refers to an antigen-binding domain that acts through a receptor that is exposed on the cell exterior that recognizes a target molecule; one or more hinge domains or spacer domains; a transmembrane domains; one or more intracellular costimulatory signaling domains; and an intracellular stimulatory domain.

As used in the present invention, the term "T cell" refers to lymphocytes derived from the thymus, and plays an important role in cell immunity. T cells encompass CD4+ T cells, CD8+ T cells, memory T cells, regulatory T cells, natural killer T cells, and the like. In one embodiment of the present invention, the T cells into which the CAR is introduced are CD8+ T cells, or CD8+ T cells and CD4+ T cells.

As used in this specification, "antibody" and "antigen-binding protein" may be used interchangeably, and the antigen-binding protein according to the present invention encompasses not only the whole antibody form but also functional fragments of the antibody molecule. The whole antibody is a structure having two full length light chains and two full length heavy chains, and each light chain is connected by a heavy chain and disulfide bond. Functional fragments of antibody molecules refer to fragments having antigen-binding function, and encompass Fab, F(ab'), F(ab')$_2$, Fv and the like. Of these antibody fragments, Fab has a single antigen binding site with a structure with a light chain, heavy-chain variable region, a light-chain constant region, and a first heavy-chain constant region (CH1). Fab' differs from Fab in that it has a hinge region comprising at least one cysteine residue at the C terminus of the heavy-chain CH1 domain. F(ab')2 antibodies are produced by forming disulfide bonds of cysteine residues in the hinge region of Fab'.

Recombinant techniques for generating Fv fragments with minimal antibody fragments in which Fv has only a heavy-chain variable region and a light-chain variable region have been disclosed in published international patent applications WO 88/10649, WO 88/106630, WO 88/07085, WO 88/07086 and WO 88/09344. Double-chain Fv (dsFv) is a disulfide bond, the heavy-chain variable region and light-chain variable region being linked, and short-chain Fv (SCFv) is generally covalently linked to the variable region of the heavy chain and the light chain through a peptide linker. Such antibody fragments may be obtained using proteolytic enzymes (for example, the entire antibody may be restricted to papain and Fab may be obtained, and cleaving pepsin may yield a F(ab')2 fragment).

In this specification, HLA-DR (Human Leukocyte Antigen-Antigen D Related) refers to a major histocompatibility complex Class II molecule (Shackelford, D A et al., (1982) Immunol. Rev. 66: 133-187). HLA-DR, which is a peptide of nine or more amino acids, and its ligand, make up a ligand for TCR. HLA-DR molecules are upregulated in response to signaling. In the case of infection, peptides (for example *Staphylococcus* enterotoxin I peptides) are bound to the DR molecule and are provided to a number of numerous T cell receptors found in helper T cells. These cells bind to B cell surface antigens that stimulate B cell proliferation.

The main function of HLA-DR is to present foreign peptide antigens that were not originally in the immune system to induce or inhibit the response of helper T cells to induce the production of antibodies to the same peptide antigen. HLA-DR is an αβ dimer and a cell surface receptor; each subunit comprises two extracellular domains, a membrane-spanning domain and a cytoplasmic tail. Both α and β chains are fixed to the cell membrane. The N-terminus domain of the mature protein forms an alpha-helix that makes up the exposed portion of the binding group, and the C-terminus cytoplasmic region interacts with other chains to form beta-sheets under the binding group across the cell membrane. Most of the peptide contact locations are at the first 80 residues of each chain.

HLA-DR is expressed to a limited extent in antigen-presenting cells such as dendritic cells, macrophages, monocytes and B cells. Because the increased abundance of DR 'antigens' at the cell surface often responds to stimuli, DR is also a marker of immune action, due to the high expression HLA-DR in cellular malignancies and limited expression spectrum in normal cells, antibodies against HLA-DR have been developed and tested for B cell malignancies in preclinical and clinical studies (Nagy, Z A, et al. (2002) Nat. Med. 8: 801-807; DeNardo, G L, et al. (2005) Clin. Cancer Res. 11: 7075s-7079s; Ivanov, A., et al. (2009) J. Clin. Invest. 119: 2143-2159; Lin, T S, et al. (2009) Leuk. Lymphoma 50: 1958-1963). Although toxicity was not severe in phase I/II testing, further research was discontinued due to limited efficacy (Lin, T. S. et al. (2009) Leuk. Lymphoma 50: 1958-1963). In view of the potential for CAR-T cells to enhance the therapeutic efficacy of monoclonal antibodies by incorporating antigen specificity into large-scale T cell responses, it is recognized that HLA-DR-directed CAR-T cells may be useful therapeutics for malignant tumors in B cells.

In one embodiment of the present invention, the antigen-binding protein comprises a scFv, and has a form in which a transmembrane domain, co-stimulatory signaling domain and intracellular signaling domain are functionally connected. For the transmembrane domain the alpha, beta or zeta chain of the T cell receptor, or one or more of CD28, CD45, CD4, CD5, CD8, CD9, CD16, CD22, CD33, CD37, CD64, CD80, CD86, CD134, CD137 or CD154, but it is not limited thereto. The intracellular signaling domain is basically a CD3zeta primary signaling domain; as a co-stimulatory signaling domain, one or more of CD28, OXO40, CD27, ICAM-1, ICOS (CD278) and 4-1BB (CD137) may be used, but it is not limited thereto. In one embodiment of the present invention, the transmembrane domain is CD8, and the co-stimulatory signaling domain is 4-1BB.

The scFv of the present invention comprises a light-chain variable region (VL) and a heavy-chain variable region (VH), and has a VL-VH or VH-VL structure, and VL and VH may be linked directly or connected by a linker. If a linker is used, a linker known in the art may be optionally used, for example, (GGGGS)$_2$, (GGGGS)$_3$, (Gly)$_6$, (Gly)$_8$, or (EAAAK)$_n$ (where n is any integer from 1 to 3), but it is not limited thereto. In one embodiment of the present invention, the antigen-binding protein comprises a VL-Linker-VH construct, and the linker is (GGGGS)$_3$.

The scFv of the antigen-binding molecule of the present invention specifically binds to an antigen presented on the cell surface; this antigen is in particular a cell surface protein that is specifically expressed in target cells, for example cancer cells, or overexpressed in cancer cells, and may for example be at least one selected from the group made up of CD30, CD20, CD19, CD22, and CD138. In one embodiment of the present invention, the antigen is HLA-DR.

In one embodiment of the present invention, the scFv is huMVR, an antibody against HLA-DR. The huMVR comprises a heavy chain variable region comprising a heavy-chain complementarity-determining region 1 (HCDR1) comprising an amino acid sequence represented by SEQ ID NO: 1, an HCDR2 comprising an amino acid sequence represented by SEQ ID NO: 2, and an HCDR3 comprising an amino acid sequence represented by SEQ ID NO: 3; a light-chain variable region comprising a light-chain complementarity-determining region 1 (LCDR1) comprising an amino acid sequence represented by SEQ ID NO: 4, an LCDR2 comprising an amino acid sequence represented by SEQ ID NO: 5, and an LCDR3 comprising an amino acid sequence represented by SEQ ID NO: 6; wherein the antigen-binding molecule is a chimeric antigen receptor (CAR). In one embodiment of the present invention, the scFv comprises a heavy-chain variable region represented by SEQ ID NO: 7 and a light-chain variable region represented by SEQ ID NO: 8; in another embodiment of the present invention, the scFv comprises an amino acid sequence represented by huMVR SEQ ID NO: 9.

The antigen-binding molecule of the present invention is a chimeric antigen receptor (CAR) having scFv as an antigen binding site; in one embodiment of the present invention, the antigen-binding molecule further comprises a transmembrane domain at the C-terminus of the scFv and an intracellular signaling domain for activating T cells.

In another embodiment of the present invention, the CAR comprises an amino acid sequence represented by SEQ ID NO: 7 or SEQ ID NO: 8. In one embodiment of the present invention, the transmembrane domain is selected from the group made up of an alpha chain of a T cell receptor, a beta chain of a T cell receptor, a zeta chain of a T cell receptor, CD28, CD45, CD4, CD5, CD8, CD9, CD 16, CD22, CD33, CD37, CD64, CD80, CD86, CD 134, CD 137 and CD154, and variants thereof, wherein the said intracellular signaling domain is a CD3zeta signaling domain and a co-stimulatory signaling domain; in one embodiment of the present invention, the co-stimulatory signaling domain is selected from the group made up of CD28, OX40, CD27, ICAM-1, CD278, and CD137.

"Isolated polypeptide", "isolated peptide", or "isolated protein" refers to a polypeptide or protein that is substantially free of compounds to which it would ordinarily bind in the natural state (for example, other proteins or polypeptides, nucleic acids, carbohydrates, lipids). "Isolated" does not mean the removal of artificial or synthetic mixtures with other compounds, the removal of impurities that do not interfere with biological activity, or the removal of impurities that may be present due for example to the addition of a stabilizer to an unfinished product or the formulation of a pharmaceutically acceptable preparation.

The term "variable region" refers to the portion of an antibody molecule that exhibits many sequence variations while performing the function of specifically binding to an antigen; CDR1, CDR2 and CDR3 are present in the variable region. "Complementarity determining regions (CDR)" are sites involved in the recognition of the antigen; these sites are important in determining the specificity of the antibody to the antigen in accordance with changes in the sequence for this site. Between the CDRs, there is a "framework region (FR)" in the proper orientation that supports the CDR rings; specifically FR1, FR2, FR3 and FR4 are present.

In one embodiment of the present invention, the other antigen-binding protein of the present invention may be a humanized antibody. In the present invention, the term "humanized antibody" refers generally to an antibody that is non-immunogenic or reduced in immunogenicity in humans, as described above. Humanized antibodies are altered antibodies, and the amino acid sequence of the antibody may be rearranged to meet the desired purpose. These possible changes are numerous and may range from changing one or a plurality of amino acids to completely reconfiguring the variable or constant region of an antibody. In general, while modification of the variable region is performed to increase the avidity and affinity of the antigen, alteration in the constant region is performed to increase intracellular action such as fixation of the complement, interaction with the membrane and the function of other effect agents. The humanized antibodies provided by the present invention may be combined with all kinds of constant regions by recombinant methods. The heavy chain constant region is gamma (γ), mu (μ), alpha (α), delta (δ) epsilon (ε) type, and subclassed as gamma 1 (γ1) gamma 2 (γ2) gamma 3 (γ3) gamma 4 (γ4) alpha1 (α1), alpha2 (α2). The constant regions of the light chains have kappa (κ) and lambda (λ) types (Coleman et al., Fundamental immunology, 2nd Ed., 1989, 55-73).

The term "fragment," as applied to polynucleotide or polypeptide sequences, refers to a nucleic acid sequence or peptide sequence that has a reduced length compared to the aforementioned nucleic acid or protein, and comprises at least a portion that is identical to the nucleotide sequence or peptide sequence of that aforementioned nucleic acid or protein. Such nucleic acid fragments and polypeptide fragments according to the present invention may, if appropriate, be comprised within larger polynucleotides or polypeptides as components thereof. Such fragments may comprise or consist of oligonucleotides or oligopeptides having continuous nucleotide or peptide sequences from a nucleic acid or protein according to the present invention, with lengths of at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000, 1500, 2000, 3000, 4000, 5000 or more.

A "variant" of a polypeptide or protein refers to any analog, fragment, derivative or mutation derived from that polypeptide or protein and retaining at least one biological property of that polypeptide or protein. Different variants of that polypeptide or protein may be present in nature. These variants may be variations of alleles characterized by different nucleotide sequences of the structural gene encoding the protein, or may comprise differentiated splicing or post-translational modifications. A skilled person may produce variants having one or a plurality of amino acid substitutions, deletions, additions or replacements. These variants may comprise: (a) a variant in which one or more amino acid residues are replaced with conservative or non-conservative amino acids, (b) a variant in which one or more amino acids are added to a polypeptide or protein, (c) a variant in which one or more of the amino acids comprises a substituent, And (d) a variant in which the polypeptide or protein is fused with another polypeptide, such as serum albumin.

Conservative variants also refer to amino acid sequences having sequence alterations that do not adversely affect the biological function of the protein. If an altered sequence interferes with or destroys a biological function associated with a protein, then the substitution, insertion or deletion is described as adversely affecting the protein. For example, the total charge, structure or hydrophobicity-hydrophilicity of a protein may be altered without adversely affecting biological activity. Accordingly, the amino acid sequence may be altered such that, for example, the peptide exhibits higher hydrophobicity or hydrophilicity without adversely affecting the protein's biological activity. Techniques for obtaining such variants, which encompass genetic (suppression, deletion, mutation, and the like), chemical and enzymatic techniques, are known to persons of ordinary skill in the art.

In one embodiment of the present invention, a nucleic acid molecule encoding the antigen-binding molecule is disclosed. The nucleic acid molecule may comprise a nucleic acid sequence encoding an amino acid sequence represented by SEQ ID NO: 7, or a nucleic acid sequence encoding an amino acid sequence represented by SEQ ID NO: 7.

In another embodiment of the present invention, the nucleic acid molecule may comprise a sequence for encoding the scFv represented by SEQ ID NO: 9. In yet another embodiment of the present invention, the nucleic acid molecule may comprise a nucleic acid sequence encoding the CAR, represented by SEQ ID NO: 15 or SEQ ID NO: 16. Moreover, in yet another embodiment of the present invention, the nucleic acid molecule may comprise a nucleic acid sequence having at least 95%, at least 96%, at least 97%, at least 98%, or at least 99% homology, for encoding a polypeptide that is the same amino acid sequence as the protein encoded by the above sequence, or that has at least 95%, at least 96%, at least 97%, at least 98%, or at least 99% homology.

The terms "nucleic acid", "nucleic acid molecule," "oligonucleotide" and "polynucleotide" in the present invention are used interchangeably, and refer to single or double-stranded forms of helices of phosphate esters of ribonucleosides (adenosine, guanosine, uridine or cytidine; "RNA molecules") or deoxyribonucleosides (deoxyadenosine, deoxyguanosine, deoxythymine or deoxycitidine; "DNA molecules"); or phosphorothioate or any phosphate ester analog such as thioester. Of these, helical DNA-DNA, DNA-RNA and RNA-RNA helices are possible. The term nucleic acid molecule, and in particular DNA or RNA molecule, refers only to the primary and secondary structures of the molecule and is not limited to any particular tertiary form. Thus, this term encompasses, from among these molecules, linear or cyclic DNA molecules (for example, restriction enzyme fragments), plasmids, supercoiled DNA and double stranded DNA found in chromosomes. In discussing the structure of a particular double-stranded DNA molecule in this specification, the structure may be described according to the general convention that the sequence is presented only in the 5' to 3' direction along the non-transcribed DNA strand (i.e., the strand with the sequence corresponding to the mRNA). "Recombinant DNA molecules" are DNA molecules that have undergone molecular-biological manipulation. DNA encompasses, but is not limited to, cDNA, genomic DNA, plasmid DNA, synthetic DNA, and semisynthetic DNA.

As is known in the art, the term "percent identity" is the relationship between two or more polypeptide sequences or two or more polynucleotide sequences, as determined by comparing sequences. In addition, in the art, the term "identity" refers, as the case may be, to the degree of sequence correspondence between polypeptide or polynucleotide sequences, as determined by the degree of matching between sequence strings. "Identity" and "similarity" may readily be calculated by known methods including but not limited to those described in Computational Molecular Biology ((Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991).

Preferred methods of determining identity are designed to provide the optimal match between the sequences tested. Methods of determining identity and similarity are codified in publicly available computer programs. Sequence alignment and percent identity calculations may be performed using sequence analysis software such as the Megaalign program of the LASERGENE bioinformatics computing suite (DNASTAR Inc., Madison, Wis.). Multiple alignment of sequences may be performed using the Clustal alignment method with default parameters (GAP PENALTY=10, GAP LENGTH PENALTY=10) (Higgins et al., CABIOS. 5: 151 (1989)). The default parameters for pairwise alignment using the Clustal method may be selected from KTUPLE 1, GAP PENALTY=3, WINDOW=5 and DIAGONALS SAVED=5. As is known in the art, "similarity" between 2 species of polypeptides is determined by comparing the amino acid sequence and the conserved amino acid substitutions of the polypeptide with the sequence of the 2nd polypeptide. Identity or homology to these sequences in the present application refers to aligning the sequences and introducing gaps as necessary to achieve maximum percent homology, without considering any conservative substitution as part of sequence identity, and is then defined as the percentage of amino acid residues in the candidate sequence that are identical to known peptides. Expansion, deletion or insertion in the peptide sequence, at the N-terminus, C-terminus or internally, should not be construed as affecting homology.

The term "homology" refers to the percent identity between two polynucleotides or two polypeptide moieties. The correspondence between sequences of one part and another part may be determined by techniques known in the art. For example, homology may be determined by aligning sequence information and the immediately comparing sequence information between two polypeptide molecules using available computer programs. Otherwise, homology may be determined by hybridizing polynucleotides under conditions that form a stable duplex between regions of the same kind, and then cleaving with a single strand-specific nuclease and sizing the cleaved fragments.

As used in this specification, all grammatical and orthographic forms of the term "homology" refers to the correspondence between proteins with "common evolutionary origin" (Reeck et al., Cell 50:667 (1987)), including proteins from a superfamily (for example, the immunoglobulin superfamily) and homologous proteins from other species (for example, myosin light chain and the like). These proteins (and the genes that encode them) have sequence homology in view of their high sequence similarity. However, in general use and in the present application, when modified with an adverb such as "very," the term "homologous" refers to sequence homology and does not indicate a common evolutionary source.

Thus, the term "sequence similarity" in all grammatical forms refers to the degree of identity or correspondence between nucleic acid or amino acid sequences that may or may not have a common evolutionary origin (Reeck et al., Cell 50:667 (1987)). In one embodiment, when about 50% (for example, at least about 75%, 90%, or 95%) of the nucleotides match a DNA sequence of a defined length or more, the two DNA sequences are "substantially homologous" or "substantially similar." Substantially homologous sequences may be identified by comparing the sequences using available standard software with a sequence data bank or, for example, Southern hybridization experiments under stringent conditions as defined for a particular system. Defining appropriate hybridization conditions is within the technical scope of the art (see, for example, Sambrook et al. 1989).

As used in this specification, "substantially similar" refers to a nucleic acid fragment in which a change in one or more nucleotide bases causes substitution of one or more amino acids but does not affect the functional properties of the protein that this DNA sequence encodes. "Substantially similar" also refers to a nucleic acid fragment in which a change in one or more nucleotide bases does not affect the ability of the nucleic acid fragment to mediate changes in gene expression by antisense or co-suppression techniques. "Substantially similar" also refers to modifications of the nucleic acid fragments of the present invention, such as deletions or insertions of one or more nucleotide bases that do not substantially affect the functional properties of the resulting transcript. Accordingly, the present invention should be understood to also encompass the particular sequences illustrated. Each of the suggested modifications is within the ordinary skill in the art, such as to determine the retention of the biological activity of the encoded product.

Furthermore, the skilled person will understand that substantially similar sequences encompassed by the present invention are defined by the ability to hybridize with the sequences illustrated in this specification under stringent conditions (0.1×SSC, 0.1% SDS, 65° C. and 0.1×SSC, 0.1% SDS after washing with 2×SSC, 0.1% SDS). Substantially similar nucleic acid fragments of the present invention are nucleic acid fragments the DNA sequences of which are at least about 70%, 80%, 90% or 95% identical to the DNA sequence of the nucleic acid fragments reported in this specification.

In one embodiment of the present invention, an expression vector is provided that comprises a nucleic acid molecule that encodes an antigen-binding protein according to the invention. The term "expression" refers to the biological production of a product encoded by a coding sequence. In most cases, the DNA sequence comprising the coding sequence is transcribed to form messenger-RNA (mRNA). The messenger RNA is then translated to form a polypeptide product having corresponding biological activity. In addition, the expression process may comprise an additional step of processing RNA transcription products (for example, splicing to remove introns), and/or post-translational processing of the polypeptide product.

As used in this specification, the term "expression vector" refers to a vector, plasmid or carrier designed to transform a host after expressing an inserted nucleic acid sequence.

The cloned genes, namely the inserted nucleic acid sequences, are generally placed under the control of regulatory elements such as promoters, minimal promoters, enhancers and the like. Countless initiation regulatory regions or promoters that are useful for inducing expression of nucleic acids in a desired host cell are well-known to persons of skill in the art. Any promoter capable of substantially inducing the expression of these genes includes but is not limited to viral promoters, bacterial promoters, animal promoters, mammalian promoters, synthetic promoters, constitutive promoters, tissue-specific promoters, pathogenesis or disease-related promoters, developmental specific promoters, inducible promoters, light regulated promoters, and the like; and include, but are not limited to, promoters containing SV40 early (SV40) promoter region and the 3'long terminus repeat (LTR) of Rous sarcoma virus (RSV); E1A of adenovirus (Ad) or major late promoters (MLP); human cytomegalovirus (HCMV) immediate early promoters; herpes simplex virus (HSV) thymidine kinase (TK) promoters; baculovirus IE1 promoters; elongation factor 1 alpha (EF1) promoters; glyceraldehyde-3-phosphate dehydrogenase (GSPDH) promoters, phosphoglycerate kinase (PGK) promoters; ubiquitin C (Ubc) promoters; albumin promoters; mouse metallothionein-L promoters and regulatory sequences of transcriptional regulatory regions; ubiquitous promoters (HPRT, vimentin, (β-actin, tubulin, etc.); intermediate filaments (desmin, neurofibrils, keratin, GFAP, and the like), promoters of therapeutic genes (MDR, CFTR or factor VIII forms and the like), onset or disease-related promoters; and promoters that have been used in transgenic animals and exhibit tissue specificity, such as gene regulatory regions for elastases that are active in pancreatic acinar cells (such as pancreatic acinar cells); insulin gene regulatory regions active in pancreatic beta cells; immunoglobulin gene regulatory regions active in lymphoid cells; mouse breast cancer virus regulatory regions active in testes, breast, lymphatic and macrophages; albumin genes active in the liver; Apo AI and Apo AII regulatory regions, alpha-fetoprotein gene regulatory regions active in the liver; alpha 1-antitrypsin gene regulatory regions active in the liver; beta-globin gene regulatory regions active in bone marrow cells; active myelin basic protein regulatory regions active in oligodendrocyte cells in the brain; myosin light chain-2 gene regulatory regions active in skeletal muscle and gonadotropic releasing hormone active in the hypothalamus; pyruvate kinase promoters; villin promoters; promoters of fatty acid binding intestinal protein; promoters of (β-actin in smooth muscle cells.

The term "vector" encompasses both non-viral and viral carriers for introducing nucleic acids into cells in vitro, ex vivo or in vivo.

The vector may be a replicon with another DNA fragment attached to amplify the attached fragment. The term "replicon" refers to any genetic element (for example a plasmid, phage, cosmid, chromosome, virus) that is able to act as an autonomous unit of in vivo DNA replication, that is, to replicate under its own control. Many vectors known in the art may be used to engineer nucleic acids, incorporate response elements and promoters into genes, and the like. Preferred vectors comprise, for example, plasmids or modified viruses comprising, for example, adenoviruses, retroviruses, adeno-associated viruses, herpes viruses, or plasmids such as PBR322 or pUC plasmid derivatives or Bluescript vectors. For example, DNA fragments corresponding to reaction elements and promoters may be inserted into appropriate vectors by combining the appropriate DNA fragments with selected vectors having complementary cohesive termini. If this is not the case, the termini of the DNA molecules may be enzymatically modified, or any site may be generated by binding the nucleotide sequence (linker) with the DNA ends. Such vectors may be manipulated so as to contain a selection marker gene for screening cells that have incorporated the marker into the cell genome. Such markers make it possible to identify and/or screen host cells expressing the protein encoded by the marker.

The vector provides the necessary regulatory sequences (for example, transcriptional and translational elements) to regulate the expression of the fusion protein in the appropriate host cell. Regulatory sequences may comprise promoter regions, enhancer regions, transcription termination sites, ribosomal binding sites, initiation codons, splice signals, introns, polyadenylation signals, Shine/Dalgarno translation sequences and Kozak consensus sequences. The regulatory sequence is selected in view of the host cell in which the fusion protein will be produced. Suitable bacterial promoters include, but are not limited to, bacteriophage λpL or pR, T6, T7, T7/lacO, lac, recA, gal, trp, ara, hut and trp-lac. Suitable eukaryotic promoters include, but are not limited to, PRBI, GAPDH, metallothionein, thymidine kinase, viral LTR, cytomegalovirus, SV40, or tissue-specific or tumor-specific promoters such as α-fetal protein, amylase, cathepsin E, M1 muscarinic receptor or γ-glutamyl transferase.

Additional vectors include lipoplexes (cationic liposome-DNA complexes), polyplexes (cationic polymer-DNA complexes) and protein-DNA complexes. In addition to nucleic acids, the vector may also comprise one or more regulatory regions and/or selectable markers useful for selecting, measuring, and monitoring the outcomes of nucleic acid delivery (delivery to a certain tissue, duration of expression, and the like).

Vectors may be introduced into a desired host cell by a method known in the art, such as injection, transfection, electroporation, microinjection, transduction, cell fusion, lipofection, calcium phosphate precipitation (Graham, F. L. et al., Virology, 52: 456 (1973); and Chen and Okayama, Mol. Cell. Biol. 7: 2745-2752 (1987)), liposome-mediated textured salt method (Wong, T. K. et al., Gene, 10:87 (1980); Nicolau and Sene, Biochim. Biophys.Acta, 721: 185-190 (1982); and Nicolau et al., Methods Enzymol., 149: 157-176 (1987)), DEAE-dextran treatment (Gopal, Mol. Cell Biol., 5: 1188-1190 (1985)), gene bombardment (Yang et al., Proc. Natl. Acad. Sci., 87: 9568-9572 (1990)) using gene species or DNA vector transporters (see, for example, Wu et al., J. Biol. Chem. 267: 963 (1992); Wu et al., J. Biol. Chem. 263: 14621 (1988); and Hartmut et al., Canadian Patent Application No. 2,012,311).

Viral vectors have been used in a wide range of gene transfer applications in cells as well as in live animal subjects. Viral vectors that may be used include, but are not limited to, adenovirus, retrovirus, vaccinia virus, poxvirus, adeno-associated virus, herpes simplex virus, lentivirus, baculovirus, sendai virus, measles virus, simian virus 40, and Epstein-Barr virus vectors. Non-viral vectors include plasmids, lipoplexes (cationic liposome-DNA complexes), polyplexes (cationic polymer-DNA complexes) and protein-DNA complexes. In addition to nucleic acids, the vector may comprise one or more regulatory regions and/or selection markers useful for screening, measuring, and monitoring nucleic acid delivery outcomes (delivery to tissue, persistence of expression, and the like).

Polynucleotides according to the present invention may be introduced in vivo by lipofection. In past decades, the use of liposomes for encapsulating and transfecting nucleic acids in vitro has increased. Synthetic cationic lipids, designed to limit the difficulties and risks encountered by liposome-mediated transfection may be used to prepare liposomes for in vivo transfection of genes (Feigner et al., Proc. Natl. Acad. Sci. USA. 84:7413 (1987); Mackey et al., Proc. Natl. Acad. Sci. USA 85:8027 (1988); and Ulmer et al., Science 259:1745 (1993)). The use of cationic lipids may promote encapsulation of negatively charged nucleic acids and may also promote fusion with negatively charged cell membranes (Feigner et al., Science 337:387 (1989)). Particularly useful lipid compounds and compositions for the delivery of nucleic acids are described in WO95/18863, WO96/17823 and U.S. Pat. No. 5,459,127. The use of lipofection to introduce exogenous genes into particular tissues in vivo has several practical advantages. Molecular targeting of liposomes to particular cells presents one area of advantage. Direct transfection to specific cell types will clearly be particularly desirable for tissues with cellular heterogeneity such as the pancreas, liver, kidney and brain. Lipids may chemically bind to other molecules for targeting (Mackey et al. 1988). Targeted peptides such as hormones or neurotransmitters, and proteins such as antibodies, or non-peptidic molecules may be chemically bound to liposomes.

As used in this specification, the term "transfection" refers to the uptake of exogenous or heterologous RNA or DNA by a cell. When exogenous or heterologous RNA or DNA is introduced into the cell, the cell is "transfected" by such RNA or DNA. When the type textured RNA or DNA causes phenotypic change, the cell is "transformed" by exogenous or heterologous RNA or DNA. The RNA or DNA that causes this transformation may be inserted (covalently) into chromosomal DNA to become part of the genome of the cell.

As used in this specification, the term "transformation" refers to the delivery of nucleic acid fragments into a host organism resulting in genetically stable inheritance. Host organisms containing transformed nucleic acid fragments are referred to as "transgenic" or "recombinant" or "transformed" organisms.

As used in the present invention, the term "recombinant vector" refers to a gene construct that is an expression vector capable of expressing a target protein in a suitable host cell, and comprises necessary regulatory elements that are operably linked so as to express the gene insert.

Other molecules, such as cationic oligopeptides (for example WO95/21931), peptides derived from DNA binding proteins (for example WO96/25508), or cationic polymers (for example WO95/21931), are also useful for facilitating the transfection of nucleic acids in vivo.

It is also possible to introduce an in vivo vector as a naked DNA plasmid (see U.S. Pat. Nos. 5,693,622, 5,589,466 and 5,580,859).

Receptor-mediated DNA delivery may also be used (Curiel et al., Hum. Gene Ther. 3: 147 (1992); and Wu et al., J. Biol. Chem. 262: 4429 (1987)).

In one embodiment of the present invention, a cell is disclosed that comprises a nucleic acid molecule that encodes an antigen-binding protein according to the invention. In one embodiment of the present invention, the cell is a T cell; in another embodiment, the T cell is a CD8+ T cell and/or a CD4+ T cell; and in another embodiment, the cell is a chimeric antigen receptor-T cell (CAR-T).

In one embodiment of the present invention, a pharmaceutical composition for cancer treatment is provided, comprising as a pharmaceutically effective ingredient a cell expressing an antigen-binding protein.

As used herein, the term "anti-cancer" encompasses "prevention" and "treatment"; "prevention" means any action in which cancer is inhibited or delayed by administration of a composition of the present invention, and "treatment" means any action that improves or beneficially alters the symptoms of cancer by administering the antibody of the present invention. The prevention may be complete, for example the complete disappearance of symptoms in the subject. The prophylaxis may also be partial, such as the occurrence of symptoms in a subject being less than would have occurred without the present invention.

The "composition" disclosed in this invention refers to a combination of the cytotoxic T cells according to the present invention as the active ingredient, and inactive ingredients such as natural or artificial carriers, labels or detectors, an active ingredients such as adjuvants, diluents, coupling agents, stabilizers, buffers, salts, lipophilic solvents, and preservatives, and comprises a pharmaceutically acceptable carrier. The carrier may also comprise pharmaceutical excipients and additional proteins, peptides, amino acids, lipids, and carbohydrates (for example, monosaccharides; disaccharides; trisaccharides; tetrasaccharides; oligosaccharides; alditol, aldonic acid, sugar-derived polysaccharides such as esterified sugar, or a sugar polymer or the like), alone or in combination, at 1 to 99.99 wt % or vol %. Protein excipients include, for example, human serum albumin, recombinant human albumin, gelatin, casein, and the like, but are not limited thereto.

Representative amino acid components that may play a buffer role include, for example, alanine, arginine, glycine, betaine, histidine, glutamic acid, aspartic acid, cysteine, lysine, leucine, isoleucine, valine, methionine, phenylalanine, aspartame, and the like, but are not limited thereto. Carbohydrate excipients also include, for example, monosaccharides such as fructose, maltose, galactose, glucose, D-mannose, sorbose; disaccharides such as lactose, sucrose, trehalose, cellobiose; polysaccharides such as raffinose, maltodextrin, dextran, and starch; and alditols such as mannitol, xylitol, maltitol, lactitol, sorbitol, and myoinositol; but are not limited thereto.

A skilled person will be able to formulate the pharmaceutical composition of the present invention by methods known in the art. For example, as required, it may be used parenterally in the form of an injection of a sterile solution or suspension with water or another pharmaceutically acceptable liquid. For example, it may be appropriately combined with pharmaceutically acceptable carriers or media, in particular sterile water or saline solution, vegetable oil, emulsifier, suspension agent, surfactant, stabilizer, excipient, vehicle, preservative, binder and the like; it may be formulated by mixing in a unit-dosage form required by generally accepted pharmaceutical practice. The active ingredient amount used in the formulation is such that a suitable dosage in the indicated range may be obtained.

In addition, sterile compositions for injection may be formulated according to conventional formulation practice using excipient liquids, such as distilled water for injection. As the aqueous solution for injection may be used, for example, combinations of physiological saline; isotonic solutions containing glucose or other auxiliary agents, for example D-sorbitol, D-mannose, D-mannitol, sodium chloride, and suitable dissolution aids, for example alcohols, in particular ethanol, and polyalcohols, for example propylene glycol, polyethylene glycol; and nonionic surfactants such as polysorbate 80 (TM), HCO-50. Oily liquids include for example sesame oil and soybean oil, and may be used in combination with benzyl benzoate and benzyl alcohol as a dissolution aid.

Injection formulations may for example be administered by intravenous injection, intraarterial injection, selective intraarterial injection, intramuscular injection, intraperitoneal injection, subcutaneous injection, intraventricular injection, intracranial injection, intramedullary injection, and the like; preferably, however, they are administered by intravenous injection.

The composition of the present invention comprises a pharmaceutically effective amount of T cells. The effective amount may be readily determined by persons of ordinary skill in the art based on the disclosure in this specification.

In general, a pharmaceutically effective amount is determined by 1st administering a low concentration of an active ingredient, and then gradually increasing the concentration until a desired effect is achieved in the subject without any side effects (for example, the symptoms associated with cancer are reduced or eliminated). Methods of determining appropriate dosages or intervals of administration for the administration of the compositions according to the present invention are described, for example, in Goodman and Gilman's The Pharmacological Basis of Therapeutics, Goodman et al., eds., 11th Edition, McGraw-Hill 2005, and Remington: The Science and Practice of Pharmacy, 20th and 21st Editions, Gennaro and University of the Sciences in Philadelphia, Eds., Lippencott Williams & Wilkins (2003 and 2005).

The method of administration of the composition according to the present invention may be determined based on various factors such as the subject's type of cancer, age, weight, sex, medical condition, severity of the disease, route of administration, and other medications administered separately. Accordingly, although the method of administration varies widely, it may be determined according to a commonly used method.

The amount of the composition according to the present invention to be administered to a subject may be determined by numerous factors such as the method of administration, subject's state of health, weight, and medical advice; all of these factors are within the scope of knowledge of a person of ordinary skill in the art.

The pharmaceutical composition according to the present invention may comprise approximately $1\times10^6$ cells/mL or more, approximately $2\times10^6$ cells/mL or more, approximately $3\times10^6$ cells/mL or more, approximately $4\times10^6$ cells/mL or more, approximately $5\times10^6$ cells/mL or more, approximately $6\times10^6$ cells/mL or more, approximately $7\times10^6$ cells/mL or more, approximately $8\times10^6$ cells/mL or more, approximately $9\times10^6$ cells/mL or more, approximately $1\times10^7$ cells/mL or more, approximately $2\times10^7$ cells/mL or more, approximately $3\times10^7$ cells/mL or more, approximately $4\times10^7$ cells/mL or more, approximately $5\times10^7$ cells/mL or more, approximately $6\times10^7$ cells/mL or more, approximately $7\times10^7$ cells/mL or more, approximately $8\times10^7$ cells/mL or more, approximately $9\times10^7$ cells/mL or more, approximately $1\times10^8$ cells/mL or more, approximately $2\times10^8$ cells/mL or more, approximately $3\times10^8$ cells/mL or more, approximately $4\times10^8$ cells/mL or more, approximately $5\times10^8$ cells/mL or more, approximately $6\times10^8$ cells/mL or more, approximately $7\times10^8$ cells/mL or more, approximately $8\times10^8$ cells/mL or more, or approximately $9\times10^8$ cells/mL or more of CAR-T cells, but a person of ordinary skill in the art will be able adjust the concentration of CAR-T cells within the range in which the same effects may be obtained. The prescription may be variously affected by factors such as formulation methods, modes of administration, patient age, weight, sex, morbidity, food, time of administration, route of administration, rate of excretion, and response sensitivity.

It may also be combined with buffers, for example phosphate buffer solutions or sodium acetate buffer solutions; analgesics, for example procaine hydrochloride; stabilizers, for example benzyl alcohol, phenols and antioxidants. The prepared injection solution is usually charged into a suitable ampoule.

Suspensions and emulsions may contain as carriers, for example, natural gums, agar, sodium alginate, pectin, methyl cellulose, carboxy methyl cellulose, or polyvinyl alcohol. Suspensions or solutions for intramuscular injection, together with the active compound, are pharmaceutically acceptable carriers such as sterile water, olive oil, ethyl oleate, glycols, for example, propylene glycol, and, if necessary, appropriate quantities of lidocaine hydrochloride.

The pharmaceutical composition according to the present invention may be administered to a subject, for example, by venous injection (bolus injection) or continuous infusion. For example, the pharmaceutical composition according to the present invention may be administered at least 1 time, at least 2 times, at least 3 times, at least 4 times, or at least 5 times, continuously, or at specified time intervals, over at least 30 minutes, at least 1 hour, at least 2 hours, at least 3 hours, at least 4 hours at least 8 hours, at least 12 hours, at least 1 day, at least 2 days, at least 3 days, at least 4 days, at least 5 days, at least 6 days, at least 7 days, at least 2 weeks, at least 3 weeks, at least 4 weeks, at least 1 month, at least 3 months, at least 6 months, or at intervals determined by clinical judgment. Injectable preparations may be formulated in ampoule form or in a unit dosage form with a multi-dose container. However, a person of ordinary skill in the art will understand that the dosage of the pharmaceutical composition according to the present invention may vary depending on various factors such as the subject's age, weight, height, sex, general medical condition and previous treatment history.

As used in the present invention, the term "cancer" refers to any of the numerous diseases or disorders caused by abnormal, uncontrolled cell growth. The cells that may cause cancer are called cancer cells, and have unique typological characteristics such as uncontrolled proliferation, immortality, metastatic potential, rapid growth and proliferation. Often, cancer cells may be in the form of a tumor, but such cells may be present individually in mammals or may be non-tumor cells, such as leukemia cells. Cancer may be detected by a clinical or radiological method for detecting the presence of tumors; by testing cells from tumors or other biological samples obtained by means such as biopsies; by detecting cancer blood markers such as CA125, PAP, PSA, CEA, AFP, HCG, CA 19-9, CA 15-3, CA 27-29, LDH, and NSE; or by detecting cancer marker genotypes such as TP53 and ATM. However, a negative finding by an above method does not necessarily mean a non-cancer diagnosis: For example, a subject who has been found to have fully recovered from cancer may still have cancer; this is confirmed in the form of a relapse.

As used in the present specification, the term "about" may be understood within the range commonly used in the art, for example, within 2 standard deviations of the mean. "About" may be understood to mean within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the mentioned value.

In the present invention, "administration" means introducing a particular substance into a patient; administration may be done in any suitable manner so that the route of administration of the composition comprising the antibody of the present invention may be administered via any general route as long as it is able to reach the target tissue. Administration may be by intraperitoneal administration, intravenous administration, intramuscular administration, subcutaneous administration, intradermal administration, oral administration, topical administration, nasal administration, pulmonary administration, or rectal administration, but is not limited thereto. However, in the case of oral administration, because the protein is digested, it is desirable to formulate the oral composition in such as way as to coat the active agent or to protect it from degradation in the stomach.

In addition, the pharmaceutical composition may be administered by any device in which the active substance is able to migrate to the target cell.

In one embodiment of the present invention, the cancer may be a solid cancer, or a blood cancer. More specifically, in one embodiment of the present invention, it is possible to treat, by means of the pharmaceutical composition according to the present invention, cancers such as esophageal adenocarcinoma, colorectal cancer, melanoma, ocular melanoma, small cell lung cancer, neuroblastoma, teratoma, fetal cancer, squamous cell carcinoma, head and neck squamous cell carcinoma, thymoma, lymphocytic leukemia, B-cell lymphoma, diffuse large B-cell lymphoma, leukemia, acute myeloid leukemia, and the like.

Another embodiment of the present invention discloses a method of treating cancer by administering the pharmaceutical composition to a patient that has cancer. The pharmaceutical composition comprises CD8+ T cells, or comprises CD4+ T cells and CD8+ T cells, or comprises both CD4+ T cells and CD8+ T cells; the proportion of CD4+ T cells and CD8+ T cells based on the number of cells is substantially 1:1.

One embodiment of the present invention discloses a method of manufacturing a T cell with a modified chimeric antigen receptor (CAR-T) for the treatment of cancer, comprising a step of infecting a T cell with nucleic acids that encode an antigen-binding molecule comprising a heavy chain variable region comprising a heavy-chain complementarity-determining region 1 (HCDR1) comprising an amino acid sequence represented by SEQ ID NO: 1, an HCDR2 comprising an amino acid sequence represented by SEQ ID NO: 2, and an HCDR3 comprising an amino acid sequence represented by SEQ ID NO: 3; a light-chain variable region comprising a light-chain complementarity-determining region 1 (LCDR1) comprising an amino acid sequence represented by SEQ ID NO: 4, an LCDR2 comprising an amino acid sequence represented by SEQ ID NO: 5, and an LCDR3 comprising an amino acid sequence represented by SEQ ID NO: 6; wherein the antigen-binding molecule is a chimeric antigen receptor (CAR).

As used in the present application, a "construct" generally refers to a composition that does not exist in nature. Constructs may be prepared by synthetic techniques (for example, production and expression of recombinant DNA), or by chemical synthesis techniques for nucleic acids or amino acids. Constructs may also be made by adding or binding one substance to another so that the result is a form that does not exist in nature.

Practical Example 1: Humanization of Mouse-Derived Anti-MVR Antibodies

Humanized antibody production of the mouse anti-MVR antibody (WO2015-133817 A1) was designed in two versions, low avidity and high avidity respectively, for use in avidity optimization.

1.1 Humanization of Heavy Chain Variable Region

To select the human antibody framework of VH for the production of humanized antibodies, Blastp (https://blast.ncbi.nlm.nih.gov/Blast.cgi?PAGE=Proteins) VH frameworks with sequences similar to mouse anti-MVR antibodies were chosen (https://www.ncbi.nlm.nih.gov/protein/AAV40168.1

Based on this, 3 CDRs of VH were defined by kabat numbering, and a combination of a selected human antibody framework and a CDR of a defined anti-MVR antibody was used to sequence a low-avidity version of VH (huMVR.H1 SEQ ID NO: 10).

In addition, a high-avidity version of VH was produced by back-mutation of VH27, VH29, VH48, VH67, VH71, VH73, VH78 from huMVR.H1 (huMVR.H2, SEQ ID NO: 7). (FIG. 1)

1.2 Humanization of Light Chain Variable Region

To select the human antibody framework of VL for the production of humanized antibodies, the VL framework of Trastzumab (U.S. Pat. No. 5,821,047 A, SEQ ID NO: 25), which is known to have excellent stability, was chosen. On this basis, 3 CDRs of VL were defined by kabat numbering, and the selected human antibody framework and the CDRs of the defined anti-MVR antibody were combined, and for the introduction of the human consensus sequence, a low-avidity version of VL was produced from the 'hu4D5 framework-anti MVR CDR combination' by mutating K to R in VL24, I to L in VL48, S to R in VL53, T to S in VL56, R to Gin VL66, F to Y in VL71, Q to G in VL100 (huMVR.L1 SEQ ID NO: 11). In addition, separately, VL49, VL69, and VL71 were mutated back from the 'hu4D5 framework-anti-MVR CDR combination', and a high-avidity version of VL was produced by mutating R to G in VL66 (huMVR.L2 SEQ ID NO: 8). (FIG. 2)

The designed humanized antibody gene is huMVR.L1H1 (huMVR.L1 & huMVR.H1) (SEQ ID NO: 10, SEQ ID NO: 11, SEQ ID NO: 12), huMVR.L2H2 (huMVR.L2 & huMVR.H2) (SEQ ID NO: 7, SEQ ID NO: 8, SEQ ID NO: 9) was produced with 2 antibodies. Specifically, two humanized antibodies were prepared in the scFv form of VL-($G_4S$)$_3$-VH in pOptivec (Invitrogen) plasmid, which is an animal cell expression vector, and a 6×His tag was conjugated to the c-terminus to prepare a gene. Plasmids into which the gene was introduced were expressed in scFv form using the Expi293 expression system (Invitrogen), and purified using AktaPure purifier (GE healthcare) and HisTrap column (GE healthcare).

Practical Example 2: Avidity Analysis for Blood Cancer Cell Lines

PBMC-derived B-cell lymphoma lymphoblastoid cell lines were prepared in FACS sample tubes (Falcon, Cat, 352052) with $1 \times 10^5$ cells per sample, and then treated with muMVR scFv, huMVR.L1H1 scFv (low binder), and huMVR.L2H2 scFv (high binder) at 0.5 μg/mL, 0.1 μg/mL, 0.05 μg/mL produced by Expi293F Cell (Invitrogen, A14527), and each sample was incubated at 4° C. for 15 minutes. After that, 3 mL of washing buffer (0.5% FBS, 0.1% sodium azide in PBS) was added to each sample tube. Each sample was centrifuged at 2000 rpm for 5 minutes, the supernatant was removed, and phycoerythrin conjugated anti-His antibody (BioLegend, Cat. 362603) was added at a 1:200 dilution proportion to reach a total volume of 200 μL. All samples were incubated at 4° C. for 15 minutes.

After that, 3 mL of washing buffer (0.5% FBS, 0.1% sodium azide in PBS) was added to each sample tube, each sample was centrifuged at 2000 rpm for 5 minutes, and the supernatant was removed. After diluting 4% Paraformaldehyde (Biosessang, P2031) to 1%, the cells were immobilized by adding 200 μL to each sample; the immobilized samples were analyzed with a FACS Celesta device (BD Biosciences).

The 2 species (huMVR.L1H1, huMVR.L2H2) of humanized antibody scFv bound to target antigens that are expressed in cells dose-dependently, and huMVR.L2H2 exhibited a similar avidity to mouse MVR scFv at an antibody concentration of 1 μg/mL, while huMVR.L1H1 exhibited very low avidity. (FIG. 3)

Practical Example 3: Affinity Hot Spot Prediction for Optimizing the Avidity of Humanized Antibodies In order to prepare mutants having various binding avidities between two humanized antibodies, an affinity hot spot was predicted based on mouse MVR antibody. Molecular modeling was carried out using Swiss-model (https://swiss-model.expasy.org/) (FIG. 4), based on the result of the avidity analysis of the two humanized antibodies, and 2 affinity hot spots in the heavy chain variable region framework (VH27, VH71) and an affinity hot spot (VL91, VL92) in the light chain variable region CDR were selected (Table 1). 15 single-mutant species of scFv type for were prepared for 4 affinity hot spots using huMVR.L2H2 as a template and expressed and purified in the same manner as described above.

TABLE 1

| Hot-Spot | Mutant Amino Acids |
|---|---|
| VH_27F | Y, L, G |
| VH_71K | H, L, V |
| VL_91Y | F, S, V, W, A |
| VL_91W | F, Y, L, A |

Practical Example 4: Avidity Analysis of 15 Mutants Applied to Mutation of Affinity Hot Spots PBMC-derived B-cell lymphoma lymphoblastoid cell lines were prepared in FACS sample tubes (Falcon, Cat, 352052) with $1\times10^5$ cells per sample, and then treated with muMVR scFv or huMVR.L2H2 produced by Expi293F Cell (Invitrogen, A14527) or 15 species of mutant at 0.1 μg/mL, and each sample was incubated at 4° C. for 15 minutes. After that, 3 mL of washing buffer (0.5% FBS, 0.1% sodium azide in PBS) was added to each sample tube. Each sample was centrifuged at 2000 rpm for 5 minutes, the supernatant was removed, and phycoerythrin conjugated anti-His antibody (BioLegend, Cat. 362603) was added at a 1:200 dilution proportion to reach a total volume of 200 μL. All samples were incubated at 4° C. for 15 minutes. After that, 3 mL of washing buffer (0.5% FBS, 0.1% sodium azide in PBS) was added to each sample tube, each sample was centrifuged at 2000 rpm for 5 minutes, and the supernatant was removed.

After diluting 4% Paraformaldehyde (Biosessang, P2031) to 1%, the cells were immobilized by adding 200 μL to each sample, and the immobilized samples were analyzed with a FACS Celesta device (BD Biosciences).

The 15 species of huMVR.L2H2 (SEQ ID NO: 9) mutant scFv exhibited various avidities to LCL cells, and of these, huMVR.L2H2.F27L, huMVR.L2H2.K71H, huMVR.L2H2.Y91F, huMVR.L2H2.Y91W, had an incrementally lower affinity than muMVR and huMVR.L2H2 (SEQ ID NO: 9) (FIG. 5).

Practical Example 5: Construction of CAR_euCD137

In the present invention, to increase immunological efficacy in the cytoplasmic signal domain 4-1BB, euCD137 (4-1BB aa209-255, SEQ ID NO: 14) to which 5 amino acids (4-1BB aa 209-213) were added in the 4-1BB cytoplasmic domain 214-255aa (SEQ ID NO: 3) used in CAR-T, as a co-stimulatory signal factor, to newly construct a CAR expression vector (CAR_euCD137) (Kwon et al., (1989) cellular immunology 121: 414-422, Kwon et al., (1998) Biochemical and biophysical research communication 242: 613-620). The completed construct comprises an anti-CD19 or huMVR.L2H2 anti-MVR binding domain, which is an scFv, including the EFI alpha promoter, a hinge region and a transmembrane domain of human CD8, and an intracellular signaling domain. In particular, the intracellular signaling domain consists of a stimulatory domain and a co-stimulatory signaling domain. For the transmembrane domain the alpha, beta or zeta chain of the T cell receptor, or one or more of CD28, CD45, CD4, CD5, CD8, CD9, CD 16, CD22, CD33, CD37, CD64, CD80, CD86, CD134, CD137 or CD154, but it is not limited thereto. Of these, the present invention used CD8. Intracellular signaling domains are basically the co-stimulatory signaling domains in the CD3zeta primary signaling domain, selected from among CD28, OX40, CD27, ICAM-1, ICOS (CD278), 4-1BB (CD 137) and 4-1BB 5aa (euCD137). The present invention used 4-1BB, a co-stimulatory signal domain to which 5 consecutive amino acids were added, to which CD3zeta was linked. The CAR gene fragment ultimately produced was conjugated to ELPS lentiviral expression vectors cleaved with BamH I and Sal I. In addition, cloning was performed using BamH I/Nhe I restriction enzyme to replace only the scFv part (FIG. 6).

In addition, a chimeric antigen receptor (huMVR CAR) was prepared comprising 2 types of cytoplasmic signal domains (4-1BB, CD3ζ) for T cell activation, using huMVR.L2H2, an MVR humanized antibody (huMVR) developed to minimize immunogenicity based on mouse MVR antibodies, which is a scFv suitable for CAR-T therapeutic development. In particular, in the present invention, in order to increase the immunological efficacy to the cytoplasmic signaling domain 4-1BB, the construct (MVR CAR_euCD137) to which 5 continuous amino acids RFSVV were added, comprises EF1 alpha promoter, and is made up not only of a scFv huMVR.L2H2 anti-MVR coupling domain, but also a CD8 hinge region and transmembrane domain, and euCD137 and intracellular signaling domain.

Practical Example 6: Recombinant huMVR Lentivirus Production

The 293T cell culture used for the production of recombinant lentiviruses contains medium comprising 10% FBS (Millipore, TMS-013-BKR) and 1× P/S (Gibco, 15140-122) in high glucose DMEM (Welgene, LM001-05). 293T cells were incubated in DMEM medium comprising 10% FBS for 24 hours prior to transduction in a 37° C. 5% $CO_2$ incubator. The next day, for transfection, the transfection reagent and four lentiviral plasmids were mixed at an appropriate proportion and incubated for 48 hours. The supernatant containing the lentivirus was then collected and centrifuged at 400×g for 10 minutes. In addition, the supernatant was filtered with a 0.45 μm syringe filter using a 50 mL syringe. The obtained supernatant was mixed 3:1 with a lentiviral enrichment kit (Clontech, 631231), and reacted at 4° C. for 24 to 48 hours. This was followed by centrifugation for 2 hours at 4° C. and 4,000 rpm to obtain a virus, which was resuspended in 0.5 mL RPMI (Welgene, LM001-01) not comprising FBS to produce a lentivirus.

6.1: Check of Number of Lentiviral Particles Infected Using Flag Conjugated to Chimeric Antigen n-Terminal Transformation units (TU/mL) were measured by analyzing the particle count of the actual transduction-capable lentiviruses using Jurkat cells. On the first day, Jurkat cells were seeded in 96-well plates at $1\times10^5$ cells/100 µL per well. On the second day, the lentivirus was serially diluted by ⅓ in 96-well plates, and the lentiviral transduction was performed on the already seeded Jurkat cells. At this time, by introducing polybrene (Millipore) into RPMI medium (10% FBS and 1× P/S), transduction of lentivirus was further increased. After centrifugation at 1200×g and 25° C. for 2 hours, the cells were incubated for 3 hours in a 37° C. 5% $CO_2$ incubator, and only 100 µL of RPMI only was added per well. On day 5, the flag of the lentivirus infected into the cell was stained with anti-Flag-DYKDDDDK (Biolegend, Cat No. 637310) to analyze the percentage of cells transduced with a flow cytometer. Using this, the titer was calculated as described in Follenzi and Naldini, 2002 (Follenzi and Naldini, 2002), and the result was found to be $1.4\times10^{10}$ TU/mL.

Practical Example 7: T Cell Thawing and Activity

Frozen peripheral blood mononuclear cells (PBMC) were thawed for 5 minutes in a 37° C. constant temperature bath and suspended with RPMI1640. Centrifugation was then performed at 1500 rpm for 5 minutes and the supernatant was removed. T cells were isolated using CD4 MicroBeads (Miltenyi Biotec, 130-045-101) and CD8 MicroBeads (Miltenyi Biotec, 130-045-201). For the method of isolating CD4, CD8 T cell, reference was made to the CD4, CD8 MicroBeads protocol (DS_130-045-101, DS_130-045-201). After bringing the cell density of the isolated cells to $1\times10^6$ cells/mL, CAR-T medium (IL Optimizer CTS basal medium+26 mL optimizer CTS+50 mL CTS immune Cell SR+10 mL penicillin streptomycin+10 mL GlutaMAX-1) was added, and IL-2 was added at 20 IU/mL. In addition, 10 µL of T cell TransAct (Miltenyi Biotec, 130-111-160) was added per $1\times10^6$ cells, placed in a T75 flask or 24-well plate, and incubated in an incubator (37° C. 5% $CO_2$) for 2 days. (FIG. 8)

Practical Example 8: CAR Transduction and CAR-T Cell Incubation

T cells activated for 2 days were added at $2\times10^6$ cells per 1 well of a 24-well plate, and a lentivirus having a CAR gene was added at a multiplicity of infection (MOI) of 1-3. Protamine sulfate (Product No. ADR301) was added and suspended to a final concentration of 10 µg/mL. The 24-well plate was centrifuged at 400×g and 32° C. for 2 h and after suspending the cells in 20 mL CAR-T medium (IL-2 200 IU/mL), they were placed in a T75 flask and incubated in an incubator (37° C. 5% $CO_2$) for 2 days. After 2 days, the cell count was taken and the cell density was brought to $0.5\times10^6$ cells/mL, and the cells were added to CAR-T medium and IL-2 was added at 200 IU/mL for the total amount of incubation broth. If the cell density was lower than $0.5\times10^6$ cells/mL, 200 IU/mL IL-2 was added relative to the total amount of culture broth, without adding CAR-T medium. After that, the cell count was taken every 2 days and CAR-T medium (IL-2 200 IU/mL) was added at a reference cell density of $0.5\times10^6$ cell/mL. The CAR-T cells were harvested between 7 and 14 days after the start of incubation (FIG. 7).

Practical Example 9: Cytotoxicity Assay

Cytotoxicity of CAR-T cells against target cells was analyzed by luciferase based assays. The target cells were infected with EBV virus carrying the luciferase gene, so as to create target cells carrying the luciferase gene. Co-culturing with effector cells was performed at an effector to target (E/T) proportion for 24 hours at 37° C. After co-culturing and then treating with CytoTox-Glo Cytotoxicity (promega, G9290) reagent, the RLU values of living target cells were measured with a Fluroskan FL microplate luminometer (Thermo).

More specifically, Triplicate was prepared in a 96-well white flat bottom plate (COSTAR, 3917), with effector cells at $4.5\times10^5$ cells/50 µL, at an E/T proportion of 3:1 based on a target cell count of $1.5\times10^4$ cells, and diluted ⅓ to prepare E/T ratios of 3:1, 1:1, 0.3:1, and 0.1:1. Into each well prepared with effector cells, $1.5\times10^4$ cells (50 µL) of target cells were co-cultured in an incubator (37° C., 5% $CO_2$) for 18-24 hours, and then 100 µL CytoTox-Glo Cytotoxicity (Promega, G9290) was added and the light was blocked, and after 5 minutes, the luminescence value was measured with a Fluroskan FL microplate luminometer (Thermo).

As a result, it was confirmed that huMVR CAR-T exhibited 95.4% cytotoxic activity at a 3:1 proportion (FIG. 8).

Practical Example 10: Cell Line Incubation

CBKLCL-Luc and KHJ LCL-Luc (hereinafter LCL-Luc) cell lines distributed by the National Cancer Center were incubated in 20% fetal bovine serum (FBS, Millipore, Cat No. TMS-013-KBR) and 1% penicillin/streptomycin (Gibco, Cat. No. 15140-122) in RPMI1640 medium (Welgene, Cat. No. LM011-01).

Practical Example 11: Verification of Two Types of CD19CAR-T Cells into which CD19CAR and CD19CAR_euCD137 were Introduced To increase immunological efficacy, CD19CAR (SEQ ID NO:17, U.S. Pat. No. 8,906,682 SEQ ID NO:12) and CD19CAR_euCD137 (SEQ ID NO:18) in which the 4-1BB domain in CD19CAR was replaced with euCD137 were separately prepared and cultured with CD19CAR-T cells in order to verify the newly-established efficacy of CAR-expressing vector (CAR_euCD137) with euCD137 (4-1BBaa209-255, SEQ ID NO:14) as a co-stimulatory signaling factor.

FACS staining was performed to confirm the production proportion of the two species of CAR-T cells after 14 days of incubation. For each CAR-T cell type, $2\times10^5$ cells were collected in FACS tubes (FALCON, Cat. No. 352052), and then 2 mL of FACS buffer was added and centrifugation was performed for 5 minutes at 2,000 rpm using a centrifuge (Thermo, ST16). After discarding the supernatant, 0.5 µL/tube anti-CD8 APC (SKI, Biolegend, Cat.No. 344722), 0.5 µL/tube anti-CD4 BV650 (RPA-T4, Biolegend, Cat. No. 300536) and 0.125 µL/tube anti-flag PE (L5, Biolegend, Cat. No. 637310) was added and staining was performed at room temperature for 30 minutes. After adding 2 mL of FACS buffer and centrifuging at 2,000 rpm for 5 minutes, this process was repeated 1 more time. for staining surviving/dead cells, 1 µL/tube 7-AAD (Biolegend, Cat. No. 420404) was added and the mixture was left for 5 minutes at room temperature and then analyzed using FACS (BD, FACSCelesta).

Prior to demonstrating in a subcutaneous animal model the effect of CD19 CAR-T using the CAR construct (CD19CAR_euCD137, SEQ ID NO: 18) wherein euCD137 (amino acid 209-255, SEQ ID NO: 14) was added to the 4-1BB domain (amino acid 214-255, SEQ ID NO: 13)

containing five amino acids, and the conventional construct (CD19CAR, SEQ ID NO: 17, U.S. Pat. No. 8,906,682 SEQ ID NO: 12), the proportion of CAR-T cells was verified using the method developed in Practical Example 2. Confirmation of the proportion of the produced CD19 CAR-T cells using FACS staining confirmed that in the case of the improved-construct CD19 CAR-T cells (5aa CD19 CAR-T) the cell ratios were CD4+/CAR+29.4%, CD8+/CAR+ 50.8%, and total CAR-T 80.2%. It was confirmed that non-construct-improved CAR-T cells (CD 19 CAR-T), the cell ratios were 42.7% for CD4+/CAR+, 29.3% for CD8+/CAR+, and 72.0% for total CAR-T.

Accordingly, it was confirmed that 5aa CD19 CAR-T cells had 8.2% higher expression of CAR than CD19 CAR-T cells, and the CD8+/CAR+ cell was 21.5%, or about 2 times as many. (FIG. 9-A)

Practical Example 12: Confirmation of Cytotoxicity of Produced CD19CAR-T Cells

To determine the cytotoxicity of the two CAR-T cell types cultured for 14 days, the CAR-T (E): LCL (T) proportion was brought to 30:1, 10:1, 3:1, and 1:1 in 96-well white plates (Corning, Cat. No. 3917). First, CAR-T cells were placed in wells at $6\times10^5$ cells/50 $2\times10^5$ cells/50 $9\times10^4$ cells/50 and $2\times10^4$ cells/50 respectively. Next, the target cell line, namely the CBK LCL-Luc cell line, was added to $2\times10^4$ cells/50 µL in a 37° C. $CO_2$ incubator (Mammert, INCO153med) and reacted for 4 hours. After 4 hours, 100 µL of Bright-Glo™ (Promega, Cat. No. E2620) was added to each well, and 5 minutes later, the relative light unit (RLU) value was measured using ELISA (Thermo, Fluorescan FL).

There was found to be no difference in cytotoxicity between CARTs in which conventional 4-1BB was introduced and CAR-T cells in which euCD137 containing five amino acids added to 4-1BB domain was introduced.

As a result of this experiment, when two CAR-T cells and CBK LCL-Luc cell lines were incubated together at a proportion of 30:1, the cytotoxicity was found to be about 80% after 4 hours, and when they were incubated at 10:1, the cytotoxicity was about 50%. As the respective number of CAR-T cells incubated with cancer cells decreased by a factor of 3, the cytotoxicity decreased by about a factor of 3; in addition, when 5 amino acids were added to the 4-1BB domain in vitro, this was confirmed not to affect the cytotoxicity. (FIG. 9B)

Practical Example 13: Confirmation of HLADR Expression and HuMVR L2112 scFv Avidity Test in Cell Lines FACS analysis was performed using the cultured LCL-Luc cell line in order to verify the expression of HLADR in the cell line and test the avidity of the developed huMVR L2H2 scFv. After transferring $2\times10^5$ cells of the LCL-Luc cell line to a FACS tube, 2 mL of FACS buffer was added and centrifuged at 2,000 rpm for 5 minutes using a centrifuge. After supernatant was discarded, there were added anti-HLADR APC-H7 (G46-6, BD Pharmigen™ Cat. No. 561358) at 0.5 µL/tube, and self-produced MVR L2H2 1.0 at µg/tube, and staining was performed at room temperature for 30 minutes. 2 mL of FACS buffer was added for washing, and centrifugation was then performed at 2,000 rpm for 5 minutes, and the supernatant was discarded. This procedure was repeated once more. For secondary staining of huMVR L2H2 scFv, 1 µL/tube of anti-His PE (Biolegend, Cat. No. 362603) was added and staining was performed for 30 minutes at room temperature. The washing process using FACS buffer was then repeated twice, and 100 µL FACS buffer was added, and analysis was then performed using FACS.

FACS staining and analysis were performed to confirm the expression of HLA DR, which is the target of huMVR L2H2, and the avidity of huMVR L2H2 scFv, in cancer cells.

Confirmation of HLA DR expression in the LCL-Luc cell line showed that 100% HLA DR was expressed. Here, when the avidity test was performed using huMVR L2H2 scFv, at least 97% binding to the expressed HLA DR was confirmed. (FIG. 10)

Practical Example 14: Induction of Subcutaneous Animal Models and Validation of CAR-T Through Automatic Caliper and IVIS Imaging For the experimental animals, NSG (NOD-scid IL2rγµL1) mice (The Jackson Laboratory) were used and managed under constant conditions in an animal nursery. The temperature was 23±2° C. with a 12 hour light/dark cycle and 50±10% humidity; feed and drink were provided ad libitum. In efficacy experiments using CD19CAR-T (5aaCD19CAR-T) with five amino acids added to the 4-1BB domain, CBK LCL-Luc cell lines were prepared at $2\times10^6$ cells/100 µL DPBS/head and injected subcutaneously in 6-week-old female mice to induce a subcutaneous animal model When the cancer size reached between 50 and 100 $mm^3$ as measured using an automatic caliper (Youngbio, TM900), improved-construct CD19 CAR-T cells and unimproved CD19 CAR-T cells at $2\times10^6$ cells/100 µL DPBS/head (dose 1) and $6\times10^6$ cells/100 µL DPBS/head (dose 2) were administered once through the tail vein to confirm efficacy. In the next experiment, the efficacy of huMVR CAR-T cells was evaluated in an animal model using the construct (huMVR CAR_euCD137, FIG. 6C) that was constructed to express huMVR in a CAR construct containing five amino acids in the 4-1BB domain. Subcutaneous animal models were induced by subcutaneously injecting LCL-Luc cells into 6-week-old female mice at $4\times10^6$ cells/100 µL DPBS/head. To confirm efficacy, when the cancer size reached the 50-100 $mm^3$ range, a single dose of MVR CAR-T was administered at $1\times10^6$ cells/100 DPBS/head, $2\times10^6$ cells/100 µL DPBS/head (dose 1) and $5\times10^6$ cells/100 µL DPBS/head (dose 3), via the tail vein. In all animal experiments, cancer size and viability were confirmed periodically.

More specifically, cancer size and photon values were measured using automatic calipers and IVIS imaging equipment (PerkinElmer, Luna III), at 3 and 4-day intervals after CAR-T administration. In the case of using TM900, the cancer size was determined after placing the equipment at the cancer site. When confirming imaging and photon values using an IVIS imaging device, 150 mg/kg XenoLight™ D-luciferin (PerkinElmer, Cat. No. 122799) was first administered intraperitoneally in mice. After 15 minutes, inhalation anesthesia was induced using isoflurane, and 5 minutes later, IVIS was used for imaging the presence of cancer cells. After imaging, normalization was performed and the luciferase values (photon values) were then confirmed and graphed.

More specifically, after constructing a subcutaneous animal model using a CBK LCL-Luc cell line, the effects of CD19 CAR-T and 5aa CD19 CAR-T cells were compared using IVIS imaging. As shown in FIG. 11A, the effect could be confirmed within 1 week after administering the 2 species of CAR-T cells.

In the experimental group in which CD19 CAR-T with CD19CAR_euCD137 was administered at $2\times10^6$ cells/100 µL DPBS/head and $6\times10^6$ cells/100 µL DPBS/head, cancer cells were observed on IVIS imaging 1 week after administration. In addition, in the group treated with non-improved-construct CD19 CAR-T, when $6\times10^6$ cells/100 µL DPBS/head was administered, cancer cells were rarely observed by imaging within 1 week of administration. However, cancer cells were identified in the experimental group administered unimproved CD19 CAR-T after 1 week.

After 1 week after CAR-T administration, as shown in imaging, the value of luciferase imaged in each subject after the imaging process was determined; luciferase values were confirmed only in the group administered CD19 CAR-T at $2\times10^6$ cells/100 DPBS/head. When observed 3 weeks or more thereafter, the tumors continued to grow in mice not administered CAR-T cells, and no cancer cells were identified in the three experimental groups in which cancer cells disappeared initially. However, after 10 days, luciferase levels were decreased in the group receiving $2\times10^6$ cells/100 µL DPBS/head for CD19 CAR-T, but cancer cells did not disappear completely after 3 weeks. When administering the improved-construct 5aa CD19 CAR-T $2\times10^6$ cells/100 µL DPBS/head, it was found via experimental imaging of cancer cells that the efficacy was similar to the group treated with CD19 CAR-T at $6\times10^6$ cells/100 µL DPBS/head. The results showed that there was no difference in cytotoxicity of 5aa CD 19 CAR-T and CD 19 CAR-T in vitro, but it was confirmed that the efficacy was 5 times better in 5aa CD19 CAR-T in animal models. (FIG. 11)

Practical Example 15: Confirmation of Proportion of CD19 CAR-T with 5 Added Amino Acids in the 4-1BB Domain in In Vivo Animal Model After CAR-T cell administration in a subcutaneous animal model to verify the potency of the improved-construct CAR-T cells, the presence of CAR-T was confirmed from mouse blood.

More specifically, orbital blood collection was performed from mice at 3 and 4-day intervals after CAR-T administration. At a time of each blood collection, 70 µL of blood was collected and 60 µL of the blood was used to confirm the proportion of the CAR-T cells and the cell count. 60 µL blood was placed in a 5 mL FACS tube, and live/dead cell staining was performed using Zombie Aqua BV510 (Biolegend, Cat. No. 423101). After reaching a concentration of 0.1 µL/100 µL DPBS/tube, staining was performed at room temperature for 10 minutes. Since counting beads (Molecularprobes, Cat. No. C36950), anti-CD45 FITC (HI30, Biolegend, Cat. No. 304006), anti-CD8 BV786 (SK-1, Biolegend, Cat. No. 344740), anti-CD4 BV650 and anti-flag PE were added and stained at room temperature for 30 minutes. Each antibody was mixed in at 0.5 µL/100 µL FACS buffer/tube, and 25 µL of counting beads were added thereto. After 30 minutes 2 mL of IX RBC lysis buffer (Biolegend, Cat. No. 422401) was added and reacted at room temperature for 5 minutes. After centrifugation for 5 minutes at 2,000 rpm using a centrifuge, all supernatant was discarded.

2 mL of FACS wash buffer was added to this tube and centrifugation was performed for 5 min at 2,000 rpm. This process was repeated one more time, and then 50 µL FACS buffer was added and analyzed using FACS.

One week after CAR-T cell administration, in the 5aa CD19 CAR-T treatment group, approximately 20% 5aa CD19 CAR-T cells were confirmed in the blood in both the $2\times10^6$ cells/100 µL DPBS/head and $6\times10^6$ cells/100 µL DPBS/head groups; but in the CD19 CAR-T-administered group, when $6\times10^6$ cells/100 µL DPBS/head was administered only 5% CD19 CAR-T was confirmed. 3 days later, the number and proportion of CAR-T cells in the mouse body reached a maximum and decreased. Within one week, in the 3 experimental groups in which CAR-T cells were identified (5aa CD19 CAR-T; $2\times10^6$ cells/100 µL DPBS/head and $6\times10^6$ cells/100 µL DPBS/head, CD19 CAR-T; $6\times10^6$ cells/100 µL DPBS/head), the cancer cells were killed quickly because it was possible for them to contact relatively many CAR-T cells before they proliferated in the mouse body. However, in the experimental group administered CD19CAR-T at $2\times10^6$ cells/100 µL DPBS/head, the proportion and number of CAR-T cells reached a maximum at 2 weeks, and the CAR-T proportion was about 25% with cancer cells proliferating relatively well. The improved-construct 5aa CD 19 CAR-T was more stable in quantity than the CD19 CAR-T, after the CAR-T proportion initially increased and later decreased. In the case of CD 19 CAR-T, however, the proportion of CAR-T cells increased and decreased at a later time, and consequently it took longer for the tumor to disappear in the mouse body. As a result, as in the results of this experiment, the group administered 5aa CD19 CAR-T at $2\times10^6$ cells/100 µL DPBS/head exhibited similar CAR-T levels and effects in mice as the group administered CD19 CAR-T at $6\times10^6$ cells/100 µL DPBS/head, indicating that 5aa CD19 CAR-T has a superior effect. (FIG. 12)

Practical Example 16: Induction of Intraperitoneal Animal Model and Evaluation of Efficacy of CD8 and CD4/CD8 huMVR CAR-T (CAR_euCD137) in Intraperitoneal Animal Model The experimental animals used to induce the intraperitoneal animal model were the same as the animals used in Practical Example 14 and were managed under the same conditions. CD8 huMVR CAR-T and CD4/CD8 huMVR CAR-T were constructed using an improved CAR construct (CAR_euCD137) and efficacy was evaluated in an intraperitoneal animal model. To induce the intraperitoneal animal model, luciferase-expressing LCL-Luc cell line at $2\times10^6$ cells/100 µL DPBS/head was administered through the abdominal cavity and nine days later, the animals were classified into five groups according to photon values. After dividing into respective groups, the CD8 MVR CAR-T was administered by injection into the tail vein at $0.5\times10^6$ cells/100 µL DPBS/head (dose 1), $2.0\times10^6$ cells/100 µL DPBS/head (dose 2) and $10\times10^6$ cells/100 µL DPBS/head (dose 3), or $0.5\times10^6$ cells of CD4 and CD8 huMVR CAR-T, respectively, were mixed and administered once. In all animal experiments, cancer size and viability were checked periodically. (FIG. 13) The specific experimental method was the same as described in Example 14.

After isolating CD4 and CD8 from PBMCs isolated from healthy adult blood, the huMVR scFv was expressed in a modified CAR construct, and the efficacy evaluation was performed in a peritoneal animal model using huMVR CAR-T.

The efficacy of huMVR CAR-T was evaluated by imaging and photon values exhibited by luciferase-expressing cancer cells.

Upon checking 2 times per a week using IVIS imaging equipment, 27 days after the CAR-T administration in the experimental group all control group mice in which cancer was present and CAR-T was not administered had died. However, all individuals in which cancer was formed and huMVR CAR-T was administered survived for at least 27 days. In the group administered CD8 huMVR CAR-T at low dose ($0.5 \times 10^6$ cells/100 μL DPBS/head), tumors showed a tendency to decrease and then increase again after 10 days; the group administered CD8 huMVR CAR-T at medium dose ($2.0 \times 10^6$ cells/100 μL DPBS/head) showed a tendency for photon values to slowly decrease through day 27. However, when the CD8 huMVR CAR-T was administered at a high dose ($10.0 \times 10^6$ cells/head), it was confirmed that all cancer disappeared after 13 days. In addition, when the CD4 and CD8 MVR CAR-T were administered together at low doses, it was confirmed that the cancer disappeared in most mice (3 out of 5 mice) by around day 27, although this was not as efficacious as the high dose of CD8 huMVR CAR-T. Accordingly, this experiment showed that huMVR CAR-T has an effect at a medium dose or higher, and when used together with CD4 rather than CD8 alone, the effect was present even when using a smaller dose of CAR-T. (FIG. 13)

Practical Example 17: Evaluation of the Efficacy of CD4/8 huMVR CAR-T in Subcutaneous Animal Models In Practical Example 13, the production of huMVR CAR-T using CD4 and CD8 T cells together when constructing MVR CAR-T was confirmed to be more effective when used in animal experiments. Based on the above example, CD4/CD8 huMVR CAR-T was produced and administered at low, medium, and high doses, and the efficacy of CAR-T was evaluated using a subcutaneous animal model.

When cancer growth was checked with an automatic caliper, in the group treated with the high dose ($5.0 \times 10^6$ cells/100 μL/head; dose 3), cancer growth slowed at day 10, cancer growth reversed at day 14, and the majority of cancer disappeared at day 17. As shown in FIG. 14A, cancer was difficult to confirm in the day 21 imaging. Even in the groups administered the medium dose ($2.0 \times 10^6$ cells/100 μL/head; dose 2) and low dose ($1.0 \times 10^6$ cells/100 μL/head; dose 1), cancer growth slowed starting on day 17 after CAR-T administration, and cancer decreased from day 21. However, as a result of using imaging equipment, there were some individuals in which cancer cells remained in the body for more than 4 weeks, and although the effect was shown at medium and low doses, the effect was slow compared to the high dose. When the cancer cells were imaged through IVIS imaging, although the tumor model was induced by subcutaneous administration, over time it was confirmed that the cancer had spread to the lymph nodes. However, when MVR CAR-T was administered, all metastatic cancer cells were killed.

(FIG. 15) In addition, when the viability of the animal model through huMVR CAR-T administration was confirmed through this experiment, all mice died on day 18 in the control mouse group not administered CAR-T, but all survived in the group administered MVR CAR-T. (FIG. 16)

Practical Example 18: In Vivo Identification of CD4/8 MVR CAR-T in Animal Models Blood obtained from the mouse used in Practical Example 17 was subjected to blood analysis to confirm the proportion and number of CAR-T present in the animal body. Blood analysis showed that CAR-T was confirmed at a low proportion in individuals administered CAR-T after 3 days, and the quantity of CAR-T increased rapidly from 7% to 31% in the high-dosage group after 10 days. This was the point at which the cancer size and photon values decreased in the MVR high-dosage group. In addition, in the case of medium- and low-dosage huMVR CAR-T, the CAR-T proportion was increased from day 17 after administration, and the cancer size and photon value were decreased from day 21. (FIG. 17)

TABLE 2

| Sequence number | Information |
|---|---|
| 1 | CDR1 of huMVR.H2 heavy chain |
| 2 | CDR2 of huMVR.H2 heavy chain |
| 3 | CDR3 of huMVR.H2 heavy chain |
| 4 | CDR1 of huMVR.L2 light chain |
| 5 | CDR2 of huMVR.L2 light chain |
| 6 | CDR3 of huMVR.L2 light chain |
| 7 | Variable region of huMVR.H2 heavy chain |
| 8 | Variable region of huMVR.L2 Light chain |
| 9 | scFv of huMVRL2H2 |
| 10 | Variable region of huMVR.H1 heavy chain |
| 11 | Variable region of huMVR.L1 light chain |
| 12 | scFv of huMVRL1H1 |
| 13 | 4-1BB signaling domain |
| 14 | euCD137 |
| 15 | MVR.L2H2 CAR |
| 16 | MVR.L2H2 CAR_euCD137 |
| 17 | CD19 CAR |
| 18 | CD19 CAR_euCD137 |
| 19 | EF1a-promoter |
| 20 | CD8-α leader sequence |
| 21 | Flag |
| 22 | CD19scFv |
| 23 | CD8/Hinge/Transmembrane Sequence |
| 24 | CD3z |
| 25 | Woodchuck/PRE |
| 26 | R/region |

For example, for claim construction purposes, it is not intended that the claims set forth below be construed in any way narrower than the literal language thereof, and it is thus not intended that exemplary embodiments from the specification be read into the claims. Accordingly, it is to be understood that the present invention has been described by way of illustration and not by way of limiting the scope of the claims. Accordingly, the present invention is limited only by the following claims. All publications, issued patents, patent applications, books and journal articles, cited in this application are each incorporated into the present application by reference in their entirety.

Sequence List Free Text
GA
 1. CDR1 of huMVR.H2 heavy chain
RYSVH

2. CDR2 of huMVR.H2 heavy chain
MIWGGGSTDYNSALKS

3. CDR3 of huMVR.H2 heavy chain
NEGDTTAGTWFAY

4. CDR1 of huMVR.L2 light chain
KASDHINNWLA

5. CDR2 of huMVR.L2 light chain
GATSLET

6. CDR3 of huMVR.H2 light chain
QQYWSTPFT

7. Variable region of huMV.R.H2 heavy chain
QVQLQESGPGLVKPSETLSLTCTVSGFSLSRYSVHWIRQPPGKGLEWLG
MIWGGGSTDYNSALKSRLTISKDNSKNQVSLKLSSVTAADTAVYYCARN
EGDTTAGTWFAYWGQGTLVTVSS 8. Variable region of huMVR.L2 Light chain
DIQMTQSPSSLSASVGDRVTITCKASDHINNWLAWYQQKPGKAPKLLIS
GATSLETGVPSRFSGSGSGKDYTLTISSLQPEDFATYYCQQYWSTPFTF
GQGTKVEIK 9. scFv of huMVRL2H2
DIQMTQSPSSLSASVGDRVTTTCKASDHINNWLAWYQQKPGKAPKLLIS
GATSLETGVPSRFSGSGSGKDYTLTISSLQPEDFATYYCQQYWSTPFTF
GQGTKVEIKGGGGSGGGGSGGGGSQVQLQESGPGLVKPSETLSLTCTVS
GFSLSRYSVHWIRQPPGKGLEWLGMIWGGGSTDYNSALKSRLTISKDNS
KNQVSLKLSSVTAADTAVYYCARNEGDTTAGTWFAYWGQGTLVYSS 10. Variable region of huMVR.HI heavy chain
QVQLQESGPGLVKPSETLSLTCTVSGGSISRYSVHWIRQPPGKGLEWIG
MIWGGGSTDYNSALKSRVTISVDTSKNQFSLKLSSVTAADTAVYYCARN
EGDTTAGTWFAYWGQGTLVTVSS 11. Variable region of huMVR.L1 light chain
DIQMTQSPSSLSASVGDRVTITCRASDHINNWLAWYQQKPGKAPKLLLY
GATRLESGVPSRFSGSGSGTDYTLTISSLQPEDFATYYCQQYWSTPFTF
GGGTKVEIK 12. scFv huMVRL1H1
DIQMTQSPSSLSASVGDRVTITCRASDHINNWLAWYQQKPGKAPKLLLY
GATRLESGVPSRFSGSGSGTDYTLTISSLQPEDFATYYCQQYWSTPFTF
GGGTKVEIKGGGGSGGGGSGGGGSQVQLQESGPGLVKPSETLSLTCTVS
GGSISRYSVHWIRQPPGKGLEWIGMIWGGGSTDYNSALKSRVTISVDTS
KNQFSLKLSSVTAADTAVYYCARNEGDTTAGTWFAYWGQGTLVTVSS 13. 4-1BB signaling domain
KRGRKKLLYIFKQPFMRPVQTTQEEDGCSCRFPEEEEGGCEL 14. cuCD137
RFSVVKRGRKKLLYIFKQPFMRPVQTTQEEDGCSCRFPEEEEGGCEL 15. sequence of MVR.L2H2 CAR
GCTGCCGATTTCCAGAAGAAGAAGAAGGAGGATGTGAACTG
AGAGTGAAGTTCAGCAGGAGCGCAGACGCCCCCGCGTACAAGCAGGGCC
AGAACCAGCTCTATAACGAGCTCAATCTAGGACGAAGAGAGGAGTACGA
TGTTTTGGACAAGAGACGTGGCCGGGACCCTGAGATGGGGGAAAGCCG
AGAAGGAAGAACCCTCAGGAAGGCCTGTACAATGAACTGCAGAAAGATA
AGATGGCGGAGGCCTACAGTGAGATTGGGATGAAAGGCGAGCGCCGGA
GGGGCAAGGGGCACGATGGCCTTTACCAGGGTCTCAGTACAGCCACCAA
GGACACCTACGACGCCCTTCACATGCAGGCCCTGCCCCCTCGCTAA 16. sequence of MVR.L2H2 CAR_euCD137
GATATTCAGATGACCCAGTCCCCGAGCTCCCTGTCCGCCTCTGTGGGCG
ATAGGGTCACCATCACCTGCAAGGCCAGTGACCACATCAACAACTGGCT
GGCCTGGTATCAACAGAAACCAGGAAAAGCTCCGAAACTACTGATCAGC
GGCGCCACCTCTCTGGAAACCGGAGTCCCTTCTCGCTTCTCTGGTTCCG
GATCTGGGAAGGATTACACTCTGACCATCAGCAGTCTGCAGCAGCCGGA
AGACTTCGCAACTTATTACTGTCAGCAGTACTGGTCCACCCCCTTCACC
TTCGGACAGGGTACCAAGGTGGAGATCAAAGGCGGAGGCGGATCTGGCG
GCGGAGGGAAGTGGCGGAGGGGGATCTCAGGTGCAGCTGCAGGAGTCGG
GCCCAGGACTCCTGAAGCCTTCGGAGACCCTGTCCCTCACCTGCACTGT
CTCTGGTTTCTCCCTGAGTCGGTACTCTGTGCATTGGATCCGGCAGCCC
CCAGGGAAGGGACTGGAGTGGCTGGGGATGATCTGGGGAGGCGGCAGCA
CCGACTACAACAGCGCCCTGAAGTCCCGACTGACCATATCAAAGGACAA
CTCCAAGAACCAGGTGCCTTGAAGCTGAGCTCTGTGACCGCTGCGGACA
CGGCCGTGTATTACTGTGCGAGAAATGAGGGCGATACCACCGCCGGCAC
TTGGTTTGCCTATTGGGGCCAGGGAACCCTGGTCACCGTCTCCTCAACC
ACGACGCCAGCGCCGCGACCACCAACACCGGCGCCCACCATCGCTAG
CCAGCCCCTGTCCCTGCGCCCAGAGAGGCGTGCCGGCCAGCGGCGGGGG
GCGCAGTGCACACGAGGGGGCTGGACTTCGCCTGTGATATCTACATCTG
GGCGCCCTTGGCCGGGACTTGTGGGGTCCTTCTCCTGTCACTGGTTATC
ACCCTTTACTGCCGTTTCTCTGTTAAACGGGGCAGAAAGAACTCCTGTA
TATATTCAAACAACCATTTATGAGACCAGTACAAACTACTCAAGAGGAA
GATGGCTGTAGCTGCCGATTTCCAGAAGAAGAAGAAGGAGGATGTGAAC
TGAGAGTGAAGTTCAGCAGGAGCGCAGACGCCCCCGCGTACAAGCAGGG
CCAGAACCAGCTCTATAACGAGCTCAATCTAGGACGAAGAGAGGAGTAC
GATGTTTTGGACAAGAGACGTGGCCGGGACCCTGAGATGGGGGGAAAGC
CGAGAAGGAAGAACCCTCAGGAAGGCCTGTACAATGAACTGCAGAAAGA
TAAGATGGCGGAGGCCTACAGTGAGATTGGGATGAAAGGCGAGCGCCGG
AGGGGCAAGGGGCACGATGGCCTTTACCAGGGTCTCAGTACAGCCACCA
AGGACACCTACGACGCCCTTCACATGCAGGCCCTGCCCCCTCGCTAA 17. sequence of CD19CAR
GACATCCAGATGACACAGACTACATCCTCCCTGTCTGCCTCTCTGGGAG
ACAGAGTCACCATCAGTTGCAGGGCAAGTCAGGACATTAGTAAATATTT
AAATTGGTATCAGCAGAAACCAGATGGAACTGTTAAACTCCTGATCTAC
CATACATCAAGATTACACTCAGGAGTCCCATCAAGGTTCAGTGGCAGTG
GGTCTGGTAACAGATTATTCTCTCACCATTAGCAACCTGGAGCAAGAAG
ATATTGCCACTTACTTTTGCCAACAGGGTAATACGCTTCCGTACACGTT
CGGAGGGGGACCAAGCTGGAGATCACAGGTGGCGGCTGGCTCGGGCGG
TGGTGGGTCGGTGGCGGCGGATCTGAGGTGAAACTGCAGGAGTCAGGA
CCTGGCCTGGTGGCGCCCTCACAGAGCCTGTCCGTCACATGCACTGTGT
CAGGGGTCTCATTACCCGACTATGGTGTAAGCTGGATTCGCCAGCCTCC -continued
ACGAAAGGGTCTGGAGTGGCTGGGAGTAATATGGGGTAGTGAAACCACA
TACTATAATTCAGCTCTCAAATCCAGACTGACCATCATCAAGGACAACT
CCAAGAGCCAAGTTTTCTTAAAAATGAACAGTCTGCAAACTGATGACAC
AGCCATTTACTACTGTGCCAAACATTATTACTACGGTGGTAGCTATGCT
ATGGACTACTGGGGCCAAGGAACCTCAGTCACCGTCTCCTCAACCACGA
CGCCAGCGCCGCGACCACCAACACCGGCGCCCACCATCGCTAGCCAGCC
CCTGTCCCTGCGCCCAGAGGCGTCCGGCCAGCGGCGGGGGCGCAGTGC
ACACGAGGGGGCTGGACTTCGCCTGTATATCCTACATCTGGGCGCCCT
TGGCCGGGACTTGTGGGGTCCTTCTCCTGTCACTGGTTATCACCCTTTA
CTGCAAACGGGGCAGAAAGAAACTCCTGTATATATTCAAACAACCATTT
ATGAGACCAGTACAAACTACTCAAGAAGGAAGATGGCTGTAGCTGCCGA
TTTCCAGAAGAAGAAGGAGGATGTGAACTGAGAGTGAAGTTCAGCA
GGAGCGCAGACGCCCCCGCGTACAAGCAGGGCCAGAACCAGCTCTATAA
CGAGCTCAATCTAGGACGAAGAGAGGCATACGATGTTTTGGACAAGAGA
CGTGGCCGGGACCCTGAGATGGGGGGAAAGCCGAGAAGGAAGAACCCTC
AGGAAGGCCTGTACAATGAACTGCAGAAAGATAAGATGGAGGAGGCCTA
CAGTGAGATTGGGATGAAAGGCGAGCGCCGGAGGGGCAAGGGGCACGAT
GGCCTTTACCAGGGTCTCAGTACAGCCACCAAGGACACCTACGACGCCC
TTCACATGCAGGCCCTGCCCCCTCGCTAA 18. sequence of CD19 CAR_euCD137
GACATCCAGATGACACAGACTACATCCTCCCTGTCTGCCTCTCTGGGAG
ACAGAGTCACCATCAGTTGCAGGGCAAGTCAGGACATTAGTAAATATTT
AAATTGGTATCAGCAGAAACCAGATGGAACTGTTAAACTCCTGATCTAC
CATACATCAAGATTACATCAGGAGTCCCATCAAGGTTCAGTGGCAGTGG
GTCTGGAACAGATTATTCTCTCACCATTAGCAACCTGGAGCAAGAAGAT
ATTGCCACTTACTTTTGCCAACAGGGTAATACGCTTCCGTACACGTTCG
GAGGGGGGACCAAGCTGGAGATCACAGGTGGCGGTGGCTCGGGCGGTGG
TGGGTCGGGTGGCGGCGGATCTGAGGTGAAACTGCAGGAGTCAGGACCT
GGCCTGGTGGCGCCCTCACAGAGCCTGTCCGTCACATGCACTGTCTAGG
GGTCTCATTACCCGACTATGGTGTAAGCTGGATTCGCCAGCCTCCACGA
AAGGGTCGGAGTGGCTGGGAGTAATATGGGGTAGTGAAACCACATACTA
TAATTCAGCTCTCAAATCCAGACTGAGGATCATCAAGGACAACTCCAAG
AGCCAAGTTTTCTTAAAAATGAACAGTCTGCAAACTGATGACACAGCCA
TTTACTACTGTGCCAAACATTATTACTACGGTGGTAGCTATGCTATGGA
CTACTGGGGCCAAGGAACCTCAGTCACCGTCTCCTCAACCACGACGCCA
GCGCCGCGACCACCAACACCGGCGCCCACCATCGCTAGCCAGCCCCTGT
CCCTGCGCCCAGAGGCGTGCCGGCCAGCGGCGGGGGCGCAGTCACACG
AGGGGGCTGGACTTCGCCTGTATATCTAGATCTGGGCGCCCTTGGCCG
GGACTTGTGGGGTCCTTCTCCTGTCACTGGTTATCACCCTTTACTGCCG
TTTCTCTGTTGTTAAACGGGGCAGAAAGAAACTCCTGTATATATTCAAA
CAACCATTTATGAGACCAGTACAAACTACTCAAGAGGAAGATGGCTGTA -continued
GCTGCCGATTTCCAGAAGAAGAAGAAGGAGGATGTGAACTGAGAGTGAA
GTTCAGCAGGAGCGCAGACGCCCCCGCGTACAAGCAGGGCCAGAACCAG
CTCTATAACGAGCTCAATCTAGGACGAAGAGAGGAGTACGATGTTTTGG
ACAAGAGACGTGGCCGGGACCCTGAGATGGGGGGAAAGCCGAGAAGGAA
GAACCCTCAGGAAGGCCTGTACAATGAACTGCAGAAAGATAAGATGGCG
GAGGCCTACAGTGAGATTGGGATGAAAGGCGTAGCGCCGGAGGGGCAAG
GGGCACGATGGCCTTTACCAGGGTCTCAGTACAGCCACCAAGGACACCT
ACGACGCCCTTCACATGCAGGCCCTGCCCCCTCGCTAAGTCGACA 19. EF1a-promoter
gatggagtttccccacactgagtgggtggagactgaagttaggccagct tggcacttgatgtaattctccttggaatttgcccttttttgagtttggat cttggttcattctaagcctcagacagtggttcaaagttttttcttccag gtgtcgtga 20. CD8-α leader sequence
GGATCCATGGCCTTACCAGTGACCGCCTTGCTCCTGCCGCTGGCCTTGC
TGCTCCACGCCGCCAGGCCG 21. Flag
gactacaaggacgacgatgacaag 22. CD19scFv
GACATCCAGATGACACAGACTACATCCTCCCTGTCTGCCTCTCTGGGAG
ACAGAGTCACCATCAGTTGCAGGGCAAGTCAGGACATTAGTAAATATTT
AAATTGGATACAGCAGAAACCAGATCCAACTGTTAAACTCCTGATCTAC
CATACATCAAGATTACACTCAGGAGTCCCATCAAGGTTCAGTGGCAGTG
GGTCTGGAACAGATTATTCTCTCACCATTAGCAACCTGGAGCAAGAAGA
TATTGCCACTTACTTTTGCCAACAGGGTAATACGCTTCCGTACACGTTC
GGAGGGGGGACCAAGCTGGAGATCACAGGTGGCGGTGGCTCGGGCGGTG
GTGGGTCGGGTGGCGGCGGATCTGAGGTCAAACTGCAGGAGTCAGGACC
TGGCCTGGTGGCGCCCTCACAGAGCCTGTCCGTCACATGCACTGTCTCA
GGGGTCTCATTACCCGACTATGGTGTAAGCTGGATTCGCCAGCCTCCAC
GAAAGGGTCTGGAGTGGCTGGGAGTAATATGGGGTAGTGAAACCACATA
CTATAATTCAGCTCTCAAATCCAGACTGACCATCATCAAGGACAACTCC
AAGAGCCAAGTTTTCTTAAAAATGAACAGTCTGCAAACTGATGACACAG
CCATTTACTACTGTGCCAAACATTATTACTACGGTGGTAGCTATGCTAT
GGACTACTGGGGCCAAGGAACCTCAGTCACCGTCTCCTCA 23. CD8/Hinge/Transmembrane Sequence
ACCACGACGCCAGCGCCGCGACCACCAACAACACCGGCGCCCACCATCG
CTAGCCAGCCCCTGTCCCTGCGCCCAGAGGCGTGCCGGCCAGCGGCGGG
GGCGCAGTGCACACGAGGGGGCTGGACTTCGCCTGTGATATCTACATCT
GGGCGCCCTTGGCCGGGACTTGTGGGGTCCTTCTCCTGTCACTGGTTAT
CACCCTTTACTGC 24.CD3z
AGAGTGAAGTTCAGCAGGAGCGCAGACGCCCCCGCGTACAAGCAGGGCC
AGAACCAGCTCTATAACGAGCTCAATCTAGGACGAAGAGAGGACTACGA
TGTTTTGGACAAGAGACGTGGCCGGGACCCTGAGATGGGGGGAAAGCCG

```
AGAAGGAAGAACCCTCAGGAAGGCCTGTACAATGAACTGCCAGAAAGAT

AAGATGGCGGAGGCCTACAGTGAGATTGGGATGAAAGGCGAGCGCCGGA

GGGGCAAGGGGCACGATGGCCTTTACCAGGGTCTCAGTACAGCCACCAA

GGACACCTACGACGCCCTTCACATGCAGGCCCTGCCCCTCGCTAA

25. Woodchuck/PRE
Atcaacctctggattacaaaattgtgaaagattgactggtattcttaac tatgttgctccttttacgctatgtggatagctgctttaatgcctttgta tcatgctatgcttcccgtatggctttcattttctcctccttgtataaat cctggttgctgtcttagggagttgtggcccgttgtcaggcaacgtggcg tggtgtgcactgtgtttgctgacgcaaaccccactggttggggcattg ccaccacctgtcagctccttccgggactttcgctttcccctccctatt gccacggcggaactcatcgccgcctgccttgcccgctgctggacagggg ctcggctgttgggcactgacaattccgtggtgttgtcggggacgctgac gtcctttccatggctgctcgcctgtgttgccacctggattctgcgcggg acgtccttctgtctacgtcccttcggccctcaatccagcggaccttcct tcccgcggcctgctgccggctctgcggcctcttccgcgtcttcgccttc gccctgcagacgagtcggatctccctttgggccgcctccccgcctg 26. R/region
GGGTGTGTGTGGTTAGACCAGATCTGAGCCTGGGAGCTCTCTGGCTAAC

TAGGGAACCCACTGCTTAAGCCTCAATAAAGCTTGCCTTGCGTGCTTCA
```

The invention claimed is:

1. An antigen binding molecule, comprising, a heavy-chain variable region of SEQ ID NO: 7 and a light-chain variable region of SEQ ID NO: 8, wherein the antigen-binding molecule is a chimeric antigen receptor (CAR).

2. An antigen binding molecule according to claim 1, comprising the amino acid sequence represented by SEQ ID NO: 9.

3. An antigen binding molecule according to claim 1, further comprising the amino acid sequence represented by SEQ ID NO: 13.

4. An antigen binding molecule according to claim 1, further comprising an amino acid sequence represented by SEQ ID NO: 14.

5. An antigen binding molecule according to claim 1, further comprising a transmembrane domain and an intracellular signaling domain for activating T cells.

6. An antigen binding molecule according to claim 5, in which the said transmembrane domain is selected from the group: of an alpha chain of a T cell receptor, a beta chain of a T cell receptor, a zeta chain of a T cell receptor, CD28, CD45, CD4, CD5, CD8, CD9, CD16, CD22, CD33, CD37, CD64, CD80, CD86, CD134, CD137 and CD154, wherein the said intracellular signaling domain is a CD3zeta signaling domain and a co-stimulatory signaling domain.

7. An antigen binding molecule according to claim 6, wherein the co-stimulatory signaling domain is selected from the group of CD28, OXO40, CD27, ICAM-1, CD278, and CD137.

8. A method of treating cancer, comprising a step of administering, to a patient having cancer, a pharmaceutical composition comprising a T cell comprising a therapeutically effective quantity of the antigen-binding molecule of claim 1.

9. The method of claim 8, wherein the pharmaceutical composition comprises CD8+ T cells, or CD4+ T cells and CD8+ T cells.

10. The method of claim 9, wherein the pharmaceutical composition comprises CD4+ T cells and CD8+ T cells.

11. The method of claim 10, wherein the proportion of cell counts of CD4+ T cells to CD8+ T cells is substantially 1:1.

12. A therapeutic pharmaceutical composition for treating cancer, comprising as a pharmaceutically effective ingredient, T cells comprising the antigen-binding molecule of claim 1.

13. A therapeutic pharmaceutical composition of claim 1 in which the pharmaceutical composition either comprises CD8+ T cells or comprises CD4+ T cells and CD8+ T cells.

14. The therapeutic pharmaceutical composition of claim 13, wherein the pharmaceutical composition comprises CD4+ T cells and CD8+ T cells.

15. The therapeutic pharmaceutical composition of claim 14, in which the proportion of cell counts of CD4+ T cells to CD8+ T cells is substantially 1:1.

* * * * *